US007303652B2

(12) United States Patent
Riehle et al.

(10) Patent No.: US 7,303,652 B2
(45) Date of Patent: *Dec. 4, 2007

(54) REDUCED BYPRODUCT HIGH SOLIDS POLYAMINE-EPIHALOHYDRIN COMPOSITIONS

(75) Inventors: Richard James Riehle, Wilmington, DE (US); Ronald Busink, Bennekom (NL); Massimo Berri, Amersfoort (NL); Wilm Stevels, Harderwijk (NL)

(73) Assignee: Hercules Incorporated, Wilmington, DE (US)

( * ) Notice: Subject to any disclaimer, the term of this patent is extended or adjusted under 35 U.S.C. 154(b) by 178 days.

This patent is subject to a terminal disclaimer.

(21) Appl. No.: 10/013,049

(22) Filed: Dec. 10, 2001

(65) Prior Publication Data

US 2003/0000667 A1  Jan. 2, 2003

Related U.S. Application Data

(60) Provisional application No. 60/254,439, filed on Dec. 9, 2000.

(51) Int. Cl.
*D21H 17/55* (2006.01)
*D21H 21/20* (2006.01)
*C08G 69/46* (2006.01)
*C12S 13/00* (2006.01)

(52) U.S. Cl. .............. 162/164.3; 162/164.6; 435/262; 435/262.5; 435/278; 524/17

(58) Field of Classification Search ............. 435/262, 435/262.5, 277, 278; 162/164.3, 164.6
See application file for complete search history.

(56) References Cited

U.S. PATENT DOCUMENTS

| | | | |
|---|---|---|---|
| 2,595,935 A | 5/1952 | Daniel et al. ............... 92/3 |
| 2,926,154 A | 2/1960 | Keim .................... 260/29.2 |
| 3,197,427 A | 7/1965 | Schmalz ................ 260/29.2 |
| 3,248,353 A | 4/1966 | Coscia ................... 260/29.2 |
| 3,311,594 A | 3/1967 | Earle ...................... 260/77.5 |
| 3,332,901 A | 7/1967 | Keim .................... 260/29.2 |
| 3,655,506 A | 4/1972 | Baggett .................... 162/164 |
| 3,891,589 A | 6/1975 | Ray-Chaudhuri ....... 260/29.2 |
| 4,240,935 A | 12/1980 | Dumas ........................ 260/9 |
| 4,388,439 A | 6/1983 | Maslanka ................ 524/845 |
| 4,452,894 A | 6/1984 | Olsen et al. .............. 435/263 |
| 4,477,570 A | 10/1984 | Colaruotolo et al. ....... 435/253 |
| 4,487,884 A | 12/1984 | Maslanka ................ 524/845 |
| 4,493,895 A | 1/1985 | Colaruotolo et al. ....... 435/262 |
| 4,501,640 A | 2/1985 | Soerens ................... 162/111 |
| 4,501,862 A | 2/1985 | Keim ..................... 525/430 |
| 4,528,316 A | 7/1985 | Soerens .................. 524/503 |
| 4,684,439 A | 8/1987 | Soerens .................. 162/111 |
| 4,788,243 A | 11/1988 | Soerens .................. 524/503 |
| 4,853,431 A | 8/1989 | Miller ...................... 524/608 |
| 4,857,586 A | 8/1989 | Bachem et al. .......... 524/845 |
| 4,975,499 A | 12/1990 | Bachem et al. .......... 525/430 |
| 5,017,642 A | 5/1991 | Hasegawa et al. ........ 524/608 |
| 5,019,606 A | 5/1991 | Marten et al. ........... 523/414 |
| 5,056,855 A | 10/1991 | Moravsky ................. 296/98 |
| 5,171,795 A | 12/1992 | Miller et al. ............ 525/430 |
| 5,187,219 A | 2/1993 | Furman, Jr. ............. 524/377 |
| 5,189,142 A | 2/1993 | Devore et al. .......... 528/339.3 |
| 5,239,047 A | 8/1993 | Devore et al. .......... 528/339.3 |
| 5,246,544 A | 9/1993 | Hollenberg et al. ......... 162/111 |
| 5,256,727 A | 10/1993 | Dulany et al. ........... 524/608 |
| 5,330,619 A | 7/1994 | Johnson et al. ............. 162/5 |
| 5,338,807 A | 8/1994 | Espy et al. ............. 525/430 |
| 5,364,927 A | 11/1994 | Devore et al. .......... 528/339.3 |
| 5,374,334 A | 12/1994 | Sommese et al. ........... 162/111 |
| 5,470,742 A | 11/1995 | Bull et al. ................ 435/262 |
| 5,516,885 A | 5/1996 | Gorzynski et al. ......... 528/482 |
| H1613 H | 11/1996 | Espy ....................... 528/489 |
| 5,786,429 A | 7/1998 | Allen ...................... 525/430 |
| 5,843,763 A | 12/1998 | Bull et al. .............. 435/262.5 |
| 5,871,616 A | 2/1999 | Bull et al. .............. 162/164.3 |
| 5,902,862 A | 5/1999 | Allen ...................... 525/430 |
| 5,972,691 A | 10/1999 | Bates et al. .............. 435/278 |
| 5,994,449 A | 11/1999 | Maslanka ................. 524/503 |
| 6,056,855 A | 5/2000 | Amey ................... 162/164.3 |
| 6,222,006 B1 | 4/2001 | Kokko et al. ............. 528/332 |
| 6,554,961 B1 * | 4/2003 | Riehle et al. ............ 162/164.3 |
| 2003/0205345 A1 * | 11/2003 | Riehle et al. ............ 162/164.3 |

FOREIGN PATENT DOCUMENTS

AU  5453400 A  1/2001

(Continued)

OTHER PUBLICATIONS

U.S. Appl. No. 09/001,787, filed Dec. 31, 1997, Riehle.

(Continued)

*Primary Examiner*—William H. Beisner
(74) *Attorney, Agent, or Firm*—Joanne Mary Fobare Rossi; Robert O'Flynn O'Brien

(57) ABSTRACT

A process for rendering a polyamine-epihalohydrin resin storage stable, is described. The process entails treating a polyamine-epihalohydrin resin composition, where the resin is formed in a reaction having a molar ratio of epihalohydrin to secondary amine group of less than about 0.5 and where the composition has a solids content of at least 15 wt % and includes CPD-forming species, with at least one enzymatic agent under conditions to inhibit, reduce or remove the CPD-forming species to obtain a gelation storage stable reduced CPD-forming resin so that the composition containing the reduced CPD-forming polyamine-epihalohydrin resin when stored for 24 hours at 50° C. and a pH of about 1.0 releases less than about 100 ppm dry basis of CPD.

37 Claims, No Drawings

FOREIGN PATENT DOCUMENTS

| CA | 979579 | 12/1975 |
|---|---|---|
| CA | 2375694 A1 | 12/2000 |
| EP | 0 349 935 | 6/1993 |
| GB | 865 727 | 4/1961 |
| WO | 92/22601 | 12/1992 |
| WO | 93/21384 | 10/1993 |
| WO | 96/40967 | 12/1996 |
| WO | 99/09252 | 2/1999 |
| WO | 99/33901 | 7/1999 |
| WO | WO-0077076 A1 | 12/2000 |

OTHER PUBLICATIONS

U.S. Appl. No. 09/224,107, filed Dec. 22, 1998, Riehle.
U.S. Appl. No. 09/330,200, filed Jun. 11, 1999, LaPre.
U.S. Appl. No. 09/363,224, filed Jul. 30, 1999, Allen.
U.S. Appl. No. 09/592,681, filed Jun. 12, 2000, Riehle.
U.S. Appl. No. 09/629,629, filed Jul. 31, 2000, Busink.
U.S. Appl. No. 10/006,027, filed Dec. 7, 2001, Riehle.
C. E. Castro et al., "Biological Cleavage of Carbon-Halogen Bonds Metabolism of 3- Bromopropanol by *Pseudomas* sp.", Biochimica et Biophysica Acta, 100, 384-392, 1965.
Siezen, R. J., et al., Protein Eng., 1991, vol. 4, No. 7, 719-37.
Dunlop-Jones, Paper Chemistry, ISBN 0-216-929090-1, Publisher: Chapman Hall, N.Y., Chapter 6, 1991, pp. 78-96.
P. J. Flory, Principles of Polymer Chemistry, pp. 91-95, Cornell University Press, Ithaca, NY (1953).
Jerry March, Advanced Organic Chemistry, pp. 218-236, Third Ed., John Wiley & Sons, New York (1985).

\* cited by examiner

REDUCED BYPRODUCT HIGH SOLIDS POLYAMINE-EPIHALOHYDRIN COMPOSITIONS

This application is related to U.S. Provisional Patent Application Ser. No. 60/254,439 filed Dec. 9, 2000 from which priority is claimed.

FIELD OF THE INVENTION

This invention relates to resins and aqueous compositions containing resins, and processes of forming resin compositions, especially for the paper industry, including strength agents, such as wet strength and dry strength agents, and creping agents. The present invention also relates to resins, as well as processes for their production, wherein the resins, and compositions and products, such as paper products, containing the resins have reduced residuals, such as epihalohydrins and epihalohydrin hydrolysis products. Still further, the present invention relates to resins, and compositions and products, such as paper products, which maintain low levels of residuals, such as epihalohydrins and epihalohydrin hydrolysis products, when stored. Still further, each aspect of the present invention relates to compositions having the resin at various solids contents, especially high solids contents.

BACKGROUND OF THE INVENTION

Wet strength resins are often added to paper and paperboard at the time of manufacture. In the absence of wet strength resins, paper normally retains only 3% to 5% of its strength after being wetted with water. However, paper made with wet strength resin generally retains at least 10%-50% of its strength when wet. Wet strength is useful in a wide variety of paper applications, some examples of which are toweling, milk and juice cartons, paper bags, and liner board for corrugated containers.

Dry strength is also a critical paper property, particularly in light of the recent trend for paper manufacturers to use high yield wood pulps in paper in order to achieve lower costs. These high yield wood pulps generally yield paper with significantly reduced strength when compared to paper made from highly refined pulps.

Commercially available wet strength resins include Kymene®557H, Kymene® 557LX, Kymene® SLX, Kymene® Plus, Kymene® 450 and Kymene® 736 wet strength resins, available from Hercules Incorporated, Wilmington, Del. Wet strength resins, such as those listed above, also provide increased dry strength to paper.

Resins similar to those used for imparting strength to paper are also often used as creping adhesives. In the manufacture of some paper products such as facial tissue, bathroom tissue, or paper towers, the paper web is conventionally subjected to a creping process in order to give it desirable textural characteristics, such as softness and bulk. The creping process typically involves adhering the web, a cellulose web in the case of paper, to a rotating creping cylinder, such as the apparatus known as a Yankee dryer, and then dislodging the adhered web with a doctor blade. The impact of the web against the doctor blade ruptures some of the fiber-to-fiber bonds within the web and causes the web to wrinkle or pucker.

The severity of this creping action is dependent upon a number of factors, including the degree of adhesion between the web and the surface of the creping cylinder. Greater adhesion causes increase softness, although generally with some loss of strength. In order to increase adhesion, a creping adhesive may be used to enhance any naturally occurring adhesion that the web may have due to its water content, which will vary widely depending on the extent to which the web has been previously dried. Creping adhesives should also prevent wear of the dryer surface and provide lubrication between the doctor blade and the dryer surface and reduce chemical corrosion, as well as controlling the extent of creping. A creping adhesive coating that adheres the sheet just tightly enough to the drum will give a good crepe, imparting absorbance and softness with the least possible loss of paper strength. If adhesion to the dryer drum is too strong, the sheet may pick or even "plug", i.e., underride the doctor blade, and wrap around the dryer drum. If there is not enough adhesion, the sheet will lift off too easily and undergo too little creping.

The creping adhesive, usually as an aqueous solution or dispersion, is generally sprayed onto the surface of the creping cylinder or drun, e.g., a Yankee dryer. This improves heat transfer, allowing more efficient drying of the sheet. If the pulp furnish sticks too strongly to the creping cylinder, release agents can be sprayed on the cylinder. The release agents are typically hydrocarbon oils. These agents aid in the uniform release of the tissue web at the creping blade, and also lubricate and protect the blade from excessive wear.

Examples of creping adhesive compositions include those disclosed in U.S. Pat. No. 5,187,219 to Furman, which is incorporated by reference herein in its entirety. The compositions comprise water-soluble glyoxylated acrylamide/diallyldimethyl-ammonium chloride polymer and a water-soluble polyol having a molecular weight below 3000 as a plasticizer for the polymer.

U.S. Pat. No. 5,246,544 to Hollenberg et al., which is incorporated by reference herein in its entirety, discloses a reversibly crosslinked creping adhesive which contains a nonself-crosslinkable material that is a polymer or oligomer having functional groups that can be crosslinked by ionic crosslinking and at least one metal, cationic crosslinking agent having a valence of four or more. The adhesive can also contain additives to modify the mechanical properties of the crosslinked polymers, e.g., glycols, polyethylene glycols, and other polyols such as simple sugars and oligosaccharides.

Polyaminoamide/epichlorohydrin creping adhesives are disclosed in U.S. Pat. No. 5,338,807 to Espy et al., U.S. Pat. No. 5,994,449 to Maslanka, and Canadian Patent 979,579 Giles et al., which are incorporated by reference herein in their entireties.

U.S. Pat. No. 5,374,334 to Sommese et al., which is incorporated by reference herein in its entirety, discloses a creping adhesive which is a crosslinked vinyl amine/vinyl alcohol polymer containing from about 1 to about 99% vinyl amine. Epichlorohydrin is disclosed as a crosslinking agent.

U.S. Pat. Nos. 4,684,439 and 4,788,243 to Soerens, which are incorporated by reference herein in their entireties, disclose creping adhesives comprising mixtures of polyvinyl alcohol and water soluble thermoplastic polyamide resin comprising the reaction product of a polyalkylenepolyamine, a saturated aliphatic dibasic carboxylic acid and a poly(oxyethylene) diamine.

In U.S. Pat. Nos. 4,501,640 and 4,528,316 to Soerens, which are incorporated by reference herein in their entireties, there is disclosed a creping adhesive comprising a mixture of polyvinyl alcohol and a water soluble, thermosetting cationic polyamide resin.

Commercially available creping adhesives include Crepetrol® 190, Crepetrol® 290, and Crepetrol® 80E cationic polymers, available from Hercules Incorporated, Wilmington, Del.

Moreover, polyamine-epihalohydrin resins, such as polyaminopolyamide-epihalohydrin resins often contain large quantities of epihalohydrin hydrolysis products. For example, commercial polyaminopolyamide-epichlorohydrin resins typically contain 1-10 wt % (dry basis) of the epichlorohydrin (epi) by-products, 1,3-dichloropropanol (1,3-DCP), 2,3-dichloropropanol (2,3-DCP) and 3-chloropropanediol (CPD). Epi by-products are also known as epi residuals. Production of such resins with reduced levels of epi by-products has been the subject of much investigation. Environmental pressures to produce resins with lower levels of adsorbable organic halogen (AOX) species have been increasing. "AOX" refers to the adsorbable organic halogen content of the resin, which can be determined by means of adsorption onto carbon. AOX includes epichlorohydrin (epi) and epi by-products (1,3-dichloropropanol, 2,3-dichloropropanol and 3-chloropropanediol) as well as organic halogen bound to the polymer backbone.

Several ways of reducing the quantities of epihalohydrin hydrolysis products have been devised. Reduction in the quantity of epihalohydrin used in the synthetic step is an alternative taught in U.S. Pat. No. 5,171,795. A longer reaction time results. Control over the manufacturing process is taught in U.S. Pat. No. 5,017,642 to yield compositions of reduced concentration of hydrolysis products. These patents are incorporated by reference herein in their entireties.

Post-synthesis treatments are also taught. U.S. Pat. No. 5,256,727, which is incorporated by reference in its entirety, teaches that reacting the epihalohydrin and its hydrolysis products with dibasic phosphate salts or alkanolamines in equimolar proportions converts the chlorinated organic compounds into non-chlorinated species. To do this it is necessary to conduct a second reaction step for at least 3 hours, which adds significantly to costs and generates quantities of unwanted organic or inorganic materials in the wet strength composition. In compositions containing large amounts of epihalohydrin and epihalohydrin hydrolysis products (e.g., about 1-6% by weight of the composition), the amount of organic material formed is likewise present in undesirably large amounts.

U.S. Pat. No. 5,516,885 and WO 92/22601, which are incorporated by reference in their entireties, disclose that halogenated by-products can be removed from products containing high levels of halogenated by-products as well as low levels of halogenated by-products by the use of ion exchange resins. However, it is clear from the data presented that there are significant yield losses in wet strength composition and a reduction in wet strength effectiveness.

It is known that nitrogen-free organohalogen-containing compounds can be converted to a relatively harmless substance. For example, 1,3-dichloro-2-propanol, 3-chloro-1,2-propanediol (also known as 3-chloropropanediol, 3-monochloropropanediol, monochloropropanediol, chloropropanediol, CPD, 3-CPD, MCPD and 3-MCPD) and epichlorohydrin have been treated with alkali to produce glycerol.

The conversion of nitrogen-free organohalogen compounds with microorganisms containing a dehalogenase is also known. For example, C. E. Castro, et al. ("Biological Cleavage of Carbon-Halogen Bonds Metabolism of 3-Bromopropanol by Pseudomonas sp.", *Biochimica et Biophysica Acta*, 100, 384-392, 1965), which is incorporated by reference in its entirety, describes the use of Pseudomonas sp. isolated from soil that metabolizes 3-bromopropanol in sequence to 3-bromopropionic acid, 3-hydroxypropionic acid and $CO_2$.

Various U.S. patents also describe the use of microorganisms for dehalogenating halohydrins, eg., U.S. Pat. Nos. 4,452,894; 4,477,570; and 4,493,895. Each of these patents is hereby incorporated by reference as though set forth in full herein.

U.S. Pat. Nos. 5,470,742, 5,843,763 and 5,871,616, which are incorporated by reference herein in their entireties, disclose the use of microorganisms or enzymes derived from microorganisms to remove epihalohydrin and epihalohydrin hydrolysis products from wet strength compositions without reduction in wet strength effectiveness.

U.S. application Ser. No. 09/629,629, filed Jul. 31, 2000, which is incorporated by reference herein in its entirety, is directed to the use of microorganisms or enzymes derived from microorganisms to remove epihalohydrin and epihalohydrin hydrolysis products from resin compositions, and discloses a preferred sequential method for growth of the microorganisms.

Still further, U.S. Pat. No. 5,972,691 and WO 96/40967, which are incorporated by reference in their entireties, disclose the treatment of wet strength compositions with an inorganic base after the synthesis step (i.e., after the polymerization reaction to form the resin) has been completed and the resin has been stabilized at low pH, to reduce the organo halogen content of wet strength compositions (e.g., chlorinated hydrolysis products) to moderate levels (e.g., about 0.5% based on the weight of the composition). The composition so formed can then be treated with microorganisms or enzymes to economically produce wet strength compositions with very low levels of epihalohydrins and epihalohydrin hydrolysis products.

It is also known that epihalohydrin and epihalohydrin hydrolyzates can be reacted with bases to form chloride ion and polyhydric alcohols. U.S. Pat. No. 4,975,499 teaches the use of bases during the synthetic step to reduce organo chlorine contents of wet strength composition to moderate levels (e.g., to moderate levels of from about 0.11 to about 0.16%) based on the weight of the composition. U.S. Pat. No. 5,019,606 teaches reacting wet strength compositions with an organic or inorganic base. These patents are incorporated by reference in their entireties.

Moreover, U.S. application Ser. No. 09/001,787, filed Dec. 31, 1997, and Ser. No. 09/224,107, filed Dec. 22, 1998 to Riehle, and WO 99/33901, and which are incorporated by reference in their entireties, disclose amongst other features, a process for reducing the AOX content of a starting water-soluble wet-strength resin comprising azetidinium ions and tertiary aminohalohydrin, which includes treating the resin in aqueous solution with base to form treated resin, wherein at least about 20 mole % of the tertiary aminohalohydrin present in the starting resin is converted into epoxide and the level of azetidinium ion is substantially unchanged, and the effectiveness of the treated resin in imparting wet strength is at least about as great as that of the starting wet-strength resin.

Still further, U.S. patent application Ser. No. 09/592,681, filed Jun. 12, 2000, Ser. No. 09/363,224, filed Jul. 30, 1999, 09/330,200, filed Jun. 11, 1999, each of which is incorporated by reference in its entirety, are directed to polyamine-epihalohydrin resin products, particularly polyamine-epihalohydrin resin products which can be stored with at least reduced formation of halogen containing residuals, such as 3-chloropropanediol (CPD). Moreover, these applications disclose the use of microorganisms or enzymes derived from microorganisms to remove epihalohydrin and epihalohydrin hydrolysis products from wet strength compositions without reduction in wet strength effectiveness.

WO 99/09252 describes thermosetting wet strength resins prepared from end-capped polyaminoamide polymers. The endcappers used are monocarboxylic acids or monofunctional carboxylic esters, and are used to control the molecular weight of the polyaminamide in order to obtain wet strength resins with a high solids content.

Each of the foregoing approaches has provided various results, and there has been a continuing need for improvement in the use of polyamine-epihalohydrin resin, especially at high solids content. In particular, there is still a need for resin compositions, such as wet strength, dry strength and creping agent resins, that can be provided in solutions or dispersion of reasonable viscosity at relatively high polymer solids concentrations. Thus, there is still a need for resins that can be prepared, stored, treated and transported as a dispersion or solution containing high solids concentrations without product deterioration from polymer crosslinking, such as gelation problems.

SUMMARY OF THE INVENTION

Enzyme treatment of tertiary amine-based resins can be carried out at higher concentration than what was previously disclosed, when the correct balance of conditions of time, temperature pH and enzyme concentration are utilized.

The present invention is directed to polyamine-epihalohydrin resin products, particularly polyamine-epihalohydrin resin products which can be stored with at least reduced formation of halogen containing residuals, such as 3-chloropropanediol (CPD).

The present invention is also directed to various uses of polyamine-epihalohydrin resins having at least reduced formation of halogen containing residuals, such as strength agents, including wet and dry strength agents, and creping agents.

The present invention is also directed to polyamine-epihalohydrin resin products which have reduced levels of formation of CPD upon storage, particularly paper products.

The present invention is also directed to various treatments of polyamine-epihalohydrin resins, including treatments to reduce the concentration of halogen containing residuals associated with the resins and/or compositions containing the resins.

The present invention is also directed to the preparation of storage stable polyamine-epihalohydrin resins and/or the treatment of polyamine-epihalohydrin resins to render such resins storage stable, especially at high solids concentrations.

DETAILED DESCRIPTION OF THE INVENTION

Unless otherwise stated, all percentages, parts, ratios, etc., are by weight.

Unless otherwise stated, a reference to a compound or component includes the compound or component by itself, as well as in combination with other compounds or components, such as mixtures of compounds.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed.

U.S. patent application Ser. No. 09/592,681, filed Jun. 12, 2000, Ser. No. 09/363,224, filed Jul. 30, 1999, and Ser. No. 09/330,200, filed Jun. 11, 1999, each of which is incorporated by reference in its entirety, are directed to the discovery that CPD that is formed in polyamine-epihalohydrin resins, after storage, is due to CPD-forming species that are associated with the oligomeric and/or polymeric component of the resin. It is disclosed in these applications that polyamine-epihalohydrin resins can be treated during and/or subsequent to production in such a manner so as to prevent the formation of, inhibit and/or remove elements associated with the polyamine-epihalohydrin resin which form CPD upon storage. For example, these applications disclose acid treatment, base treatment, low acid endgroups in the prepolymer, and enzyme treatment to remove or reduce CPD-forming species.

Thus, in one aspect of the invention disclosed in U.S. patent application Ser. No. 09/592,681, polyamine-epihalohydrin resin products which have reduced levels of formation of CPD upon storage and minimized levels of CPD in paper products can be produced by treating the resin with enzymatic agent. Thus, the CPD-forming species in the resin can be reduced and/or removed by treating the resin with an enzymatic agent that is capable of releasing CPD-forming species from the resin. The enzymatic agent can comprise one or more enzymes that are capable of releasing the CPD-forming species from the resin, such as at least one of esterases, lipases and proteases. It is preferred that the enzymatic agent has esterase activity. One skilled in the art knows that the protease class of enzymes can have esterase activity and that the esterase class of enzymes can have protease activity. A preferred class of proteases is the subtilisin group (E.C. 3.4.21.62. Homology modeling and protein engineering strategy of subtilases, the family of subtilisin-like serine proteinases, Siezen R J, de Vos W M, Leunissen J A, Dijkstra B W, Protein Eng. 1991, 4, 719-37), particularly the enzymes produced from *Bacillus licheniformis* (Swiss-Prot Accession Number: P00780), *Bacillus amyloliquifaciens* (P00782), and *Bacillus lentus* (P29600). The enzyme can be in pure form, or the enzyme can be unpurified. Still further, mixtures of enzymes can be used, which mixtures can include mixtures of pure enzymes, mixtures of unpurified enzymes, or mixtures of both. Particularly, preferred enzymatic agents are ALCALASE and SAVINASE, which are obtainable from Novozymes North America, Inc. Franklinton, North Carolina (formerly known as Novo Nordisk Biochem, North America, Inc.).

Expanding upon the above, in previous work, polyamine-epichlorohydrin resins with about 12-13.5 wt % solids were treated with ALCALASE 2.5 L type DX (Novozymes) to reduce or remove CPD-forming species. Under the treatment conditions, such as pH 8, 40° C., 6-8 hours and 0.25 g of ALCALASE for 30 g of resin, the resins had a tendency to develop high viscosity and become unusable. It has been surprisingly discovered in accordance with the present invention that by balancing treatment conditions, including pH, temperature, concentration of enzymatic agent, starting viscosity and solids concentration of polyamine-epihalohydrin resin containing compositions, such as polyaminopolyamide-epichlorohydrin resin compositions, could be treated with enzymatic agent to reduce or remove CPD-forming species with desired viscosity characteristics and excellent CPD release. These newly discovered conditions for enzymatic treatment allow the resin viscosity to be increased, decreased or maintained at the desired level, and permit the enzymatic treatment at low solids contents, as well as high solids concentrations of 15 wt % or greater.

Not wishing to be bound by theory, it is believed that as the active solid content increases, the crosslinking rate increases and therefore the viscosity increases. By judicious choice of reaction conditions, the rate of the crosslinking reaction that increases viscosity can be balanced with the rate of the enzymatic hydrolysis reaction, which decreases viscosity, to predictably obtain desired viscosity.

The present invention is useful because it enables higher throughput production for the enzymatic treatment and because lower levels of the expensive enzyme can be used. This technology should therefore enable (1) production of high solids, high effectiveness resins by allowing a longer time for azetidinium formation, and (2) production of lower AOX containing resins by increasing the conversion of tertiary aminochlorohydrin functionality to azetidinium functionality.

Thus, according to the present invention, it has been discovered that enzyme treatment for reducing or removing CPD-forming species can be performed at higher solids content of resin than would be expected. In this regard, the enzymatic treatment examples in the above-noted U.S. patent application Ser. No. 09/592,681 were performed at about 13-14 wt % solids. Thus, the enzyme treatment according to present invention can include solids contents as disclosed in the prior art, including concentrations as low as 4 wt % or lower. However, in contrast to the prior art, the solids content of the aqueous resin composition treated with enzymatic agent according to the present invention can be higher than 15 wt %, more preferably higher than about 20 wt %, and can be higher than about 25 wt % especially with creping agents. Preferred solids content ranges include from about 15 to 50 wt %, more preferably about 18 to 40 wt %. Preferably, for wet strength agents, the solids content is about 15 to 40 wt %, more preferably about 18 to 25 wt %, with one preferred solids value being about 21 wt %; and, for creping agents, the solids content is about 20 to 40 wt %, more preferably about 22 to 30 wt %, with one preferred solids value being about 26 wt %.

The terms creping aid, creping resin, creping agent and creping adhesive are used interchangeably and all have the same meaning throughout the specification.

The at least one enzymatic agent is added to the resin under suitable conditions to achieve sufficient hydrolysis of CPD forming species in the high resin solids composition. Preferably, conditions of time, temperature, pH, enzyme concentration, starting viscosity, and solids content are balanced in order to enable the hydrolysis reaction while minimizing degradation of performance of the resin, such as wet strength or creping effectiveness of the resin or preventing undesirably high resin viscosity. Thus, unexpectedly the hydrolysis of CPD-forming species can be performed at high solids concentrations by balancing the conditions of time, temperature, pH, enzyme concentration, starting viscosity, and solids content. For example, as the solids concentration increases, the pH and/or temperature should usually be decreased. Moreover, as the solids concentration increases, the enzyme concentration should usually be increased.

It is noted that the viscosity of the resin composition can increase or decrease from a starting viscosity during enzymatic treatment, and it can remain the same or substantially the same depending upon reaction conditions as noted above. For creping agents, it is usually preferred, but not limited to, that the viscosity at the end of the enzymatic treatment be the same or substantially the same as the starting viscosity. For example, with wet strength agents, it is usually preferred, but not limited to, that the viscosity is maintained or is decreased from the starting viscosity in the initial part of the treatment time and then is maintained or increased to the desired viscosity at the end of the treatment time. For example, with a resin having a starting Brookfield viscosity of about 100 to 300 cps and about 20-22 wt % active solids, it is preferred that conditions are chosen such that after treatment, the resin viscosity is maintained or decreased with the active solids being about 19-22 wt %. Further for example, with a resin having a starting Brookfield viscosity of about 100 to 300 cps and about 20-22 wt % active solids, it is preferred if the Gardner Holdt viscosity at the beginning of the reaction is about G to J, then it is desirable for the Gardner Holdt viscosity to decrease during the reaction to about F at the end of the reaction. Further for example, with a resin having a starting Brookfield viscosity of about 100 to 300 cps and about 20-22 wt % active solids, it is also preferred if the Gardner-Holt viscosity at the beginning of the reaction is about G to J, then it is desirable for the Gardner-Holt viscosity to decrease during the reaction to about A to E towards the end of the reaction, it is desirable to increase the treatment temperature until the Gardner-Holt viscosity has increased to about F to I. Further for example, with Kymene® E7219 (available from Hercules Incorporated, Wilmington, Del.) having a starting Brookfield viscosity about 200 to 300 cps with about 20-22 wt % active solids if the Gardner-Holt viscosity at the beginning of the reaction is about I, then it is desirable for the Gardner-Holt viscosity to decrease during the reaction to about F at the end of the reaction, resulting in a final resin (stabilized at about pH 3-3.5) with a Brookfield viscosity of about 100-150 cps. For example, with Kymene® E7219 (available from Hercules Incorporated, Wilmington, Del.) having a starting Brookfield viscosity about 200 to 300 cps with about 20-22 wt % active solids if the Gardner-Holt viscosity at the beginning of the reaction is about I, then it is desirable for the Gardner-Holt viscosity to decrease during the reaction to about C towards the end of the reaction, it is desirable to increase the treatment temperature until the Gardner-Holt viscosity has increased to about F.

For example, with creping agents, it is usually preferred, but not limited to, that the starting viscosity is below about 150 cps, more preferably below about 100 cps, more preferably below about 80 cps and even more preferably below about 40 cps. Preferably, the starting viscosity of the reaction mixture ranges from about 10 cps to 150 cps more preferably about 20 cps to 100 cps, and even more preferably about 40 to 80 cps.

With respect to the above, it is preferred to minimize or at least balance side reactions, such as polymeric breakdown or molecular weight increase in order that the viscosity of the reaction mixture is held below a viscosity that would not enable the reaction to proceed. Preferably, viscosity is measured using a Brookfield LVDV-II+ Programmable Viscometer at 25° C., or an equivalent such as Brookfield DV II+, Spindle LV2 at 60 or 100 rpm, depending on the viscosity. For the programmable viscometer, the procedure used was based on the Operating Instructions, Manual No. M/97-164. This Viscometer will determine viscosity only if the correct spindle and rpm is used for the viscosity of the sample according to instruction manual.

It is preferable that the properties of a creping agent are approximately the same subsequent to treatment as they were prior to treatment. Therefore, as noted above, preferably, the viscosity of the reaction mixture is maintained constant or substantially constant during the reaction for creping agents. In particular, the viscosity of the reaction mixture does not increase more than about 50%, more preferably no more than about 20%, and most preferably no more than about 10% from the starting viscosity.

It is further noted that conditions, preferably temperature, pH and concentration of enzymatic agent, can be varied during the reaction. For example, if the viscosity of the reaction mixture is higher than desired, the pH and/or temperature can be lowered and/or additional enzymatic agent can be added. Conversely, for example, if the viscosity of the reaction mixture is lower than desired, the pH and/or temperature can be raised.

The present invention is also directed to a process of reducing molecular weight or viscosity of a polyamine-epihalohydrin resin containing composition, comprising treating the composition containing polyamine-epihalohydrin resin with at least one enzymatic agent. The composition can comprise a high solids contents, such as a solids content of at least 15 wt %. Varying of the reaction conditions usually will change the time of the reaction. The pH and/or temperature can be lowered and/or additional enzymatic agent can be added.

For wet-strength resins and with using ALCALASE 2.5L type DX as the enzyme, specific examples of preferable conditions include the following. With a resin having a starting Brookfield viscosity of about 150 to 300 cps and about 20-22 wt % active solids, it is preferred to use a temperature of about 20-33° C., a pH of about 6.8-7.8, an ALCALASE 2.5L type DX (as received basis) to active solids ratio of about 1.0:20 to 1.0:5.0. More specifically, with Kymene® E7219 (available from Hercules Incorporated, Wilmington, Del.) having a starting Brookfield viscosity about 200 to 300 cps with about 20-22% active solids, it is preferred to use a temperature of about 23-27° C., a pH of about 6.8-7.5, an ALCALASE 2.5L type DX (as received basis) to active solids ratio of about 1.0:8.0 to 1.0:18.0 with a treatment time of 6-10 hours. It should be noted that as the treatment time is increased, the amount of CPD released from the CPD-producing species is desirably increased, with a preferred treatment time being 6 to 10 hours. Another example of conditions is the following: Kymene® E7219 (available from Hercules Incorporated., Wilmington, Del.) having a starting Brookfield viscosity about 200 to 300 cps with about 20-22% active solids, a temperature of about 35° C., a pH of about 7.5, an ALCALASE 2.5L type DX (as received basis) weight to active solids ratio (weight) of about 1.0:8.3.

The temperature can be at least about 0° C., more preferably about 10° C. to 80° C., even more preferably about 20° C. to 60° C., more preferably about 20° C. to 40° C. and more preferably about 20° C. to 30° C. The reaction time can be about 3 minutes to 350 hours, more preferably about 30 minutes to 48 hours, more preferably about 30 minutes to 96 hours, more preferably about 1 hour to 24 hours, and even more preferably about 2 hours to 12 hours. The pH of the enzymatic treatment will depend on the pH dependence of the specific enzyme and the other treatment conditions, and can vary between 1 to 11, preferably 2 to 10, even more preferably about 2.5 to 9, and even more preferably about 7-9, and even more preferably 7 to 8. Additional preferred pH ranges include; 5.0 to 8.0, 5.5 to 7.5, 6 to 9, 6 to 8.5, 6.5 to 8.

For example, the combined treatment can be started at pH 6.8-7.8 for the first 4-24 hours and than lowered to pH of 5.5-7.0 or the pH can be allowed to drift down to 6.5-7.2 for the latter 8-48 hours of the combined treatment.

The concentration of the enzyme will depend upon its activity. For example, but not limited to, the enzyme can be present in an amount of about 0.04 g of active enzyme (dry basis) to 1600 g polyamine-epichlorohydrin resin (dry basis) to 0.04 g of active enzyme (dry basis) to 1.5 g polyamine-epichlorohydrin resin (dry basis), also the enzyme can be present in an amount of about 0.04 g of active enzyme (dry basis) to 160 g polyamine-epichlorohydrin resin (dry basis) to 0.04 g of active enzyme (dry basis) to 4 g polyamine-epichlorohydrin resin (dry basis).

The concentration of the enzyme will depend upon its activity. For example, but not limited to, in the case of ALCALASE, the enzyme can be present in an amount of about 1 g of ALCALASE 2.5L type DX (as received) to 1600 g polyamine-epichlorohydrin resin (dry basis) to 1 g of ALCALASE 2.5L type DX (as received) to 1.5 g polyamine-epichlorohydrin resin (dry basis), also the enzyme can be present in an amount of about 1 g of ALCALASE 2.5L type DX (as received) to 160 g polyamine-epichlorohydrin resin (dry basis) to 1 g of ALCALASE 2.5L type DX (as received) to 4 g polyamine-epichlorohydrin resin (dry basis).

It is noted that following the guidelines and the non-limiting examples, set forth in the instant application one having ordinary skill in the art would be capable of determining treatment conditions and the balancing of treatment conditions to obtain hydrolysis of CPD-forming species at high solids concentrations and/or to obtain a reduction in molecular weight or viscosity. For example, as the solids concentration increases, the pH and/or temperature should usually be decreased, and the enzymatic agent concentration will usually be increased. Moreover, following the guidelines, one having ordinary skill in the art would be capable of determining enzymatic agents that are useful to remove CPD-forming species and/or to obtain a reduction in molecular weight or viscosity.

Moreover, preferred reaction conditions can be varied by using appropriate types and amounts of enzymes. For example, if the enzymatic agent has higher protease as compared to esterase activity (protease/esterase balance) with a polyamine-epichlorohydrin resin, then reaction conditions could be varied to higher pH, temperature and/or solids, such as reaction conditions above about pH 8 and/or temperature above about 40° C. and/or solids as high as about 40 wt %. Practical being defined as obtaining a reduced CPD-forming resin while having a resin with the desired viscosity. Although conditions will be dependent on the balance of esterase and protease activity of a particular enzyme, the preferred conditions with the present invention with ALCALASE 2.5 L type DX are the following: 15-50 wt % active solids, pH 6.9 to 7.9, at 0 to 35° C., for 4 to 24 hours and 8-20 g of active solids for 1 g of ALCALASE 2.5 L type DX (as received), and starting viscosity of 10 cP to 1000 cP. Moreover, it is noted that throughout the application the terminology enzymatic agent concentration is utilized. However, one having ordinary skill in the art would understand that enzymes can have different activities, and the concentration of the enzyme can be adjusted depending upon the activity.

The enzyme treatment can be applied on resins as produced in a resin synthesis process without further treatment. Moreover, the resins can be treated by various processes prior to reduction and/or removal of the CPD-forming species. Still further, after treatment to reduce and/or remove CPD-forming species, the resin can be treated by various processes. Yet still further, the resin can be treated by various processes prior to reduction and/or removal of the CPD-forming species, and the resin can also be treated by various processes after treatment to reduce and/or remove CPD-forming species. For the sake of brevity, a complete description of these processes is not being repeated herein, and reference is made to the above-identified U.S. patent application Ser. Nos. 09/629,629, 09/592,681, 09/363,224 and 09/330,200, which are incorporated by reference herein in their entireties.

The resins according to the present invention are capable of being stored without undue formation of CPD. More specifically, as an example, the solution will contain less than about 10 ppm (parts per million), more preferably less than about 5 ppm, and most preferably less than 1 ppm of CPD, when stored at about 13.5 wt % resin solids content. In the context of the present invention the phrase "resin solids" means the active polyamine-epihalohydrin of the composition.

To determine storage stability of resin solutions according to the present invention, a resin solution stability test is performed wherein the resin solution is stored for a period of 2 weeks at 50° C., and a pH of about 2.5 to 8, preferably 2.8, and the CPD content is measured at the end of the 2 week period. Thus, a solution containing polyamine-epihalohydrin resin according to the present invention will be storage stable if it contains less than about 250 ppm dry basis of CPD when measured at the end of the two week period, more preferably less than about 150 ppm dry basis of CPD when measured at the end of the 2 week period, more preferably less than about 75 ppm dry basis of CPD when measured at the end of the 2 week period, even more preferably less than about 40 ppm dry basis of CPD when measured at the end of the two week period, and even more preferably less than about 10 ppm dry basis of CPD when measured at the end of the 2 week period.

The resin solution stability test can be performed on solutions containing varying percent resin solids content; however, the CPD produced should be corrected for solids content. For example, for a 15 wt % resin solids content solution having a measured CPD content of 15 ppm, the corrected CPD, on a dry basis, will be 100 ppm dry basis (15 ppm/0.15 weight resin solids content).

The resin solution stability test is performed by charging a portion of the polyamine-epihalohydrin resin into a container containing a stirrer. The container is placed in a 50° C. water bath and maintained at 50° C. with stirring. An aliquot is removed from the container and submitted for GC (gas chromatography) analysis according to the GC procedure as set forth below. Typically, a flame ionization detector (FID) is first used to analyze the sample. An electrolytic conductivity detector (ELCD) or a halogen-specific detector (XSD) is used when increased sensitivity is needed, especially at less than about 20 ppm of the species to be analyzed. Other sensitive detectors can be used, e.g., electron capture detectors. This test is an accelerated aging test to model aging at longer periods of time at about 32° C.

An additional test to determine storage stability of resin solutions according to the present invention is the following test ("Acid Test"): A portion of resin to be tested is charged into a container containing a stirrer. The pH is adjusted to 1.0 with 96 wt % sulfuric acid. The container is closed and placed in a 50° C. water bath and maintained at 50° C. with stirring. An aliquot is removed from the container at 24 hours, and submitted for GC analysis in the manner described below to provide an indication of the storage stability.

The acid test can be performed on solutions containing varying percent resin solids content; however, the CPD produced should be corrected for solids content. For example, for a 15 wt % resin solids content solution having a measured CPD content of 15 ppm, the corrected CPD, on a dry basis, will be 100 ppm dry basis (15 ppm/0.15 weight resin solids content).

For the embodiment of the invention where the enzyme treatment is applied to the resins in a resin synthesis process without need for further treatment, although further treatment can be used, the amount of CPD release and/or produced by the resin, when stored at pH 1 for 24 hours at 50° C. and measured at 24 hours, releases and/or produces less than about 1000 ppm dry basis of CPD, more preferably releases and/or produces less than about 750 ppm dry basis of CPD, even more preferably releases and/or produces less than about 500 ppm dry basis of CPD, even more preferably releases and/or produces less than about 250 ppm dry basis of CPD, even more preferably releases and/or produces less than about 200 ppm dry basis of CPD, even more preferably releases and/or produces less than about 150 ppm dry basis of CPD, even more preferably releases and/or produces less than about 100 ppm dry basis of CPD, even more preferably releases and/or produces less than about 75 ppm dry basis of CPD, even more preferably releases and/or produces less than about 50 ppm dry basis of CPD, even more preferably releases and/or produces less than about 25 ppm dry basis of CPD, even more preferably releases and/or produces less than about 15 ppm dry basis of CPD, even more preferably releases and/or produces less than about 5 ppm dry basis of CPD, and even more preferably releases and/or produces less than about 3 ppm dry basis of CPD, and even more preferably releases and/or produces less than about 1 ppm dry basis of CPD.

For the embodiment of the invention where the enzyme treatment is simultaneously with, prior to or subsequent to an additional treatment to reduce at least one of epihalohydrins, epihalohydrin byproducts and organic halogen bound to the polymer backbone this additional treatment can be, but is not limited to, contacting the reduced CPD-forming resin with at least one microorganism, or at least one enzyme isolated from the at least one microorganism, in an amount, and at a pH and temperature effective to dehalogenate residual quantities of organically bound halogen, when stored at pH 1 for 24 hours at 50° C. and measured at 24 hours, contains less than about 1000 ppm dry basis of CPD, more preferably contains less than about 750 ppm dry basis of CPD, even more contains less than about 500 ppm dry basis of CPD, even more preferably contains less than about 250 ppm dry basis of CPD, even more preferably contains less than about 200 ppm dry basis of CPD, even more preferably contains less than about 150 ppm dry basis of CPD, even more preferably contains less than about 100 ppm dry basis of CPD, even more preferably contains less than about 75 ppm dry basis of CPD, even more preferably contains less than about 50 ppm dry basis of CPD, even more preferably contains less than about 25 ppm dry basis of CPD, even more contains less than about 15 ppm dry basis of CPD, even more preferably contains less than about 5 ppm dry basis of CPD, and even more preferably contains less than about 3 ppm dry basis of CPD, and even more preferably contains less than about 1 ppm dry basis of CPD.

GC Procedure and Instrumentation: GC was used to determine epi and epi by-products in the treated and untreated resins using the following method. The resin sample was absorbed onto an Extrelut column (available from EM Science, Extrelut QE, Part #901003-1) and extracted by passing ethyl acetate through the column. A portion of the ethyl acetate solution was chromatographed on a wide-bore capillary column. If flame ionization detector (FID) was used, the components are quantitated using n-octanol as the internal standard. If an electrolytic conductivity (ELCD) detector or if the halogen-specific (XSD) detector was used, an external standard method using peak matching quantitation was employed. The data system was either a Millennium 2010 or HP ChemStation. The FID detector was purchased from Hewlett-Packard (HP) as part of a Model 5890 GC. The ELCD detector, Model 5220, was purchased from OI Analytical. The XSD detector was purchased from OI Analytical, Model 5360 XSD. The GC instrument used was a HP Model 5890 series II. The column was DB-WAX (Megabore, J&W Scientific, Inc.) 30 m×0.53 mm with 1.5 micron film thickness. For the FID and ELCD, the carrier gas was helium with a flow rate of 10 mL/min. The oven program was 35° C. for 7 minutes, followed by ramping at 8° C./min to 200° C. and holding at 200° C. for minutes. The FID used hydrogen at 30 mL/min and air at 400 mL/min at 250° C. The ELCD used n-propanol as the electrolyte with an electrolyte flow rate setting of 50% with a reactor temperature of 900° C. The XSD reactor was operated in an oxidative mode at 1100° C. with a high purity air flow rate of 25 mL/min.

Moreover, paper products containing resins according to the present invention are capable of being stored without undue formation of CPD. Thus, paper products according to the present invention can have initial low levels of CPD, and can maintain low levels of CPD over an extended period storage time. More specifically, paper products according to the present invention, made with a 1 wt % addition level of resin, will contain less than about 250 parts per billion (ppb) of CPD, more preferably less than about 100 ppb of CPD, even more preferably less than about 50 ppb of CPD and even more preferably less than about 10 ppb of CPD, and even more preferably less than about 1 ppb of CPD when stored for periods as long as 2 weeks, preferably as long as at least 6 months, and even more preferably as long as at least one year. Moreover, paper products according to the present invention, made with about a 1 wt % addition level of resin, will have an increase in CPD content of less than about 250 ppb, more preferably less than about 100 ppb of CPD, even more preferably less than about 50 ppb of CPD, even more preferably less than about 10 ppb of CPD, and even more preferably less than about 1 ppb of CPD when stored for periods as long as 2 weeks, more preferably as long as at least 6 months, and even more preferably as long as at least one year. In other words, the paper products according to the present invention have storage stability and will not generate excessive CPD content in paper products when the paper products are stored as little as one day and for periods of time greater than one year. Thus, the resins according to the present invention give minimal formation of CPD in paper products, particularly those exposed to aqueous environments, especially hot aqueous environments, e.g., tea bag, coffee filters, etc. Further examples of paper products include packaging board grade, and tissue and towel grade.

Paper can be made by adding the resin at addition levels other than about 1 wt %; however, the CPD content should be corrected for the addition level. For example, for a paper product made by adding the resin at a 0.5 wt % addition level having a measured CPD content of 50 ppb, the corrected CPD on a 1 wt % addition level basis will be 100 ppb (50 ppb/0.5 percent addition level).

To measure CPD in paper products, the paper product is extracted with water according to the method described in European standard EN 647, dated October 1993. Then 5.80 grams of sodium chloride is dissolved into 20 ml of the water extract. The salted aqueous extract is transferred to a 20 gram capacity Extrelut column and allowed to saturate the column for 15 minutes. After three washes of 3 ml ethyl acetate and saturation of the column, the Extrelut column is eluted until 300 ml of eluent has been recovered in about 1 hour. The 300 ml of ethyl acetate extract is concentrated to about 5 ml using a 500-ml Kuderna-Danish concentrating apparatus (if necessary, further concentrating is done by using a micro Kuderna-Danish apparatus). The concentrated extract is analyzed by GC using the procedure and instrumentation described above. Typically, an electrolytic conductivity detector (ELCD) or a halogen-specific detector (XSD) is used. Other sensitive detectors can be used, e.g., electron capture detectors. Alternatively, CPD in paper products can be measured using the procedure described in Example 4.

The resins that can be treated with enzymatic agent according to the present invention can comprise any polyamine-epihalohydrin resins. This invention is also directed towards the preparation, use and treatment of polyamine-epihalohydrin resins, such as polyaminopolyamide-epichlorohydrin resins, made by reacting epihalohydrin, such as epichlorohydrin, with a prepolymer (also interchangeably referred to herein as polymer), such as polyaminoamide prepolymer. In the case of polyaminopolyamide resins, it is noted that the polyaminoamide prepolymer is also referred to as polyamidoamine, polyaminopolyamide, polyamidopolyamine, polyamidepolyamine, polyamide, basic polyamide, cationic polyamide, aminopolyamide, amidopolyamine or polyaminamide.

A preferred group of polymers for use in the present invention includes cationic polymers, alone or together with other polymers. Particularly preferred cationic polymers include those used for the purpose of imparting wet strength to paper as well as creping agents. A listing of many polymers useful in papermaking formulations, such as wet strength and creping agents, is described in Paper Chemistry, ISBN 0-216-92909-1, pages 78-96, published in the USA by Chapman Hall, New York. Chapter 6 of this book is entitled "Wet Strength Chemistry", and is hereby incorporated, in its entirety, by reference thereto. Chapter 6 describes several classes of polymers which are used to impart wet strength to paper, including: polyaminoamide-epichlorohydrin resin, urea-formaldehyde resin, melamine-formaldehyde resin, epoxidized polyamide resin, glyoxalated polyacrylamide resin, polyethyleneimine resin, dialdehyde starch, proteinaceous adhesive treated with formaldehyde, cellulose xanthate (viscose), synthetic latex, vegetable gum, and glyoxal. The polyaminoamide-epichlorohydrin resin may be a Kymene® brand polyaminoamide-epichlorohydrin resin, such as Kymene® 557LX, Kymene® SLX2, or Kymene® 617, or a polyamine-epichlorohydrin resin such as Kymene® 2064, Kymene® 367 resins, and Kymene® 736 or polyamide-polyurylene-epihalohydrin resins such as Kymene® 450.

The invention is directed to cationic polymers such as polyamine-epichlorohydrin resins which may be used alone or in combination with other polymers used for the wet strengthening of paper and creping agents. These resins include epichlorohydrin resins and nitrogen-containing cationic polymers, both of which are derived from epichlorohydrin reactants. Preferred resins for the purposes of this invention include polyaminoamide-epichlorohydrin wet-strength resins as described in U.S. Pat. Nos. 2,926,154; 3,332,901; 3,891,589; 3,197,427; 4,240,935; 4,857,586; European Patent Publication 0,349,935, and Great Britain Patent 865,727, and U.S. patent application Ser. Nos. 09/629,629, 09/592,681, 09/363,224 and 09/330,200. Further, resins include Crepetrol® 80E or Crepetrol® A3025, Crepetrol® A6115, Crepetrolt A8225, Crepetrol® 870, SPC 003, and Rezosol® 8289 creping agents, which are available from Hercules Incorporated, Wilmington, Del. It is noted that these resins are generally referred to herein as polyamine-epihalohydrin resins, and such resins include, but are not limited to, polyaminopolyamide-epihalohydrin resins (which are also known as polyaminoamide-epihalohydrin resins, polyamidepolyamine-epihalohydrin resins, polyaminepolyamide-epihalohydrin resins, aminopolyamide-epihalohydrin resins, polyamide-epihalohydrin resins); polyalkylene polyamine-epihalohydrin; and polyaminourylene-epihalohydrin resins, copolyamide-polyurylene-epihalohydrin resins, polyamide-polyurylene-epihalohydrin resins, with the epihalohydrin preferably being epichlorohydrin in each instance. Processes for making these known resins are also disclosed in these documents, which are incorporated in their entireties, by reference thereto.

Exemplary epichlorohydrin resins in these patents are characterized by the presence of N-chlorohydrin groups of the formula:

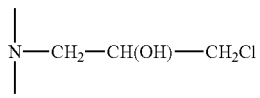

and quaternary N-chlorohydrin groups of the formula:

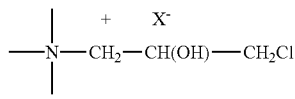

Wherein the tetrasubstituted nitrogen atom is positively charged (a quaternary nitrogen), and hence cationic;

and isomeric 3-hydroxyazetidinium chloride groups of the formula:

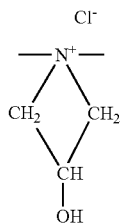

A preferred cationic polymer utilized in the present invention is a polymer having the following formula:

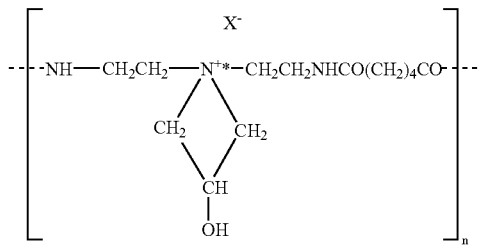

where the asterisked tetrasubstituted nitrogen atom is positively charged (a quaternary nitrogen), and hence cationic. The nitrogen atom is in a 4-membered ring (i.e. a 3-hydroxyazetidinium group). Other uncharged polymer units also co-exist along polymer chains of this type of resin. Even though a few negatively charged (i.e., anionic) groups may also be present on the polymer, the net charge along the polymer chain is positive. $X^-$ is a simple anion, which is not covalently bonded to the polymer chain. Generally the anion is a chloride ion, and n is an integer of from about 5 to several thousand, preferably 5 to 3000.

Creping agents include, without limitation, Crepetrol® 80E or Crepetrol® A3025, Crepetrol® A6115, Crepetrol® A8225, Crepetrol® 870, SPC 003, and Rezosol® 8289 creping agents.

For wet strength agents, while ratios greater than 1 can be utilized, it is preferred that the resin comprise a resin formed in a polyamide-epihalohydrin reaction having a molar ratio of epihalohydrin to secondary amine group of less than 1, more preferably the molar ratio of epihalohydrin to secondary amine group is less than about 0.975, with a preferred range of the molar ratio of epihalohydrin to secondary amine group being about 0.5 to 0.975, more preferably the molar ratio of epihalohydrin to secondary amine group being about 0.6 to 0.975, and even more preferably about 0.8 to 0.975. For creping agents, it is preferred that the resin comprise a resin formed in a polyamide-epihalohydrin reaction having a molar ratio of epihalohydrin to secondary amine group of less than about 0.50, more preferably less than about 0.25, and can even be lower than 0.1, with a preferred lower limit of about 0.05.

Moreover, creping agents according to the present invention do not need as much crosslinking functionalities as wet strength agents, and can therefore have a lower azetidinium level than wet strength agents. Thus, preferably the azetidinium level of creping agents is less than about 10 mole %, with a preferred range of about 5 to 10 mole %, and preferably the azetidinium level of wet strength agents is greater than about 30 mole %, with a preferred range of about 30 to 70 mole %. The mole % azetidinium and the mole % of other species can be determined by the following NMR Procedure.

NMR Procedure:

The $^{13}C$ NMR spectra are acquired using BRUKER AMX spectrometers equipped with a 10 mm broadband probe. A $^{13}C$ NMR operating frequency of 100 MHz (AMX400) or 125 MHz (AMX500) is sufficient for data collection. In either case, the spectra are acquired with continuous $^1H$ decoupling. Electronic integration of the appropriate signals provides molar concentrations of the following alkylation components; ACH, EPX, GLY, and AZE.

where: ACH=polymeric aminochlorohydrins, EPX=polymeric epoxides, GLY=polymeric glycols, AZE=azetidinium ions In order to calculate the concentrations of each of these species, the integral values must be placed on a one (1) carbon basis. For example, the spectral region between 20-42 ppm represents six (6) carbons of the diethylenetriamine-adipate backbone, hence the integral value is divided by six. This value is used as the polymer common denominator (PCD) for calculation of the alkylation species. The chemical shifts of these species are provided below (using an acetonitrile field reference of 1.3 ppm). The corresponding integral value of each alkylation product is used in the numerator for calculation, refer to examples below:

ACH signal at 68-69 ppm represents one carbon; integral of ACH÷PCD=mole fraction ACH GLY signal at 69-70 ppm represents one carbon; integral of GLY÷PCD=mole fraction GLY EPX carbon at 51-52 ppm represents one carbon; integral of EPX÷PCD=mole fraction EPX AZE signal at 73-74 ppm represents two carbons, thus, a division factor of two is required; integral of AZE/2÷PCD=mole fraction AZE The following spectral parameters are standard experimental conditions for $^{13}$C NMR analysis of Kymene resins or creping agents on the Bruker AMX400.

| | |
|---|---|
| Temperature | 25 C. |
| Resonance Frequency | 100 MHz |
| # Data Points | 64K |
| Dwell Time | 20 microseconds |
| Acquisition Time | 1.3 seconds |
| Sweep Width | 25000 Hz |
| Number of Scans | 1K |
| Relaxation Delay | 3 seconds |
| Pulse Tip Angle | 70 degrees |
| Pulse Program | zgdc |
| Processed Spectral Size | 64K |
| Apodization Function | exponential |
| Line Broadening | 3 Hz |

Moreover according to the present invention, for creping agents derived from prepolymers containing tertiary amine functionality, the creping agent will preferably have a quaternary aminohalohydrin, e.g., aminochlorohydrin, content of less than about 30 mole %, while wet strength agents according to the present invention preferably have a quaternary aminohalohydrin, e.g., aminochlorohydrin, content of greater than 30 mole %. Moreover, without wishing to be bound by theory, it is believed that secondary amine compounds, such as diethylenetriamine, form azetidinium groups, whereas, tertiary amine type compounds, such as methylbis(3-aminopropyl)amine, form quaternary aminochlorohydrin groups. Examples of tertiary amine type compounds include, but are not limited, the reaction product of adipic acid and a methylbis(3-aminopropyl)amine, result in a tertiary amine prepolymer. This prepolymer is used to make a tertiary amine based resin which contains quaternary aminohalohydrin groups.

Preferred polyamines for this invention are produced by reacting a dicarboxylic acid, or a derivative thereof, with methyl bis(3-aminopropyl) amine or with a polyalkylenepolyamine containing from two to four alkylene groups having two to four carbons, two primary amine groups, and one to three secondary amine groups. Dicarboxylic acid derivatives suitable for preparing the polyaminoamides include esters, anhydrides and acid halides.

Procedures for preparing polyaminoamides from polyalkylenepolyamines are described in U.S. Pat. No. 2,926,154, to Keim, which is incorporated herein by reference in its entirety. Procedures utilizing methyl bis(3-aminopropyl) amine for preparation of polyaminoamides are described in U.S. Pat. No. 5,338,807 to Espy et al. and U.S. Pat. No. 5,994,449, which are incorporated by reference herein in their entireties.

Expanding upon the above, polyaminopolyamide-epichlorohydrin resins comprise the water-soluble polymeric reaction product of epichlorohydrin and polyamide derived from polyalkylene polyamine and saturated aliphatic dibasic carboxylic acid containing from about 2 to about 10 carbon atoms. It has been found that resins of this type impart wet-strength to paper whether made under acidic, alkaline or neutral conditions. Moreover, such resins are substantive to cellulosic fibers so that they may be economically applied thereto while the fibers are in dilute aqueous suspensions of the consistency used in paper mills.

In the preparation of the cationic resins contemplated for use herein, the dibasic carboxylic acid is first reacted with the polyalkylene polyamine, under conditions such as to produce a water-soluble polyamide containing the recurring groups

where n and x are each 2 or more and R is the divalent hydrocarbon radical of the dibasic carboxylic acid. This water soluble polyamide is then reacted with an epihalohydrin to form the water-soluble cationic resins. The dicarboxylic acids contemplated for use in preparing the resins of the invention are the saturated aliphatic dibasic carboxylic acids containing from 2 to 10 carbon atoms such as oxalic acid, malonic acid, succinic acid, glutaric acid, adipic acid, azelaic acid and the like. The saturated dibasic acids having from 4 to 8 carbon atoms in the molecule, such as adipic and glutaric acids are preferred. Blends of two or more of the saturated dibasic carboxylic acids may also be used. Derivatives of dibasic carboxylic acids, such as esters, half-esters and anhydrides can also be used in the present invention, such as dimethyl adipate, diethyl adipate, dimethyl glutarate, diethyl glutarate, dimethyl succinate and diethyl succinate. Blends of two or more of derivatives of dibasic carboxylic acids may also be used, as well as blends of one or more derivatives of dibasic carboxylic acids with dibasic carboxylic acids.

A variety of polyalkylene polyamines including polyethylene polyamines, polypropylene polyamines, polybutylene polyamines, polypentylene polyamines, polyhexylene polyamines and so on and their mixtures may be employed of which the polyethylene polyamines represent an economically preferred class. More specifically, the polyalkylene polyamines contemplated for use may be represented as polyamines in which the nitrogen atoms are linked together by groups of the formula $-C_nH_{2n}-$ where n is a small integer greater than unity and the number of such groups in the molecule ranges from two up to about eight. The nitrogen atoms may be attached to adjacent carbon atoms in the group $-C_nH_{2n}-$ or to carbon atoms further apart, but not to the same carbon atom. This invention contemplates not only the use of such polyamines as diethylenetriamine, triethylenetetramine, tetraethylenepentamine and dipropylenetriamine, which can be obtained in reasonably pure form, but also mixtures and various crude polyamine materials. For example, the mixture of polyethylene polyamines obtained by the reaction of ammonia and ethylene dichloride, refined only to the extent of removal of chlorides, water, excess ammonia, and ethylenediamine, is a satisfactory starting material. The term "polyalkylene polyamine" employed in the claims, therefore, refers to and includes any of the polyalkylene polyamines referred to above or to a mixture of such polyalkylene polyamines and derivatives thereof. Additional polyamines that are suitable for the present invention include; bis-hexamethylenetriamine (BHMT), methylbisaminopropylamine (MBAPA), other polyalkylene polyamines (e.g., spermine, spermidine). Preferably, the polyamines are diethylenetriamine, triethylenetetramine, tetraethylenepentamine and dipropylenetriamine.

It is desirable, in some cases, to increase the spacing of secondary amino groups on the polyamide molecule in order to change the reactivity of the polyamide-epichlorohydrin complex. This can be accomplished by substituting a diamine such as ethylenediamine, propylenediamine, hexamethylenediamine and the like for a portion of the polyalkylene polyamine. For this purpose, up to about 80% of the polyalkylene polyamine may be replaced by molecularly equivalent amount of the diamine. Usually, a replacement of about 50% or less will serve the purpose.

Appropriate aminocarboxylic acids containing at least three carbon atoms or lactams thereof are also suitable for use to increase spacing in the present invention. For example, 6-aminohexanoic acid and caprolactam.

Polyaminoureylene-epihalohydrin resins, particularly polyaminoureylene-epichlorohydrin resins, are also contemplated in the present invention, such as discussed in U.S. Pat. Nos. 4,487,884 and 3,311,594, which are incorporated by reference in their entireties, such as Kymene®450 type of resins (Hercules Incorporated, Wilmington, Del.). The polyaminoureylene resins contemplated for preparation and use herein are prepared by reacting epichlorohydrin with polyaminoureylenes containing free amine groups. These polyaminoureylenes are water-soluble materials containing tertiary amine groups and/or mixtures of tertiary amine groups with primary and/or secondary amino groups and/or quaternary ammonium groups. However, tertiary amino groups should account for at least 70% of the basic nitrogen groups present in the polyaminoureylene. These polyaminoureylenes may be prepared by reacting urea or thiourea with a polyamine containing at least three amino groups, at least one of which is a tertiary amino group. The reaction can, if desired, be carried out in a suitable solvent such as xylene.

The polyamine reactant should preferably have at least three amino groups, at least one of which is a tertiary amino group. The polyamine reactant may also have secondary amino groups in limited amounts. Typical polyamines of this type suitable for use as hereinabove described are methyl bis(3-aminopropyl)amine (MBAPA), methyl bis(2-aminoethyl)amine, N-(2-aminoethyl)piperazine, 4,7-dimethyltriethylenetetramine and so on, which can be obtained in reasonably pure form, but also mixtures of various crude polyamine materials.

To prepare the prepolymer from diacid and polyalkylenepolyamine, a mixture of the reactants is preferably heated at a temperature of about 125-200° C. for preferably about 0.5 to 4 hours, at atmospheric pressure. Where a reduced pressure is employed, lower temperatures such as 75° C. to 150° C. may be utilized. This polycondensation reaction produces water as a byproduct, which is removed by distillation. At the end of this reaction, the resulting product is dissolved in water at a concentration of about 50% by weight total polymer solids.

Where diester is used instead of diacid, the prepolymerization can be conducted at a lower temperature, preferably about 100-175° C. at atmospheric pressure. In this case the byproduct will be an alcohol, the type of alcohol depending upon the identity of the diester. For instance, where a dimethyl ester is employed the alcohol byproduct will be methanol, while ethanol will be the byproduct obtained from a diethyl ester. Where a reduced pressure is employed, lower temperatures such as 75° C. to 150° C. may be utilized.

In converting the polyamide, formed as above described, to a cationic resin, it is reacted with epichlorohydrin at a temperature from above about 0° C., more preferably about 25° C., to about 100° C., and preferably between about 35° C. to about 70° C. until the viscosity of a 20% solids solution at 25° C. has reached about C or higher on the Gardner Holdt scale. This reaction is preferably carried out in aqueous solution to moderate the reaction. Although not necessary, pH adjustment can be done to increase or decrease the rate of crosslinking.

When the desired viscosity is reached, sufficient water can be added to adjust the solids content of the resin solution to the desired amount, i.e., about 15 wt % more or less, the product can be cooled to about 25° C. and then stabilized to permit storage by improving the gelation stability by adding sufficient acid to reduce the pH to less than about 6, preferably less than about 5, and most preferably less than about 4. Any suitable inorganic or organic acid such as hydrochloric acid, sulfuric acid, methanesulfonic acid, nitric acid, formic acid, phosphoric acid and acetic acid may be used to stabilize the product. Non-halogen containing acids, such as sulfuric acid, are preferred.

Fibrous webs are creped using the compositions of this invention by: (1) applying the composition described above to a drying surface for the web or to the web; (2) pressing the fibrous web against the drying surface to effect adhesion of the web to the drying surface; and (3) dislodging the web from the drying surfaces with a creping device such as a doctor blade to crepe the fibrous web. Preferably, in step (1), the composition is applied to the drying surface for the web. The preferred fibrous web is a cellulosic web.

Preferably the creping adhesive is applied in aqueous solution containing from about 0.1 to about 10 weight percent of the resin composition. More preferably, the resin composition is in solution at the level of about 0.25 to about 5 weight percent, and most preferably at about 0.5 to about 2 weight percent. For creping agents on a dry weight basis, a minimum amount of about 0.001 weight percent based on the dry weight of the pulp or paper is used. A more preferable minimum amount is about 0.005 weight percent, and the most preferable minimum amount is about 0.01 weight percent. The preferable maximum amount of resin composition is about 2 weight percent. A more preferable maximum is about 1 weight percent, and the most preferable maximum about 0.5 weight percent. The drying surface most commonly used in commercial operations is a Yankee dryer, and the aqueous solution of adhesive will most often be applied to the creping cylinder or drum by spraying. Alternatively, however, it can be added by application to the fibrous web, preferably by spraying. In the case of cellulose webs, i.e. paper, the creping adhesive can be added at the wet end of the paper machine by application to the wet web. In some situations it may be possible to add the creping adhesive to the pulp before formation of the sheet.

Other ingredients, in particular, agents which modify adhesion of the web to the drying surface, can used in conjunction with the creping adhesives of this invention. Such agents, also know as release agents or plasticizers, include water soluble polyols, glycols, polyethylene glycols, sugars, oligosaccharides and hydrocarbon oils.

The process for making paper utilizing the resin compositions of this invention comprises: (a) providing an aqueous pulp suspension; (b) adding to the aqueous pulp suspension the resin and (c) sheeting and drying the aqueous pulp suspension produced in (b) to obtain paper.

The aqueous pulp suspension of step (a) of the process is obtained by means well known in the art, such as known mechanical, chemical and semichemical, etc., pulping processes. Normally, after the mechanical grinding and/or chemical pulping step, the pulp is washed to remove residual pulping chemicals and solubilized wood components. Either bleached or unbleached pulp fiber may be utilized in the process of this invention. Recycled pulp fibers are also suitable for use.

In step (b), resin of this invention preferably is added to pulp slurry in a minimum amount of about 0.1 weight percent based on the dry weight of the pulp. A more preferable minimum amount is about 0.2 weight percent. The preferable maximum amount of resin composition is about 5 weight percent. A more preferable maximum is about 3 weight percent, and the most preferable maximum about 1.5 weight percent. The resin composition is generally added in the form of an aqueous solution. In addition to the resin, other materials normally used in paper may be added as well. These include, for example, sizing agents, pigments, alum, brightening agents, dyes and dry strength agents, added in amounts well known in the art.

Step (c) is carried out according to procedures well known to those skilled in the art of papermaking.

As discussed above, resins having at least reduced levels of formation of CPD can be resins as produced in a resin synthesis process without further treatment. Moreover, the resins can be treated by various processes prior to reduction and/or removal of the CPD-forming species. Still further, after treatment to reduce and/or remove CPD-forming species, the resin can be treated by various processes. Yet still further, the resin can be treated by various processes prior to reduction and/or removal of the CPD-forming species, and the resin can also be treated by various processes after treatment to reduce and/or remove CPD-forming species. For example, the resin can be treated by various processes, such as processes to remove low molecular weight epihalohydrin and epihalohydrin by-products, e.g., epichlorohydrin and epichlorohydrin by-products, for example, CPD in the resin solution. Without limiting the treatments or resins that can be utilized, it is noted that resins, such as Kymene® SLX2, Kymene® 1617 and Kymene® 557LX (available from Hercules Incorporated, Wilmington, Del.), and Crepetrol® 80E or Crepetrol® A3025, Crepetrol® A6115, Crepetrol® A8225, Crepetrol® T 870, SPC 003, and Rezosol® 8289 creping agents could be treated prior to and/or subsequent to reduction or removal of CPD-forming species with a base ion exchange column, such as disclosed in U.S. Pat. No. 5,516,885 and WO 92/22601; with carbon adsorption, such as disclosed in WO 93/21384; membrane separation, e.g., ultrafiltration; extraction, e.g, ethyl acetate, such as disclosed in U.S. Statutory Invention Registration H1613; or biodehalogenation, such as disclosed in U.S. Pat. No. 5,972,691, WO 96/40967 and U.S. Pat. Nos. 5,470,742, 5,843,763 and 5,871,616, as well as U.S. application Ser. No. 09/629,629. The disclosures of each of these documents is incorporated by reference in their entireties. Moreover, any combination of CPD-forming species reduction or removal as disclosed in the above-noted U.S. patent application Ser. Nos. 09/592,681, 09/363,224, and 09/330,200, each of which is incorporated by reference in its entirety, can be utilized with the enzymatic treatment for reduction and/or removal of CPD-forming species.

Still further, in accordance with the present invention, it is further noted that the enzymatic treatment to remove or reduce CPD-forming species can be performed in an overlapping manner with biodehalogenation, or can be performed simultaneously with the biodehalogenation. Thus, the present invention also relates to a combined process in which both enzymatic release of 3-CPD from resins is started, and simultaneously reduction of nitrogen-free organohalogen compounds occurs.

It is further noted that, in addition to the enzymatic treatment followed by the biodehalogenation treatment, the two treatments can be done simultaneously (aka combined treatment). "Simultaneously" meaning the second treatment (either biodehalogenation or enzymatic) can be started before the first treatment (either biodehalogenation or enzymatic) is completed. For the present invention, the desired viscosity is obtained by balancing the conditions of time, temperature, pH, enzyme concentration, starting viscosity, and solids content. For example, the combined treatment can be started at pH 6.8-7.8 for the first 4-24 hours and than lowered to pH of 5.5-7.0 or the pH can be allowed to drift down to 6.5-7.2 for the latter 8-48 hours of the combined treatment. Preferred combined treatment conditions include, but are not limited to, pH 6.5 to 8.0, more preferably pH 6.8 to 7.6; preferred temperature range of 20° C. to 35° C., more preferably 25° C. to 33° C. Enzyme concentrations for combined treatment conditions will depend upon its activity. For example, in the case of ALCALASE, the enzyme can be present in an amount of about 1 g of ALCALASE 2.5L type DX (as received) to 1600 g polyamine-epichlorohydrin resin (dry basis) to 1 g of ALCALASE 2.5L type DX (as received) to 1.5 g polyamine-epichlorohydrin resin (dry basis), also the enzyme can be present in an amount of about 1 g of ALCALASE 2.5L type DX (as received) to 160 g polyamine-epichlorohydrin resin (dry basis) to 1 g of ALCALASE 2.5L type DX (as received) to 4 g polyamine-epichlorohydrin resin (dry basis). It is preferred that the combined treatment, is completed in 48 hours or less. It is more preferred that the combined treatment is completed in 24 hours or less. For creping aids, the solids level when using the combined treatment conditions can be lower than 15 weight percent, typically 4-14.5 weight percent % and preferably from about 8 wt % to about 14.5 wt %. The combined treatment for creping aids can also be done at solid level of 15 wt % and above, the preferred total solids levels are 15 to 40 weight percent, preferably 18-35 weight percent and even more preferably 18-28 weight percent. An additional range that can be used in the present invention is 15-30 weight percent.

The preferred total solids level when using the combined treatment conditions for wet strength resins with 15 wt percent or higher is 15-40 weight percent, preferably 16-35 weight percent and even more preferably 18-28 weight percent. When doing the combined treatment of wet strength resins with less than 15 wt percent the preferred ranges are from about 4 wt % to about 14.5 weight % and from about 8 wt % to about 14.5 wt %.

Still further, the present invention enables biodehalogenation at high total solids content, as well as combined enzymatic treatment to remove or reduce CPD-forming species and biodehalogenation at high total solids content, with the possibility to reduce process cycle time, and at the same time creating an optimized reactor volume usage when running the process in batch or (repeated) fedbatch mode.

Biodehalogenation can be achieved in various manners, such as disclosed in any one of U.S. Pat. Nos. 5,470,742; 5,843,763 and 5,871,616, and U.S. application Ser. No. 09/629,629, or previous base treatment and biodehalogenation as disclosed in U.S. Pat. No. 5,972,691, and WO 96/40967, with or without a previous inorganic base treatment, wherein the resin composition may be reacted with a microorganism or enzyme in adequate quantities to process epihalohydrin hydrolyzates to very low levels. Microorganisms use dehalogenase enzymes to liberate halide ion from the epihalohydrin and haloalcohol and then use further enzymes to break down the reaction products ultimately to carbon dioxide and water.

While not wishing to be bound by theory, it is noted that when the CPD-forming species is removed or reduced, CPD is released from the oligomeric and/or polymeric component of the resin, and therefore CPD is a component of the resin solution. With this in mind, the resin is preferably subjected to treatment to remove or reduce the CPD-forming species, and then the resin is biodehalogenated. In this manner, epihalohydrin and epihalohydrin hydrolyzate (also referred to as hydrolysis by-products), including released CPD, can be removed, such as by the biodehalogenation. However, the resin can be initially treated, such as by biodehalogenation, and then subjected to treatment to remove, inhibit and/or reduce the CPD-forming species. In particular, any CPD that will be released by the treatment should be readily soluble, and can therefore be at least partially washed away from the resin. For example, when the resin with released CPD is included in a paper product, the CPD can be at least partially washed out of the paper product, and, due to the treatment, the resin in the paper product will not produce CPD or will not produce undesirable amounts of CPD. Moreover, as discussed above, the enzymatic treatment to remove or reduce CPD-forming species can be performed in an overlapping/simultaneous manner with the biodehalogenation.

The biocatalyst may be provided in the form of either living cells or as an immobilized, unrefined cell-free extract or refined dehalogenase. The term "biodehalogenation" refers to the dehalogenation of a nitrogen-free organohalogen compound using a biocatalyst.

As the biocatalyst capable of biodehalogenation, there can be utilized any microorganism that is capable of dehalogenating nitrogen-free organohalogen compounds, preferably CPD and DCP, while leaving nitrogen-containing cationic polymers substantially intact during the dehalogenation of the nitrogen-free organohalogen compounds. Preferably, the microorganisms utilized are *Agrobacterium radiobacter* (HK7) or *Arthrobacter histidinolovorans* (HK1), and preferably there is utilized a two-component mixture of *Agrobacterium radiobacter* (HK7) and *Arthrobacter histidinolovorans* (HK1). When only CPD is present, it is preferred to use a single microorganism, HK1. When only DCP is present, it is preferred to use a single microorganism, HK7. Although the precise identity of the enzymes which make the method operable has not been made, it is believed that the enzymes which effectuate the method belong to the class of enzymes termed "hydrogen halide lyase type dehalogenase".

In particular, a number of bacterial strains are disclosed in U.S. Pat. Nos. 5,470,742, 5,843,763, 5,871,616, and 5,972,691, and U.S. application Ser. No. 09/629,629, the disclosures of which are incorporated by reference herein in their entireties. These bacterial strains include microorganisms which contain dehalogenating enzymes capable of dehalogenating haloalcohols and epihalohydrins deposited under NCIMB Deposit Accession Nos. 40271, 40272, 40273, 40274, 40313 and 40383. NCIMB stands for "National Collection of Industrial and Marine Bacteria". NCIMB, located at 23 St. Machar Drive, Aberdeen AB2 1RY, Scotland, UK is an organization in the United Kingdom responsible for documenting and retaining samples of bacteria submitted for patent application purposes. In patent matters, NCIMB will supply to interested parties who so request, authentic samples of bacteria claimed in patent literature. NCIMB 40271 (Arthrobacter species), 40272 (*Agrobacterium radiobacter* HK7), 40273 (*Burkholderia cepacia* formerly known as *Pseudomonas cepacia*), and 40274 (*Arthrobacter histidinolovorans* HK1) were deposited on Apr. 2, 1990. NCIMB 40383 (Rhodococcus species) was deposited on Mar. 11, 1991, and NCIMB 40313 (*Burkholderia cepacia* formerly known as *Pseudomonas cepacia*), was desposited on Aug. 30, 1990. Thus, the microorganisms have been filed in a depository under the provisions of the Budapest Treaty, and the strains will be irrevocably and without restriction or condition released to the public upon the issuance of a patent.

Still further, it is noted that two bacterial strains, which were isolated from soil samples and the consortium designated HKC, are preferably used, i.e., *Arthrobacter histidinolovorans* (HK1) which was deposited with the Centraalbureau voor Schirnmelcultures at Oosterstraat 1, P.O. Box 273, 3740 AG BAARN, The Netherlands, as Accession Number CBS 108919 on Jul. 10, 2000, and *Agrobacterium radiobacter* (HK7) which was deposited with the Centraalbureau voor Schimmelcultures at Oosterstraat 1, P.O. Box 273, 3740 AG BAARN, The Netherlands, as Accession Number CBS 108920 on Jul. 10, 2000. In patent matters, Centraalbureau voor Schimmelcultures, which is a deposit, tory in conformance with the Budapest Treaty, will supply to interested parties, who so request, authentic samples of bacteria claimed in patent literature. Thus, the microorganisms have been filed in a depository under the provisions of the Budapest Treaty, and the strains will be irrevocably and without restriction or condition released to the public upon the issuance of a patent. It is noted that NCIMB 40272 and CBS 108920 are believed to be identical microorganisms, and that NCIMB 40274 and CBS 108919 are believed to be identical microorganisms.

Each of these microorganisms is capable of degrading both 1,3-DCP and 3-CPD. Moreover, the *Agrobacterium radiobacter* (HK7) is able to reduce 1,3-DCP levels faster than *Arthrobacter histidinolovorans* HK1, while *Arthrobacter histidinolovorans* (HK1) showed a preference for 3-CPD degradation. Thus, as disclosed in U.S. application Ser. No. 09/629,629, it is deemed that the best biodehalogenation performance is obtained when both bacteria were present. To ensure that both bacteria are present in the biodehalogenation process, it is preferred to start the process with *Agrobacterium radiobacter* (HK7) and to subsequently add the *Arthrobacter histidinolovorans* (HK1). This would especially be the situation for starting up a continuous biodehalogenation process.

The microorganisms containing suitable enzymes are used to dehalogenate the epihalohydrin hydrolyzates contained in the resin composition with or without an initial inorganic base treatment. The enzymes and microorganisms are maintained in a suitable concentration to substantially metabolize the hydrolyzates to chloride ion and ultimately carbon dioxide and water. Thus the concentration of hydrolyzates in the resin composition of the present invention after biodehalogenation treatment is preferably less than about 100 ppm (parts per million by weight relative to the total weight of aqueous solution containing resins after the bioreaction step), more preferably less than about 50 ppm (parts per million by weight relative to the total weight of aqueous solution containing resins after the bioreaction step), more preferably less than about 10 ppm (parts per million by weight relative to the total weight of aqueous solution containing resins after the bioreaction step), more preferably less than about 5 ppm (parts per million by weight relative to the total weight of aqueous solution containing resins after the bioreaction step), and even more preferably less than about 1 ppm (parts per million by weight relative to the total weight of aqueous solution containing resins after the bioreaction step).

To achieve this, the concentration of microorganisms should be at least about $5 \times 10^7$ cells/ml, preferably at least about $10^8$ cells/ml and most preferably at least about $10^9$ cells/ml. To maintain optimum active content of cells in the reactor, the reaction is best carried out at about 30° C.+/−5° C. in the presence of oxygen (e.g., from about 5 to about 100% DOT) and nutrients in a stirred tank reactor. As used herein, the term "DOT" refers to "dissolved oxygen tension" and is the amount of oxygen, expressed as a percentage, dissolved in a given volume of water relative to oxygen-saturated water at the same temperature and pressure. In a continuous process, the residence time is controlled by flow rate and monitored to ensure complete reaction. Thus, at steady state the concentration of epihalohydrin hydrolyzates in the reactor will be from about 1 to about 1000 ppm. In a batch or fedbatch mode, which can be preferably repeated, complete reaction can be ensured by monitoring, for example by GC analysis, to achieve the desired reduced level of epihalohydrin hydrolyzates.

The method of biodehalogenation in accordance with the present invention is carried out by contacting a microorganism or cell-free enzyme-containing extract with the aqueous composition containing the unwanted organohalogen contaminants. Such contact is typically achieved by forming a slurry or suspension of the microorganism or cell-free extract in the aqueous composition, with sufficient stirring.

If desired, the microorganism or enzymes can be removed from the product stream by filtration, sedimentation, centrifugation or other means known to those skilled in the art. Alternatively the microorganisms or enzymes can remain in the final product and optionally deactivated by thermal sterilization (e.g., by treatment at 140° C. for 20 seconds) or by the addition of a suitable concentration of a suitable biocidal agent. Suitable biocidal agents can be readily selected by those of ordinary skill in the art. Thus, deactivation of the microorganism can be performed by reducing the pH of the aqueous mixture to 2.8, then adding a proprietary biocidal agent (e.g. Proxell® BD biocidal agent, which comprises 1,2-benzisothiazolin-3-one) in sufficient quantity, normally 0.02% to 0.1%, based on the weight of the aqueous composition. The biocidal agent may be added along with potassium sorbate.

The removal of the microorganism may be performed by one or more of the steps of filtration, centrifugation, sedimentation, or any other known techniques for removing microbes from a mixture. The microorganisms mineralize the nitrogen-free organohalogen compounds, producing $CO_2$, water, and biomass, with no glycerol left in the resin. Where the biocatalyst is an immobilized dehalogenase, the product of the reaction is glycidol, which can be hydrolyzed to glycerol with an immobilized hydrolase.

A problem associated with the removal of the microbes from the mixture is that intensive methods of separation, such as microfiltration, remove not only microbes but also particles of cationic polymer, with the result that the wet strength properties are reduced, which is undesirable. Therefore, it is preferable to leave the deactivated microorganism in the mixture to avoid the problem of reducing wet strength properties.

It has unexpectedly been determined that resin compositions having high concentrations of solids, i.e., greater than 15 wt %, more preferably greater than 20 wt %, preferably greater than 25 wt %, can be biodehalogenated using microorganisms and/or enzymes, when the resin comprises tertiary amine-based resins, such as Kymene® 450, Crepetrol® A3025 or Crepetrol® 80E. In the past, secondary amine-based resins, such as Kymene® 557H, Kymene® 557LX, Kymene® SLX, Kymene® Plus are not efficiently biodehalogenated at concentrations of solids of 15 or greater weight %. In the present invention, secondary amine-based resins can be efficiently biodehalogenated at 15 or greater wt %. In addition, it has been found that Daniels resins can be biodehalogenated at 15 or greater wt %.

With regard to Daniel's resins, it is noted that cationic water-soluble resins, derived from the reaction of epihalohydrins, such as epichlorohydrin, and polyalkylene polyamines, such as ethylenediamine (EDA), bis-hexamethylenetriamine (BHMT) and hexamethylenediamine (HMDA) have long been known. These polyalkylene polyamine-epihalohydrin resins are described in patents such as U.S. Pat. No. 3,655,506 to J. M. Baggett, et al. and others such as U.S. Pat. No. 3,248,353 and U.S. Pat. No. 2,595,935 to Daniel et al. from which their generic description as "Daniel's Resins" arises. The disclosures of these patents are incorporated by reference herein in their entireties.

The polyalkylene polyamine employed in the present invention can preferably be selected from the group consisting of polyalkylene polyamines of the formula:

where: n=1-7, x=1-6, R=H or $CH_2Y$, Z=H or $CH_3$, and $Y=CH_2Z$, H, $NH_2$, or $CH_3$, polyalkylene polyamines of the formula:

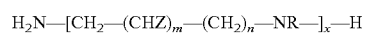

where: m=1-6, n=1-6, and m+n=2-7, R=H or $CH_2Y$, Z=H or $CH_3$, and $Y=CH_2Z$, H, $NH_2$, or $CH_3$, and mixtures thereof.

Polyalkylene polyamine-epihalohydrin resins comprise the water-soluble polymeric reaction product of epihalohydrin and polyalkylene polyamine. In making Daniel's Resins the polyalkylene polyamine is added to an aqueous mixture of the epihalohydrin so that during the addition the temperature of the mixture does not exceed 60° C. Lower temperatures lead to further improvements, though too low a temperature may build dangerously latent reactivity into the system. The preferred temperatures fall within the range of about 25° C. to about 60° C. More preferred is a range of from about 30° C. to about 45° C.

Alkylation of the polyamine occurs rapidly proceeding to form secondary and tertiary amines depending on the relative amounts of epihalohydrin and polyamine. The levels of epihalohydrin and polyamine are such that between about 50% and 100% of the available amine nitrogen sites are alkylated to tertiary amines. Preferred levels are between about 50% and about 80% alkylation of the amine nitrogen sites. Excess epihalohydrin beyond that required to fully alkylate all the amine sites to the tertiary amine is less preferred because this results in increased production of epihalohydrin byproducts.

Following complete addition of the polyamine, the temperature of the mixture is allowed to rise and/or the mixture is heated to effect crosslinking and azetidinium formation. The crosslinking rate is a function of concentration, temperature, agitation, and the addition conditions of the polyamine, all of which can be readily determined by those skilled in the art. The crosslinking rate can be accelerated by the addition of small shots of the polyamine or other polyamines of the present invention or addition of various alkalies at or near the crosslinking temperature.

The resin can be stabilized against further crosslinking to gelation by addition of acid, dilution by water, or a combination of both. Acidification to pH 5.0 or less is generally adequate.

The preferred polyamines are bishexamethylenetriamine, hexamethylenediamine, and their mixtures.

While not wishing to be bound by theory, it is noted that resins such as Kymene® at high solids concentrations have difficulty and are less easily biodehalogenated at high solids concentrations, such as above 15 percent total solids due to viscosity increase and gelling of the resin resulting in reduced growth for the bacteria and loss of product functionality due to crosslinking (=loss of functional groups). By controlling conditions, including pH, time, temperature, concentration of microorganism or enzyme, biodehalogenation can be achieved for Daniels resins and tertiary amine-based resins at, higher total solids can be achieved. Preferred conditions for Daniels resins, for example Kymene® 736, are total solids level of 15 to 40 weight percent, preferably 18-30 weight percent, even more preferably 18-22 weight percent. Preferred conditions for tertiary amine-base resins are total solids level of 15 to 40 weight percent, preferably 18-35 weight percent and even more preferably 18-28 weight percent. Preferred pH ranges for both Daniels resins and tertiary amine-base resins are pH of 5.0 to 8.0, more preferably pH ranges of 5.5 to 7.5. Preferred temperature ranges for both Daniels resins and tertiary amine-base resins are 20 to 40 degrees C, more preferably 25 to 35 degrees C. It is preferred that the biodehalogenation step, starting for inoculation, is completed in 48 hours or less. It is more preferred that the biodehalogenation step is completed in 24 hours of less from starting for the inoculation.

It was not expected that biodehalogenation could be accomplished at high solids concentration due to lack of water for the microorganisms, higher osmotic pressure for higher solids content, and undefined problems, such as concentration of low molecular weight species. Moreover, it would be expected that pretreatment to remove higher residuals may be needed, such as by dilution or filtration. Moreover, it would not be expected that biodehalogenation could be achieved in a reasonable period of time, such as within 48 hours. Still further, there would be an expectation of storage instability at high solids concentrations; however, the resin compositions according to the present invention are storage stable, and are not susceptible to gelling. The advantages of the present invention are obtained for high solids whether or not the resin composition is treated to remove or reduce CPD-forming species.

Still further, in present invention, high-solids, wet-strength resins can be biodehalogenated. Additionally, the enzymatic treatment can be done simultaneously with the biodehalogenation treatment. Although resins based on pre-polymers without endcapping, such as Kymene E7219, can be biodehalogenated or enzymatically treated during biodehalogenation, it is preferred that these wet-strength resins are end-capped resins as described in WO 99/09252 and U.S. Pat. No. 6,222,006, which are incorporated herein by reference in entirety. While not wishing to be bound by theory, it is noted that the end-capper is preferably is not an inhibitor of biodehalogenation. For example, residual hexanoic acid from the production of an end-capped prepolymer inhibits the microbial biodehalogenation, while residual acetic acid does not inhibit the microbial biodehalogenation. The preferred solids level for wet strength resins is 15 to 40 weight percent, preferably 16-35 weight percent and even more preferably 18-28 weight percent. An additional range that can be used in the present invention is 15-30 weight.

In order to more clearly describe the present invention, the following non-limiting examples are provides for the purpose of representation, and are not to be construed as limiting the scope of the invention. All parts and percentages in the examples are by weight unless indicated otherwise. Moreover, ND in the Examples indicates "Not Detected".

EXAMPLES

Unless otherwise noted, Brookfield Viscosity was determined with a Brookfield LVDV-II+ Programmable Viscometer at 25° C. The procedure used was based on the Operating Instructions, Manual No. M/97-164. This Viscometer will determine viscosity only if the correct spindle and rpm is used for the viscosity of the sample. Unless otherwise noted all CPD and DCP measurements are on a wet basis.

Example 1

Synthesis of a High-Solids Polyaminopolyamide Resin

A 3-L round-bottom flask was fitted with a condenser, a pH meter, a temperature controlled circulating bath, an addition funnel and a mechanical stirrer. To the kettle was added 775.0 g of 49.6 wt % aqueous poly(adipic acid-co-diethylenetriamine) (available from Hercules Incorporated) and 505.3 g of water. The solution was heated to 25° C. and then 162.5 g of epichlorohydrin (Aldrich, 99%) was added over about 2 minutes. The temperature was allowed to increase to 40° C. and was maintained at this temperature. 2.45 hours after the addition of the epichlorohydrin, 1046.5 g of water was added and the reaction mixture was heated. After the reaction mixture reached 50° C. (20 minutes), 7.54 g of 96% sulfuric acid was added. The temperature was raised to 70° C. and the Gardner-Holdt viscosity at 25° C. was monitored. After the Gardner-Holdt viscosity reached G, the reaction was quenched by the addition 187.5 g of water containing 12.90 g of 96% sulfuric acid. The reaction mixture was allowed to cool to 25° C. The pH was adjusted to 3.5 with an additional 3.00 grams of 96% sulfuric acid. The resin had 21.08% total solids and a Brookfield viscosity of 153 cps.

Example 2

Enzyme-Treatment of a Polyaminopolyamide-Epi Resin (Example 1)

A 250-mL round-bottom flask was fitted with a condenser, a pH meter, a temperature controlled circulating bath and a mechanical stirrer. To the flask was added 200.0 g of Example 1. The pH was raised to 7.58 with 4.88 g of 30% aqueous sodium hydroxide. A 5 g aliquot was removed, the pH lowered to about 3 with 96% sulfuric acid and analyzed by GC. Then 5.18 g of ALCALASE 2.5 L type DX (available from Novozymes, used as received) was added. The temperature was raised from 21° C. to 30° C. within 15 minutes and the Gardner-Holdt viscosity at 25° C. was monitored. Five gram aliquots of the reaction mixture were removed and the pH lowered to about 3 with 96% sulfuric acid at 1, 2, 4, 6 and 8 hours after the addition of ALCALASE and analyzed by GC. The pH was adjusted to 7.5 at 2 hours with 0.27 g of 30% aqueous sodium hydroxide and at 4 hours with 0.18 g of 30% aqueous sodium hydroxide. After 8 hours, the pH was lowered to 3.4 by addition of 2.22 g of 96% sulfuric acid. The resin had a Brookfield viscosity of 95 cps (at 25° C.).

Example 3

Biodehalogenation of Example 2

A 250-mL round-bottom flask was fitted with a condenser, a pH meter, a temperature controlled circulating bath, an air sparge tube and a mechanical stirrer. To the flask was added 100.0 g of Example 2 and 55.56 g of water. The pH was raised to 5.9 with 2.24 g of 30% aqueous sodium hydroxide and then 17.28 g of a blend of microorganisms comprising an inoculum from a biodehalogenated polyaminopolyamide-epichlorohydrin resin. This represents a starting value of cell concentration of from about 105 to about 106 cells/ml. This starting value corresponds to a final treatment level of about $10^9$ cells/ml as the process proceeds. The inoculum was added, together with 1.36 g of a nutrient solution. (The nutrient solution consisted of 8026 ppm of potassium dihydrogen phosphate, 27480 ppm of urea, 4160 ppm of magnesium sulfate and 840 ppm of calcium chloride in tap water.) The microorganisms used were: *Arthrobacter histidinolovorans* (HK1) and *Agrobacterium radiobacter* (HK7). The air sparge was started, the temperature was maintained at 30° C. and the pH was maintained at 5.8 by periodic addition of 30% aqueous sodium hydroxide. After 48 hours, the mixture was cooled to room temperature and the pH was adjusted to 3.0 with 0.97 g of 96% sulfuric acid and 2.05 g of biocide solution was added. [The biocide solution consisted of 10% active Proxel® BD (from Zeneca Biocides) and 1.67% potassium sorbate in deionized water.] The resin had a total solids of 14.5 wt. % and had a Brookfield viscosity of 62 cps (at 25° C.).

Acid Test

The amount of CPD producing species of this was estimated using the following acid test. A portion of resin to be tested was charged into a bottle containing a magnetic stirrer. The pH was adjusted to 1.0 with 96% sulfuric acid. The bottle was capped and placed in a 50° C. water bath and maintained at 50° C. with stirring. Periodically, aliquots were removed from the bottle and submitted for GC analysis. The CPD produced after 24 hours is used to estimate the amount of CPD producing species. See Table 1 for results.

added. The temperature was raised from 22° C. to 35° C. within 15 minutes and the Gardner-Holdt viscosity at 25° C. was monitored. Five gram aliquots of the reaction mixture were removed and the pH lowered to about 3 with 96% sulfuric acid at 1, 2, 4, 6 and 8 hours after the addition of ALCALASE and analyzed by GC. The pH was adjusted to 7.5 at 2 hours with 0.80 g of 30% aqueous sodium hydroxide, at 4 hours with 0.48 g of 30% aqueous sodium hydroxide and at 6 hours with 0.78 g of 30% aqueous sodium hydroxide. At 6 hours, the temperature was increased to 38° C. After 8 hours, the pH was lowered to 3.5 by addition of 6.54 g of 96% sulfuric acid. The resin had a Brookfield viscosity of 32 cps (at 25° C.).

Biodehalogenation:

A 1-L round-bottom flask was fitted with a condenser, a pH meter, a temperature controlled circulating bath, an air sparge tube and a mechanical stirrer. To the flask was added 700.0 g of the resin produced above. The pH was raised to 5.9 with 8.21 g of 30% aqueous sodium hydroxide and then 77.8 g of a blend of microorganisms comprising an inoculum from a biodehalogenated polyaminopolyamide-epichlorohydrin resin. This represents a starting value of cell concentration of from about 105 to about 106 cells/ml. This starting value corresponds to a final treatment level of about 109 cells/ml as the process proceeds. The inoculum was added, together with 6.12 g of a nutrient solution. (The nutrient solution consisted of 8026 ppm of potassium dihydrogen phosphate, 27480 ppm of urea, 4160 ppm of magnesium sulfate and 840 ppm of calcium chloride in tap water.) The microorganisms used were: *Arthrobacter histidinolovorans* (HK1) and *Agrobacterium radiobacter* (HK7). The air sparge was started, the temperature was maintained at 30° C. and the pH was maintained at 5.8 by periodic addition of 30% aqueous sodium hydroxide. After 48 hours, the mixture was cooled to room temperature and the pH was

TABLE 1

| Resin Information | Temp (° C.) | Time (hours) | Gardner-Holdt Viscosity | Epi (ppm) | 1,3-DCP (ppm) | 2,3-DCP (ppm) | 3-CPD (ppm) |
|---|---|---|---|---|---|---|---|
| Example 2a | 21 | 0 | N | 15 | 1746 | 1.3 | 276 |
| Example 2b | 30 | 1 | F-G | 20 | 2004 | 1.6 | 478 |
| Example 2c | 30 | 2 | E-F | 22 | 1720 | 1.7 | 508 |
| Example 2d | 30 | 4 | D-E | 24 | 1802 | 1.4 | 680 |
| Example 2e | 30 | 6 | D-E | 26 | 1753 | 1.5 | 664 |
| Example 2f | 30 | 8 | B-F | — | — | — | — |
| Example 3 | — | — | — | 0.1 | ND | 0.8 | ND |
| Acid Test | 50 | 24 | — | ND | ND | 0.10 | 0.66 |

Comp. Example 4

Enzyme-Treatment of a Polyaminopolyamide-Epi Resin

Enzyme-Treatment:

A portion of Example 1 was diluted to 13.5% total solids. A 1-L round-bottom flask was fitted with a condenser, a pH meter, a temperature controlled circulating bath and a mechanical stirrer. To the flask was added 900.0 g of the 13.5% Example 1. The pH was raised to 7.54 with 13.85 g of 30% aqueous sodium hydroxide. A 5 g aliquot was removed, the pH lowered to about 3 with 96% sulfuric acid and analyzed by GC. Then 15.0 g of AlCALASE 2.5 L type DX (available from Novozymes, used as received) was adjusted to 3.0 with 4.02 g of 96% sulfuric acid and 8.42 g of biocide solution was added. [The biocide solution consisted of 10% active Proxel® BD (from Zeneca Biocides) and 1.67% potassium sorbate in deionized water.] The resin had a total solids of 14.77 wt. % and had a Brookfield viscosity of 61 cps (at 25° C.).

Example 5

Handsheet Evaluation of Example 3 and Comp. Example 4

Paper handsheets were prepared on a Noble and Wood handsheet machine at pH 7.5 with 50:50 Rayonier bleached Kraft:Crown Vantage bleached hardwood Kraft dry lap pulp refined to 500 mL Canadian standard freeness. Sheets were generated having 40 lb/3000 sq. ft. basis weight containing 0.5-1.0% of treated resin (based on the solids of untreated resin). Handsheets were wet pressed to 33% solids and dried on a drum drier at 230° C. for 55 seconds to give 3-5% moisture. The paper was conditioned according to TAPPI Method T-402 and tested. Dry tensile strength was determined using TAPPI Method T-494. Wet tensile strength was determined using TAPPI Method T-456 with a two hour soak time. The CPD in paper products was determined by the following procedure:

CPD in Paper Products Procedure

Cold Water Extraction of Paper

The sample is cut and extracted with water at 23° C. (±2° C.) for 24 hours, mixing occasionally. After the extraction period, the extract is filtered if necessary.

Note: Make sure all the paper is immersed in the water.

Procedure
1. Wearing protective gloves, cut the sample into small pieces (approximately 1 cm×1 cm), and collect in a plastic bag. Mix the pieces well.
2. Weigh 10 grams of sample, to the nearest 0.0001 g, and place in a conical flask.
3. Add 200 mL reagent grade water and stopper the flask.
4. Place the flask in a water bath for 24 hours at 23° C. (±2° C.).
5. Decant the solution into a 250 mL volumetric flask. If necessary, filter the preparation using a fritted glass filter funnel with filter flask. Rinse the pieces twice with additional reagent grade water and fill to the mark.

Apparatus
1. Conical flask, wide neck with ground glass stopper
2. Volumetric flask, 250 mL
3. Fritted glass filter funnel (available from Lab Glass cat #lG-7080-170), with filter flask, 500 mL
4. Water bath, to keep constant temperature of 23° C. (±2° C.).
5. Paper cutter or scissors
6. Analytical balance, capable of weighing to the nearest 0.0001 g.

Reagents
1. Water, available from Burdick & Jackson, cat. #365-4

ECD Method—Ether Elution & Derivitization

The separation of the analytes from the aqueous extract takes place through a liquid-liquid extraction column. DCP and 3-CPD are derivitized with heptafluro-butrylimadozole (HFBI) and analyzed by gas chromatography using a µ-electron capture detector (µ-ECD).

Procedure
1. Pipette 20 mL of the extracted water solution into a 35-mL vial.
2. Add 2.34 g of NaCl to the vial. Cap and shake well until NaCl dissolves.
3. Pour the solution onto an extrelut column and allow to sit for 15 minutes.
4. After the waiting period, elute with 250 mL of eluant solution (95% diethyl ether/isooctane. (Collect the eluant in a volumetric flask)
5. Pour the eluant into a 500 mL round bottom flask
6. The solvent is removed using a rotary evaporator (Note: the vacuum is not to exceed 200 mm Hg), until about 15 mL remains.
7. Pipette 1 mL Internal Standard solution into the remaining iso-octane.
8. A method blank of reagent grade water prepared according to steps 2 to 7 must also be run to check for interference Derivitization
1. Using a syringe or micropipette, add 200 µL of HFBI to the flask. Stopper the flask and swirl the solution to mix well.
2. Let the flask stand for 15 minutes at room temperature.
3. Quantitatively transfer the solution to a 25 mL mixing cylinder and fill to the mark with iso-octane.
4. Add ~1.5 mL reagent grade water to the volumetric, stopper and shake to mix well. A precipitate will have formed but will disappear when mixed well with the water.
5. After the phase separation, remove approximately 20 mL of the organic phase and put in a 30 mL glass vial, which contains 2 mL reagent grade water. Shake vigorously for 1 minute.
6. After phase separation. Remove the water layer and discard. The organic phase will be analyzed by gas chromatography using a i-Electron Capture detector (ECD).

Reagents
1. Di-ethyl ether, available from FLUKA, P.O. Box 355, Milwaukee, Wis., Cat. No. 31690. **must use a.p. quality; the ether may be neither dried nor stabilized with ethanol.
1. Water, available from Burdick & Jackson, cat. #365-4
2. Sodium Chloride
3. 1,3-DCP; available TCI Americas, Cat. No. D0402.
4. 3-CPD; available Aldrich, Cat. No. 10227-1.
5. Acetonitrile, Nanograde; available Fisher, Cat. No. 2442.
6. Iso-octane, EM Science, Cat. No. TX1389
7. Eluant: 95 mL di-ethyl ether/5 mL iso-octane.
8. Heptaflurobutyryllimadozole (HFBI), available from Pierce, Cat. No. 44211
9. 3-methoxy-1,2-propanediol (internal standard)
10. Solid phase extraction column, Supelco, Supelco Park, Bellefonte, PA 16823-0048, prepared according to Section XXX. Cat. No. 57022.
11. Varian Hydromatrix; available Varian, Inc., Cat. No. 00198003.

Apparatus
1. Gas Chromatograph, Hewlett Packard Model 5890, or equivalent, capable of linear column temperature programming, and equipped with a µ-Electron Capture detector (µ-ECD).
2. Data handling system, Hewlett Packard ChemStation or equivalent.
3. Chromatographic column, DB-5MS, 60 meters×0.25 mm I.D.—available from J & W Scientific Inc., 91 Blur Ravin Road, Folsom, Calif. 95630, Cat. No. 122-5562.
4. Flasks, volumetric, glass stoppered, 5 mL, 10 mL, 25 mL, 50 mL, 100 mL, 250 mL.
5. Vials, glass with teflon-lined screw caps, 17 mL, 30 mL, 4 oz.
6. Pipettes, transfer, 0.5, 1, 2, 3, 5, 10, 20 mL Class A.
7. Medicine droppers, glass—Fisher, Cat. No. 13-701
8. Analytical balance, capable of weighing to the nearest 0.0001 g.
9. Solid phase extraction column, Supelco, Supelco Park, Bellefonte, Pa. 16823-0048, prepared according to Section XXX. Cat. No. 57022.
10. Glass wool 11. 500 mL round bottom flask with stopper, available from Lab Glass, Cat. No. 013 and Cat. No. 114.
12. Rotary Vacuum evaporator operating at 35-40° C./800 mbar
13. 500 μL syringe or disposable micro-pipettes
14. Type A mixing cylinders, 25 mL; available Fisher, Cat. No. 08-563-1F.

Internal Standard Solution (Low Level)
1. Weigh 50 mg 3-methoxy-1,2-propanediol into a 50-mL volumetric flask and record the weight to the nearest 0.0001 g.
2. Dilute to the mark with acetonitrile.
3. Pipette 0.25 mL of solution in step 2 into a 100-mL volumetric flask and dilute to volume with diethyl ether.
4. Pipette 10.0 mL of solution in step 3 into a 100 mL volumetric and dilute to volume with diethyl ether.

1,3-DCP, 3-CPD Calibration Solution (Low Level)
1. Weigh 50 mg 1,3-dichloro-2-propanol into a 50-mL volumetric flask and record the weight to the nearest 0.0001 g.
2. Dilute to the mark with acetonitrile.
3. Pipette 0.5 mL of solution in step 2 into a 10-mL volumetric flask and dilute to volume with diethyl ether.
4. Weigh 50 mg 3-chloro-1,2-propanediol into a 50-mL volumetric flask and record the weight to the nearest 0.0001 g.
5. Dilute to the mark with acetonitrile.
6. Pipette 0.5 mL of solution in step 5 into a 10-mL volumetric flask and dilute to volume with diethyl ether.
7. Combine solutions in step 3 and step 6 in a 30-mL vial and mix well.
8. Pipette 2.5 mL of solution in step 7 into a 100-mL volumetric flask and dilute to volume with diethyl ether.
9. Pipette 10.0 mL of solution in step 8 into a 100-mL volumetric flask and dilute to volume with diethyl ether. This is the Calibration Stock Solution.

Calibration Curves Low Level:
1. Pipette 0.1 mL of the Calibration Stock Solution into a 25-mL volumetric flask containing 1.0 mL of the Internal Standard Solution. Using a pipette, add 5.9 mL of diethyl ether to the flask. This will be calibration Level #1.
2. Pipette 0.2 mL of the Calibration Stock Solution into a 25-mL volumetric flask containing 1.0 mL of the Internal Standard Solution. Using a pipette, add 5.8 mL of diethyl ether to the flask. This will be calibration Level #2.
3. Pipette 0.5 mL of the Calibration Stock Solution into a 25-mL volumetric flask containing 1.0 mL of the Internal Standard Solution. Using a pipette, add 5.5 mL of diethyl ether to the flask. This will be calibration Level #3.
4. Pipette 1.0 mL of the Calibration Stock Solution into a 25-mL volumetric flask containing 1.0 mL of the Internal Standard Solution. Using a pipette, add 5.0 mL of diethyl ether to the flask. This will be calibration Level #4.
5. Pipette 2.0 mL of the Calibration Stock Solution into a 25-mL volumetric flask containing 1.0 mL of the Internal Standard Solution. Using a pipette, add 4.0 mL of diethyl ether to the flask. This will be calibration Level #5.
6. Add 15 mL iso octane to each of the volumetric flasks from steps 1 through 6.
7. Using a syringe, add 200 μL HFBI to each of the volumetric flasks from step 7, then stopper and allow to stand at room temperature for 15 minutes with occasional shaking.
8. Dilute each flask to a final volume of 25-mL with iso-octane.
9. Add ~1.5 mL reagent grade water to each volumetric, stopper and shake to mix well. A precipitate will have formed but will disappear when mixed well with the water.
10. After the phase separation, transfer approximately 20 mL of the organic phase to a 30-mL glass vials in which each contain 2 mL reagent grade water. Shake vigorously for 1 minute.
11. After phase separation. Remove the water layer and discard. The organic phases will be analyzed by gas chromatography using a μ-Electron Capture detector (μ-ECD) to determine the calibration curve.

GC Operating Conditions

| Temperatures | |
| --- | --- |
| Column | |
| Initial | 50° C. |
| Initial hold time | 2 min |
| Initial rate | 1.5° C./min |
| $2^{nd}$ temp | 100° C. |
| $2^{nd}$ hold | 5 min |
| $2^{nd}$ rate | 25° C./min |
| Final | 300° C. |
| Final hold time | 10 min |
| Inlet | 250° C. |
| Detector temp | 320° C. |
| Flow Rates | |
| Helium (carrier gas) | 1.5 mL/min at 20 psi (column head pressure at 35° C.) |
| Argon/Methane | 60 mL/min |

Section XXX

Preparing the Extrelut QE Columns
1. Using a solid phase extraction reservoir, push approximately 0.5 g of glass wool to the bottom.
2. Weigh 18 g Varian Hydromatrix and pour into reservoir. Using a glass probe, pack extrelut tightly.
3. Place approximately 0.5 g glass wool on top of reservoir.

Results are reported in Table 2. The data show that enzyme treatment at 21% solids gave essentially the same results as treatment at 13.5% solids. These results allow for a more economical enzymatic treatment.

Table 2. Natural Aged Paper Results

Natural Aged Paper

| | | | | Basis Wt. Normalized | | |
| --- | --- | --- | --- | --- | --- | --- |
| Example | % Resin Added | Dry Tensile (lbs/in) | Wet Tensile (lbs/in) | % wet/ dry | % of Comp. Ex XX | CPD in Paper (ppb) |
| Blank | — | 17.55 | 0.53 | 3 | — | <3 |
| Comp. Ex. 4a | 0.25 | 24.47 | 3.89 | 16 | — | <3 |
| Comp. Ex. 4b | 0.50 | 24.61 | 4.86 | 20 | — | <3 |
| Comp. Ex. 4c | 1.00 | 24.65 | 5.70 | 23 | — | 10 |
| Example 3a | 0.25 | 22.58 | 3.60 | 16 | 93 | <3 |
| Example 3b | 0.50 | 23.88 | 4.63 | 19 | 95 | <3 |
| Example 3c | 1.00 | 24.72 | 5.38 | 22 | 94 | 7 |

Example 6-17

General Procedure for Enzyme-Treatment of a Polyaminopolyamide-Epi Resins

A 500-mL round-bottom flask was fitted with a condenser, a pH meter, a temperature controlled circulating bath and a mechanical stirrer. To the flask was added 400.0 g of Kymene® E7219 (Available from Hercules Incorporated, Wilmington, Del.; 21.51% solids, 267 cps Brookfield viscosity at 25° C.). The pH was increased with 30% aqueous sodium hydroxide. A 5 g aliquot was removed, the pH lowered to about 3 with 96% sulfuric acid and analyzed by GC. ALCALASE 2.5 L type DX (available from Novozymes, used as received) was added (amount indicated in Table 3). The temperature was raised within 15 minutes to the desired treatment temperature and the Gardner-Holdt viscosity at 25° C. was monitored. Five gram aliquots of the reaction mixture were removed and the pH lowered to about 3 with 96% sulfuric acid at 1, 2, 4, 6 and 8 hours after the addition of ALCALASE and analyzed by GC. The pH was checked every hour and was adjusted with 30% aqueous sodium hydroxide if the pH drifted by more than 0.10. After 8 hours, the pH was lowered to 3.5 by addition of 96% sulfuric acid. If the Gardner-Holdt viscosity reading was in-between letters, both letters are recorded in the Table. If the viscosity was increasing more than desired, the pH adjustments with 30% aqueous sodium hydroxide were discontinued. If the viscosity increased to the point of risking gelation, the pH was lowered to 3.5 by addition of 96% sulfuric acid. BV (cps) is the Brookfield Viscosity (measured at 25° C.) of the final resin. The ALCALASE: Active solids ratio is defined as the amount of ALCALASE 2.5 L type DX, used as received, compared to the amount of active solids in the resin. See Table 3 for details.

Example 18-19

General Procedure for Enzyme-Treatment of a Polyaminopolyamide-Epi Resins

A 250-mL round-bottom flask was fitted with a condenser, a pH meter, a temperature controlled circulating bath and a mechanical stirrer. To the flask was added 200.0 g of Example 1. The pH was increased with 30% aqueous sodium hydroxide. A 4 g aliquot was removed, the pH lowered to about 3 with 96% sulfuric acid and analyzed by GC. ALCALASE 2.5 L type DX (available from Novozymes, used as received) was added (amount indicated in Table 3). The temperature was raised within 15 minutes to the desired treatment temperature and the Gardner-Holdt viscosity at 25° C. was monitored. Four gram aliquots of the reaction mixture were removed and the pH lowered to about 3 with 96% sulfuric acid at 1, 2, 4, 6 and 8 hours (if non-gelled) after the addition of ALCALASE and analyzed by GC. The pH was checked every hour and was adjusted with 30% aqueous sodium hydroxide if the pH drifted by more than 0.10. After 8 hours, the pH was lowered to 3.5 by addition of 96% sulfuric acid. If the Gardner-Holdt viscosity reading was in-between letters, both letters are recorded in Table 3. If the viscosity was increasing more than desired, the pH adjustments with 30% aqueous sodium hydroxide were discontinued. With both reactions, the viscosity was allowed to increase to the point of gelation. BV (cps) is the Brookfield Viscosity (measured at 25° C.) of the final resin. The ALCALASE:Active solids ratio is defined as the weight amount of ALCALASE 2.5 L type DX, used as received, compared to the weight amount of active solids in the resin. See Table 3 for details.

TABLE 3

| Resin Example | ALCALASE: Active Solids | pH | Temp (° C.) | Time (hours) | Gardner-Holdt Viscosity | BV (cps) |
|---|---|---|---|---|---|---|
| Example 6a | 1.0:8.3 | 7.2 | 21 | 0 | I-J | |
| Example 6b | 1.0:8.3 | 7.2 | 30 | 1 | E-F | |
| Example 6c | 1.0:8.3 | 7.2 | 30 | 2 | D-E | |
| Example 6d | 1.0:8.3 | 7.2 | 30 | 4 | D | |
| Example 6e | 1.0:8.3 | 7.2 | 30 | 6 | D | |
| Example 6f | 1.0:8.3 | 7.2 | 30 | 8 | D | 84 |
| Example 7a | 1.0:8.3 | 7.8 | 21 | 0 | I-J | |
| Example 7b | 1.0:8.3 | 7.8 | 30 | 1 | E-F | |
| Example 7c | 1.0:8.3 | 7.8 | 30 | 2 | B-F | |
| Example 7d | 1.0:8.3 | 7.8 | 30 | 4 | B-F | |
| Example 7e | 1.0:8.3 | 7.8 | 30 | 6 | F-G | |
| Example 7f | 1.0:8.3 | 7.8 | 30 | 8 | H-I | 255 |
| Example 8a | 1.0:16.6 | 7.2 | 22 | 0 | I-J | |
| Example 8b | 1.0:16.6 | 7.2 | 25 | 1 | G-H | |
| Example 8c | 1.0:16.6 | 7.2 | 25 | 2 | G | |
| Example 8d | 1.0:16.6 | 7.2 | 25 | 4 | F | |
| Example 8e | 1.0:16.6 | 7.2 | 25 | 6 | B-F | |
| Example 8f | 1.0:16.6 | 7.2 | 25 | 8 | B-F | 105 |
| Example 9a | 1.0:16.6 | 7.8 | 22 | 0 | I-J | |
| Example 9b | 1.0:16.6 | 7.8 | 25 | 1 | G-H | |
| Example 9c | 1.0:16.6 | 7.8 | 25 | 2 | G-H | |
| Example 9d | 1.0:16.6 | 7.8 | 25 | 4 | I | |
| Example 9e | 1.0:16.6 | 7.8 | 25 | 6 | J-K | |
| Example 9f | 1.0:16.6 | 7.8 | 25 | 7 | L-M | 379 |
| Example 10a | 1.0:11.1 | 7.2 | 23 | 0 | I-J | |
| Example 10b | 1.0:11.1 | 7.2 | 25 | 1 | F-G | |
| Example 10c | 1.0:11.1 | 7.2 | 25 | 2 | F | |
| Example 10d | 1.0:11.1 | 7.2 | 25 | 4 | E | |
| Example 10e | 1.0:11.1 | 7.2 | 25 | 6 | D-E | |
| Example 10f | 1.0:11.1 | 7.2 | 25 | 8 | D | 77 |
| Example 11a | 1.0:11.1 | 7.8 | 23 | 0 | I-J | |
| Example 11b | 1.0:11.1 | 7.8 | 25 | 1 | F-G | |
| Example 11c | 1.0:11.1 | 7.8 | 25 | 2 | F | |
| Example 11d | 1.0:11.1 | 7.8 | 25 | 4 | B-F | |
| Example 11e | 1.0:11.1 | 7.8 | 25 | 6 | F | |
| Example 11f | 1.0:11.1 | 7.8 | 25 | 8 | F | 149 |
| Example 12a | 1.0:8.3 | 7.2 | 22 | 0 | H-I | |
| Example 12b | 1.0:8.3 | 7.2 | 25 | 1 | F-G | |
| Example 12c | 1.0:8.3 | 7.2 | 25 | 2 | B-F | |
| Example 12d | 1.0:8.3 | 7.2 | 25 | 4 | D-E | |
| Example 12e | 1.0:8.3 | 7.2 | 25 | 6 | C | |
| Example 12f | 1.0:8.3 | 7.2 | 25 | 8 | B-C | 60 |
| Example 13a | 1.0:8.3 | 7.8 | 22 | 0 | H-I | |
| Example 13b | 1.0:8.3 | 7.8 | 25 | 1 | F-G | |
| Example 13c | 1.0:8.3 | 7.8 | 25 | 2 | E-F | |
| Example 13d | 1.0:8.3 | 7.8 | 25 | 4 | D-E | |
| Example 13e | 1.0:8.3 | 7.8 | 25 | 6 | C | |
| Example 13f | 1.0:8.3 | 7.8 | 25 | 8 | C-D | 85 |
| Example 14a | 1.0:8.3 | 7.2 | 22 | 0 | H-I | |
| Example 14b | 1.0:8.3 | 7.2 | 35 | 1 | F-G | |
| Example 14c | 1.0:8.3 | 7.2 | 35 | 2 | B-F | |
| Example 14d | 1.0:8.3 | 7.0 | 35 | 4 | F | |
| Example 14e | 1.0:8.3 | 6.9 | 35 | 6 | F-G | |
| Example 14f | 1.0:8.3 | 6.8 | 35 | 8 | G-H | 175 |
| Example 15a | 1.0:8.3 | 7.5 | 22 | 0 | H-I | |
| Example 15b | 1.0:8.3 | 7.5 | 35 | 1 | F-G | |
| Example 15c | 1.0:8.3 | 7.5 | 35 | 2 | F | |
| Example 15d | 1.0:8.3 | 7.3 | 35 | 4 | J-K | |
| Example 15e | 1.0:8.3 | 7.3 | 35 | 4.5 | N | 434 |
| Example 16a | 1.0:16.6 | 7.5 | 22 | 0 | H-I | |
| Example 16b | 1.0:16.6 | 7.5 | 25 | 1 | C | |
| Example 16c | 1.0:16.6 | 7.5 | 25 | 2 | G | |
| Example 16d | 1.0:16.6 | 7.5 | 25 | 4 | F-G | |
| Example 16e | 1.0:16.6 | 7.5 | 25 | 6 | B-F | |
| Example 16f | 1.0:16.6 | 7.5 | 25 | 8 | B-F | 138 |
| Example 17a | 1.0:11.1 | 7.5 | 22 | 0 | H-I | |
| Example 17b | 1.0:11.1 | 7.5 | 25 | 1 | F-C | |
| Example 17c | 1.0:11.1 | 7.5 | 25 | 2 | B-F | |
| Example 17d | 1.0:11.1 | 7.5 | 25 | 4 | D-E | |
| Example 17e | 1.0:11.1 | 7.5 | 25 | 6 | D | |
| Example 17f | 1.0:11.1 | 7.5 | 25 | 8 | D | 80 |

TABLE 3-continued

| Resin Example | ALCALASE: Active Solids | pH | Temp (° C.) | Time (hours) | Gardner-Holdt Viscosity | BV (cps) |
|---|---|---|---|---|---|---|
| Example 18a | 1.0:16.3 | 7.5 | 22 | 0 | H | |
| Example 18b | 1.0:16.3 | 7.5 | 33 | 1 | I | |
| Example 18c | 1.0:16.3 | 7.5 | 33 | 2 | K | |
| Example 18d | 1.0:16.3 | 7.5 | 33 | 3 | V | |
| Example 18e | 1.0:16.3 | 7.5 | 33 | 4 | W-X | |
| Example 19a | 1.0:8.1 | 7.5 | 22 | 0 | H | |
| Example 19b | 1.0:8.1 | 7.5 | 33 | 1 | F | |
| Example 19c | 1.0:8.1 | 7.5 | 33 | 2 | B-F | |
| Example 19d | 1.0:8.1 | 7.5 | 33 | 4 | F | |
| Example 19e | 1.0:8.1 | 7.5 | 33 | 6 | H | |
| Example 19f | 1.0:8.1 | 7.5 | 33 | 7 | L | |
| Example 19g | 1.0:8.1 | 7.5 | 33 | 8 | Gel | |

Example 20

Combined Enzyme-Treatment and Biodehalogenation of a Polyaminopolyamide-Epi Resin Scale-Up 1 (Starter Preparation):

A portion of Kymene® E7219 (Available from Hercules Incorporated, Wilmington, Del.; 21.51% solids, 267 cps Brookfield viscosity at 25° C.) was diluted to 13.5% total solids. A 400-mL round-bottom flask was fitted with a condenser, a pH meter, a temperature controlled circulating bath, an air sparge tube and a mechanical stirrer. To the flask was added 400 g of the 13.5% Kymene® E7219. The pH was raised to 7.54 with 7.42 g of 30% aqueous sodium hydroxide. A 5 g aliquot was removed, the pH lowered to about 3 with 96% sulfuric acid and analyzed by GC. Then 3.33 g of AlCALASE 2.5 L type DX (available from Novozymes, used as received) was added and then 44.4 g of a blend of microorganisms comprising an inoculum from a biodehalogenated polyaminopolyamide-epichlorohydrin resin. This represents a starting value of cell concentration of from about $10^5$ to about $10^6$ cells/ml. This starting value corresponds to a final treatment level of about $10^9$ cells/ml as the process proceeds. The inoculum was added, together with 3.50 g of a nutrient solution. (The nutrient solution consisted of 8026 ppm of potassium dihydrogen phosphate, 27480 ppm of urea, 4160 ppm of magnesium sulfate and 840 ppm of calcium chloride in tap water.) The microorganisms used were: *Arthrobacter histidinolovorans* (HK1) and *Agrobacterium radiobacter* (HK7). The air sparge was started, the temperature was maintained at 30° C. The treatment was monitored by Gardner-Holdt viscosity and the bacterial growth was monitored by optical density ($OD_{600}$). $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. Periodically, 5 g aliquot were removed, the pH lowered to about 3 with 96% sulfuric acid and analyzed by GC. The pH of the treatment was maintained for the first 30 hours at 7.1-7.5 by periodic addition of 30% aqueous sodium hydroxide. After 30 hours, the pH was lower to 5.8 by addition of 96% sulfuric acid. After 48 hours, the resulting mixture was used as the inoculum for Scale-up 2 below.

Scale-Up 2:

A portion of Kymene® E7219 (Available from Hercules Incorporated, Wilmington, Del.; 21.51% solids, 267 cps Brookfield viscosity at 25° C.) was diluted to 13.5% total solids. A 2-L round-bottom flask was fitted with a condenser, a pH meter, a temperature controlled circulating bath, an air sparge tube and a mechanical stirrer. To the flask was added 1600 g of the 13.5% Kymene® E7219. The pH was raised to 7.52 with 30.38 g of 30% aqueous sodium hydroxide. A 5 g aliquot was removed, the pH lowered to about 3 with 96% sulfuric acid and analyzed by GC. Then 13.32 g of AlCALASE 2.5 L type DX (available from Novozymes, used as received) was added and then 177.8 g of the inoculum from Scale-up 1 above was added, together with 14.0 g of a nutrient solution. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The treatment was monitored by Gardner-Holdt viscosity and the bacterial growth was monitored by optical density ($OD_{600}$). $OD_{600}$ was determined by measuring the optical density at a wavelength of 600 μm using a Spectronic® Genesys™ UV/Vis spectrophotometer (Spectronic Instruments, Incorporated, Rochester, N.Y., USA) and a disposable cuvet with 1-cm pathlength. Periodically, 5 g aliquot were removed, the pH lowered to about 3 with 96% sulfuric acid and analyzed by GC. The pH of the treatment was maintained for the first 8.5 hours at 7.2-7.5 by periodic addition of 30% aqueous sodium hydroxide. For the remaining treatment time, the pH was maintained at pH 6.8-7.2 by periodic addition of 30% aqueous sodium hydroxide. After 48 hours, the mixture was cooled to room temperature and the pH was adjusted to 2.8 with 12.80 g of 96% sulfuric acid and 19.26 g of biocide solution was added. [The biocide solution consisted of 10% active Proxel® BD (from Zeneca Biocides) and 1.67% potassium sorbate in deionized water.] See Table 4 for the results from monitoring the treatment. Table 4.

TABLE 4

| Aliquot | Time | pH (30 C.) | Gardner Viscosity | $OD_{600}$ (abs.) | DCP (ppm) | CPD (ppm) |
|---|---|---|---|---|---|---|
| −1 | "0" | 7.49(21C.) | D/E | 0.058 | 679 | 204 |
| −78A | 0 | Time "0" is right after NaOH addition, | | | | |
| | | Time 0 is right after Alcalase addition. | | | | |
| — | 0.25 | 7.43 | — | — | — | — |
| −2 | 1 | 7.39 | B/C | — | 589 | 242 |
| −3 | 2 | 7.32 | B/C | 0.062 | 585 | 268 |
| −4 | 4 | 7.32 | B/C | 0.067 | 586 | 309 |
| −5 | 6 | 7.25 | B | 0.064 | 584 | 322 |
| — | 7 | 7.20 to 7.52 | — | — | — | — |
| −6 | 8 | 7.50 | B | 0.061 | 554 | 331 |
| −7 | 10 | 7.40 | B | 0.064 | 540 | 363 |
| −8 | 14 | 7.26 to 7.45 | B | 0.064 | 519 | 399 |
| −9 | 24 | 7.20 | D | 0.109 | 476 | 384 |
| — | 28 | 7.09 | E/F | 0.165 | — | — |
| −10 | 30 | 7.05 to 5.79 | G/H | 0.201 | 422 | 296 |
| — | 32 | 5.83 | H | 0.260 | — | — |
| — | 34 | 5.84 | — | 0.300 | — | — |
| −11 | 37 | 5.81 | H/I | 0.328 | 360 | 317 |
| −12 | 48 | 5.60 | I/J | 0.473 | ND | 198 |
| −1 | "0" | 7.48(26C.) | D/E | 0.071 | 745 | 256 |
| −82A & 84B | 0 | Time "0" is right after NaOH addition, | | | | |
| | | Time 0 is right after Alcalase addition. | | | | |
| — | 0.25 | 7.46 | — | — | — | — |
| −2 | 1 | 7.39 | C/D | — | 639 | 394 |
| −3 | 2 | 7.32 | C/D | 0.086 | 614 | 427 |

TABLE 4-continued

| Aliquot | Time | pH (30 C.) | Gardner Viscosity | OD$_{600}$ (abs.) | DCP (ppm) | CPD (ppm) |
|---|---|---|---|---|---|---|
| −4 | 4 | 7.20 to 7.40 | C | 0.108 | 579 | 531 |
| −5 | 6 | 7.31 | C | 0.138 | 537 | 540 |
| −6 | 8.5 | 7.16 | B/C | 0.198 | 391 | 629 |
| −7 | 12.5 | 7.02 | B/C | 0.271 | 66 | 796 |
| −8 | 22 | 6.81 | D | 0.481 | ND | 144 |
| — | 24 | 6.78 to 7.12 | — | — | | |
| | | Resin is light tannish yellow. | | | | |
| — | 28 | 7.02 | D/E | 0.560 | | |
| −9 | 30 | 6.99 | D/E | 0.578 | 0.3 | 7.8 |
| −10 | 48 | 6.95 | D/E | 0.611 | 0.3 | 0.5 |
| Acid Test | — | — | — | — | ND | 1.1 |

Example 21

Combined Enzyme-Treatment and Biodehalogenation of a Polyaminopolyamide-Epi Resin. (Using Twice the Alcalase as in Example 20)

Scale-Up 1 Starter Preparation:

A portion of Kymene® E7219 (Available from Hercules Incorporated, Wilmington, Del.; 21.51% solids, 267 cps Brookfield viscosity at 25° C.) was diluted to 13.5% total solids. A 400-mL round-bottom flask was fitted with a condenser, a pH meter, a temperature controlled circulating bath, an air sparge tube and a mechanical stirrer. To the flask was added 400 g of the 13.5% Kymene® E7219. The pH was raised to 7.52 with 7.38 g of 30% aqueous sodium hydroxide. A 5 g aliquot was removed, the pH lowered to about 3 with 96% sulfuric acid and analyzed by GC. Then 6.66 g of AlCALASE 2.5 L type DX (available from Novozymes, used as received) was added and then 44.4 g of a blend of microorganisms comprising an inoculum from a biodehalogenated polyaminopolyamide-epichlorohydrin resin. This represents a starting value of cell concentration of from about $10^5$ to about $10^6$ cells/ml. This starting value corresponds to a final treatment level of about $10^9$ cells/ml as the process proceeds. The inoculum was added, together with 3.50 g of a nutrient solution. (The nutrient solution consisted of 8026 ppm of potassium dihydrogen phosphate, 27480 ppm of urea, 4160 ppm of magnesium sulfate and 840 ppm of calcium chloride in tap water.) The microorganisms used were: *Arthrobacter histidinolovorans* (HK1) and *Agrobacterium radiobacter* (HK7). The air sparge was started, the temperature was maintained at 30° C. The treatment was monitored by Gardner-Holdt viscosity and the bacterial growth was monitored by optical density (OD$_{600}$). OD$_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. Periodically, 5 g aliquot were removed, the pH lowered to about 3 with 96% sulfuric acid and analyzed by GC. The pH of the treatment was maintained for the first 24 hours at 7.2-7.5 by periodic addition of 30% aqueous sodium hydroxide. After 24 hours, the pH was allow to drift down to pH 6.71 over the course of 24 hours. After 48 hours, the resulting mixture had a Brookfield viscosity of 71 cps (measured at 25° C.). This mixture was used as the inoculum for Scale-up 2 below.

Scale-Up 2:

A portion of Kymene® E7219 (Available from Hercules Incorporated, Wilmington, Del.; 21.51% solids, 267 cps Brookfield viscosity at 25° C.) was diluted to 13.5% total solids. A 2-L round-bottom flask was fitted with a condenser, a pH meter, a temperature controlled circulating bath, an air sparge tube and a mechanical stirrer. To the flask was added 1600 g of the 13.5% Kymene® E7219. The pH was raised to 7.55 with 29.99 g of 30% aqueous sodium hydroxide. A 5 g aliquot was removed, the pH lowered to about 3 with 96% sulfuric acid and analyzed by GC. Then 26.64 g of AlCALASE 2.5 L type DX (available from Novozymes, used as received) was added and then 177.8 g of the inoculum from Scale-up 1 above was added, together with 14.0 g of a nutrient solution. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The treatment was monitored by Gardner-Holdt viscosity and the bacterial growth was monitored by optical density (OD$_{600}$). OD$_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. Periodically, 5 g aliquot were removed, the pH lowered to about 3 with 96% sulfuric acid and analyzed by GC. The pH of the treatment was maintained for the first 8 hours at 7.1-7.5 by periodic addition of 30% aqueous sodium hydroxide. For the remaining treatment time, the pH was maintained at pH 6.8-7.2 by periodic addition of 30% aqueous sodium hydroxide. After 48 hours, the mixture was cooled to room temperature and the pH was adjusted to 2.8 with 12.85 g of 96% sulfuric acid and 19.26 g of biocide solution was added. [The biocide solution consisted of 10% active Proxel® BD (from Zeneca Biocides) and 1.67% potassium sorbate in deionized water.] The resin had a Brookfield viscosity of 30 cps (measured at 25° C.). See Table 5 for the results from monitoring the treatment. Table 5.

TABLE 5

| Sample | Time | pH (30 C.) | G/H Viscosity | OD$_{600}$ (abs.) | DCP (ppm) | CPD (ppm) |
|---|---|---|---|---|---|---|
| −1 | "0" | 7.50(21C.) | D/E | 0.060 | 770 | 269 |
| −80B | 0 | Time "0" is right after NaOH addition, Time 0 is right after Alcalase addition. | | | | |
| — | 0.25 | 7.44 | — | — | — | — |
| −2 | 1 | 7.37 | B | — | 657 | 412 |
| −3 | 2 | 7.34 | B | 0.058 | 645 | 477 |
| −4 | 4 | 7.30 | A/B | 0.063 | 677 | 526 |
| −5 | 6 | 7.25 | A/B | 0.062 | 623 | 508 |
| — | 7 | 7.20 to 7.52 | — | — | — | — |
| −6 | 8 | 7.50 | A | 0.059 | 599 | 504 |
| −7 | 10 | 7.40 | A/A-1 | 0.062 | 615 | 559 |
| −8 | 14 | 7.26 to 7.47 | A/A-1 | 0.065 | 592 | 569 |
| −9 | 24 | 7.22 | A/B | 0.139 | 516 | 560 |
| — | 28 | 7.12 | A/B | 0.259 | — | — |
| −10 | 30 | 7.11 | B | 0.295 | 387 | 508 |
| — | 32 | 7.07 | B | 0.336 | — | — |
| — | 34 | 7.03 | — | 0.391 | — | — |
| −11 | 37 | 6.93 | B | 0.475 | ND | 497 |
| −12 | 48 | 6.71 | C | 0.716 | ND | ND |

TABLE 5-continued

Scale-up 2

| Aliquot | Time | pH (30 C.) | G/H Viscosity | OD$_{600}$ (abs.) | DCP (ppm) | CPD (ppm) |
|---|---|---|---|---|---|---|
| -1 | "0" | 7.48(26C) | D/E | 0.101 | 778 | 237 |
| -84B | 0 | Time "0" is right after NaOH addition, Time 0 is right after Alcalase addition. | | | | |
| — | 0.25 | 7.46 | — | — | — | — |
| -2 | 1 | 7.39 | C | — | 641 | 384 |
| -3 | 2 | 7.31 | B/C | 0.129 | 583 | 433 |
| -4 | 4 | 7.10 to 7.40 | B | 0.199 | 507 | 531 |
| -5 | 6 | 7.34 | B | 0.270 | 371 | 562 |
| -6 | 8.5 | — | A/B | 0.422 | 96 | 653 |
| | | Recalibration of the pH meter. | | | | |
| -7 | 12.5 | 6.75 to 7.14 | A | 0.618 | ND | 303 |
| -8 | 22 | 6.85 | A/B | 0.877 | ND | 0.5 |
| — | 24 | 6.85 to 7.09 | — | — | | |
| | | Resin is dark orange, tannish-brown | | | | |
| — | 28 | 7.01 to 7.10 | A/B | 0.932 | | |
| -9 | 30 | 7.08 | A/B | 0.959 | ND | ND |
| -10 | 48 | 6.84 | B | 1.080 | ND | ND |
| Acid Test | — | — | — | — | ND | 0.1 |

Examples 20 and 21 clearly show that the enzyme treatment and the biodehalogenation treatment can be effectively combined. When twice the Alcalase was used, a preferred balance of conditions allowed a preferred viscosity to be obtained.

Example 22

Alcalase-Biodehalogenation of Kymene® E7219 (see Table 6 for Data and Details)

Kymene® E7219 (Available from Hercules Incorporated, Wilmington, Del.; Zwijndrecht, Netherlands plant) was diluted to 13.40% and had a Brookfield viscosity of 76 cps. Pasteurization: A 3-L round-bottom flask was fitted with a condenser, a temperature controlled circulating bath and a mechanical stirrer. To the flask was added 2800 g of the resin. The pH was adjusted from 3.4 to 3.0 with concentrated sulfuric acid and was heated over 15 min from 25° C. to 80° C. The resin was held at 80° C. for 15 minutes, cooled to 75° C. in 10 minutes and then cooled to 30° C. The pasteurized resin had a Brookfield viscosity of 48 cps and was stored in sterile containers.

Sterilization of Kymene E7219:

A 500 g portion of the Kymene E7219 was diluted to 8%, placed in an autoclavable bottle and heated in an autoclave at 121° C. for 20 minutes. The resin was allowed to cool and was used to start the Scale-up 1 preparation of resin inoculum. Note: Pasteurized Kymene E7219 (using conditions described above) has also been used successful to start the Scale-up 1 preparation of resin inoculum.

Biodehalogenation:

Preparation of resin inoculum [Scale-up 1 (SU1)]: A 250-mL round-bottom flask was fitted with a condenser, a pH meter, a temperature controlled circulating bath, an air sparge tube and a mechanical stirrer. To the flask was added 200 g of sterilized Kymene E7219 and the pH was raised to 7.2 with 3.28 g of 30% aqueous sodium hydroxide and then 400 microliters of HK7 concentrated starter culture was added (1:500, HK7 to resin) [See Example 24 for concentrated starter culture preparation] and 1.75 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density (OD$_{600}$) and the biodehalogenation was monitored by GC. OD$_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. The pH of the reaction mixture was maintained by periodic addition of 30% aqueous sodium hydroxide. After 34 hours, 68 microliters of HK1 concentrated starter culture was added (1:3000, HK1 to resin) [See Example 24 for concentrated starter culture preparation] was added. After 43 hours, the resulting resin was used as inoculum for SU2.

Scale-Up 2 (SU2):

A 500-mL round-bottom flask was fitted with a condenser, a pH meter, a temperature controlled circulating bath, an air sparge tube and a mechanical stirrer. To the flask was added 350 g of the pasteurized resin. The pH was raised to 7.5 with 7.40 g of 30% aqueous sodium hydroxide and then 5.03 g of Alcalase 2.5L type DX (available from Novozymes), 87.5 g of the SU1 resin inoculum (20% inoculation rate) and 3.06 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density (OD600) and the biodehalogenation was monitored by GC. OD$_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. The pH of the reaction mixture was maintained by periodic addition of 30% aqueous sodium hydroxide. After 23 hours, the resulting resin was used as inoculum for SU3. To increase the molecular weight of the resin (as indicated by Gardner-Holdt viscosity or Brookfield viscosity), a 200 g portion of the remaining resin (Brookfield viscosity of 10 cps) was raised to pH 8.5 with 1.17 g of 30% aqueous sodium hydroxide and the temperature was raised to 40° C. After 3 hours, the resin had a desirable viscosity and the reaction was quenched by the addition of concentrated sulfuric acid to pH 2.7. The resulting resin had a Brookfield viscosity of 25 cps.

Scale-Up 3 (SU3) and General Procedure for Repeated Batch Mode:

A 250-mL round-bottom flask was fitted with a condenser, a pH meter, a temperature controlled circulating bath, an air sparge tube and a mechanical stirrer. To the flask was added 350 g of the pasteurized resin. The pH was raised to 7.6 with 8.59 g of 30% aqueous sodium hydroxide and then 4.38 g of Alcalase 2.5L type DX (available from Novozymes), 87.5 g of the SU2 resin inoculum (20% inoculation rate) and 3.06 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density (OD$_{600}$) and the biodehalogenation was monitored by GC. OD$_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. The pH of the reaction mixture was maintained by periodic addition of 30% aqueous sodium hydroxide. After 23 hours, the resulting resin was used as inoculum for SU4. The pH of the remaining resin was adjusted to 2.8 with concentrated sulfuric acid and 300 ppm of potassium sorbate was added as a 10% aqueous solution. This resin had a Brookfield viscosity of 49 cps.

Scale-Up 4 (SU4) Batch:
The procedure was similar to SU3, see Table 6 for data and details.

Scale-Up 5-10 Batches:
The procedure was similar to SU3 except the 13.40% Kymene E7219 was used without pasteurization (see Table 6 for data and details).

A similar set of experiments with 10% inoculation rate for SU3-SU8 batches resulted in successful, efficient batch biodehalogenations.

TABLE 6

Scale-up 1: 200 g 8% E7219 (autoclaved), no Alcalase, 400 microliters HK7, 1.75 g nutrient solution.

| Sample | Time (hours) | pH (30 C,) | Gardner Viscosity | $OD_{600}$ (abs.) | 30% NaOH (g) | DCP (ppm) | CPD (ppm) |
|---|---|---|---|---|---|---|---|
| — | 0 | 7.25 | — | — | 3.28 | — | — |
| X33031-15-1 | 1 | 7.24 | — | 0.174 | — | 445 | 183 |
| X33031-15-2 | 4 | 7.22 | — | 0.154 | — | 402 | 211 |
| X33031-15-3 | 20 | 7.15 | — | 0.138 | — | 259 | 309 |
| X33031-15-4 | 24 | 7.12 | — | 0.152 | — | 222 | 333 |
| X33031-15-5 | 28 | 7.07-7.27 | — | 0.177 | 0.12 | 140 | 375 |
| — | 32 | 7.17 | — | 0.211 | — | — | — |
| — | 34 | 7.13 | — | 0.249 | Added 68 microliters of HK1 inoculum | | |
| — | — | 7.13 | — | 0.272 | — | — | — |
| X33031-15-6 | 43 | 6.84 | — | 0.657 | — | ND | 0.36 |

Scale-up 2: 350 g 13.5% E7219 (pasteurized), 5.03 g Alcalase, 87.5 g of −15, 3.06 g nutrient solution.

| Sample | Time (hours) | (pH 7.50) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.49 | — | — | 7.40 | — | — |
| X33031-18-1 | 1 | 7.39-7.64 | A-B | 0.128 | 0.65 | 434 | 485 |
| X33031-18-2 | 4 | 7.41-7.64 | A | 0.170 | 0.49 | 10 | 814 |
| X33031-18-3 | 7 | 7.50-7.6 | A | 0.257 | 0.26 | ND | 720 |
| X33031-18-4 | 10 | 7.44-7.64 | A | 0.372 | 0.29 | ND | 380 |
| X33031-18-5 | 13 | 7.47-7.59 | A | 0.543 | 0.22 | ND | 0.56 |
| X33031-18-6 | 23 | 7.56 | A-1/A | 0.678 | — | ND | 0.38 |

Inoculum was removed for next batch, the remainder was set aside for crosslinking. Brookfield viscosity was 10 cps (at pH 7.50), crosslinking of 200 g of −18 started 8 hours later:

| Sample | Time (hours) | (pH 7.50) pH (30 C.) | Gardner Viscosity | $OD_{600}$ (abs.) | 30% NaOH (g) | DCP (ppm) | CPD (ppm) |
|---|---|---|---|---|---|---|---|
| | | 7.20 (24 C.) | — | | | | |
| | | 7.11 (31 C.) | — | | | | |
| | 0 | 8.50 (31 C.) | — | | 1.17 | | |
| | 0.5 | 8.23 (40 C.) | | | | | |
| | 1 | 8.01 | | | | | |
| | 1.5 | 7.93 | A-1/A | | | | |
| | 2 | 7.82 | | | | | |
| | 2.5 | 7.74 | A-B | | | | |
| X33047-27-1 | 3 | 7.68 | Kill reaction with sulfuric acid | | | | |
| | | 2.65 | | | | | |

The final resin had a Brookfield viscosity of 25 cps.

Scale-up 3: 350 g 13.5% E7219 (pasteurized), 4.38 g Alcalase, 87.5 g of −18, 3.06 g nutrient solution.

| Sample | Time (hours) | (pH 7.60) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.63 | — | — | 8.59 | — | — |
| X33031-20-1 | 1 | 7.51-7.79 | A-B | 0.148 | 0.70 | 476 | 430 |
| X33031-20-2 | 4 | 7.54-7.73 | A | 0.209 | 0.40 | 186 | 616 |
| X33031-20-3 | 7 | 7.49-7.74 | A | 0.307 | 0.56 | ND | 715 |
| X33031-20-4 | 10 | 7.52-7.71 | A | 0.436 | 0.37 | ND | 437 |
| X33031-20-5 | 13 | 7.49-7.70 | A | 0.594 | 0.37 | ND | 152 |
| X33031-20-6 | 23 | 7.48 | B-C | 0.726 | — | ND | 0.29 |

TABLE 6-continued

The final resin had a Brookfield viscosity of 49 cps.
Scale-up 4: 350 g 13.5% E7219 (pasteurized), 4.38 g Alcalase, 87.5 g of −20, 3.06 g nutrient solution.

| Sample | Time (hours) | (pH 7.50) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.60 | — | — | 7.51 | — | — |
| X33031-23-1 | 1 | 7.53-7.62 | A-B | 0.176 | 0.24 | 588 | 360 |
| X33031-23-2 | 4 | 7.40-7.61 | A-B | 0.211 | 0.48 | 516 | 470 |
| X33031-23-3 | 7 | 7.46-7.63 | A | 0.258 | 0.38 | 227 | 736 |
| X33031-23-4 | 10 | 7.47-7.62 | A | 0.312 | 0.29 | ND | 811 |
| X33031-23-5 | 12.5 | 7.52-7.42 | A | 0.344 | 0.24 | ND | 747 |
| X33031-23-6 | 25 | 7.12 | C | 0.642 | — | ND | 0.06 |

The final resin had a Brookfield viscosity of 116 cps.
Scale-up 5: 350 g 13.5% E7219 (not pasteurized), 4.38 g Alcalase, 87.5 g of −23, 3.06 g nutrient solution.

| Sample | Time (hours) | (pH 7.50) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.63 | — | — | 6.88 | — | — |
| X33031-25-1 | 1 | 7.37-7.64 | B | 0.175 | 0.67 | 499 | 426 |
| X33031-25-2 | 3 | 7.47-7.64 | B | 0.248 | 0.39 | 384 | 527 |
| X33031-25-3 | 7 | 7.35-7.65 | B | 0.378 | 0.71 | 48 | 631 |
| X33031-25-4 | 24 | 7.12 | F-G | 0.743 | — | ND | 0.06 |

The final resin was a soft gel (dispersible).
Scale-up 6: 350 g 13.5% E7219 (not pasteurized), 4.38 g Alcalase, 118 g of −25, 3.06 g nutrient solution.

| Sample | Time (hours) | (pH 7.3) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.41 | — | — | 6.60 | — | — |
| X33031-27-1 | 1 | 7.34-7.51 | B-C | 0.234 | 0.43 | 466 | 438 |
| X33031-27-2 | 7 | 7.13-7.33 | B-C | 0.342 | 0.42 | ND | 766 |
| X33031-27-3 | 19 | 6.91 | B-C | 0.542 | — | ND | 7.1 |

The final resin had a Brookfield viscosity of 87 cps.
Scale-up 7: 350 g 13.5% E7219 (not pasteurized), 4.38 g Alcalase, 87.5 g of −27, 3.06 g nutrient solution.

| Sample | Time (hours) | (pH 7.35) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.44 | — | — | 7.27 | — | — |
| X33031-29-1 | 1 | 7.35-7.54 | B-C | 0.146 | 0.52 | 676 | 548 |
| X33031-29-2 | 4 | 7.30-7.55 | B | 0.213 | 0.70 | 319 | 959 |
| X33031-29-3 | 8 | 7.37 | A-B | 0.301 | 0.00 | ND | 1074 |
| X33031-29-4 | 11 | 7.29-7.42 | A | 0.354 | 0.26 | ND | 774 |
| X33031-29-5 | 14 | 7.27-7.43 | — | 0.402 | 0.30 | ND | 442 |
|  | 15 | 7.33 | B | — |  |  |  |
| X33031-29-6 | 23 | 7.13 | C | 0.645 |  | ND | 0.13 |
|  |  |  |  | Acid Test |  | <0.10 | 2.4 |

The final resin had a Brookfield viscosity of 77 cps.
Scale-up 8: 350 g 13.5% E7219 (not pasteurized), 4.38 g Alcalase, 87.5 g of −29, 3.06 g nurtrient solution.

| Sample | Time (hours) | (pH 7.30) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.44 | — | — | 7.17 | — | — |
| X33031-31-1 | 1 | 7.37-7.46 | B-C | 0.173 | 0.27 | 652 | 504 |
| X33031-31-2 | 4 | 7.23-7.34 | B | 0.264 | 0.28 | 351 | 754 |
| X33031-31-3 | 7 | 7.16-7.38 | A-B | 0.361 | 0.46 | ND | 921 |
| X33031-31-4 | 10 | 7.20-7.42 | B | 0.456 | 0.47 | ND | 486 |
| X33031-31-5 | 13 | 7.20-7.39 | B | 0.628 | 0.43 | ND | 4.6 |
| X33031-31-6 | 23 | 7.23 | B-C | 0.726 |  | ND | 0.14 |

TABLE 6-continued

The final resin had a Brookfield viscosity of 65 cps.
Scale-up 9: 700 g 13.5% E7219 (not pasteurized), 8.76 g Alcalase, 175 g of −31, 6.12 g nutrient solution.

| Sample | Time (hours) | (pH 7.25) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.27 | — | — | 12.86 | — | — |
| X33031-33-1 | 1 | 7.18-7.39 | B-C | 0.191 | 1.02 | 527 | 402 |
| X33031-33-2 | 4 | 7.15-7.38 | B | 0.271 | 0.99 | 283 | 672 |
| X33031-33-3 | 7 | 7.18-7.40 | A-B | 0.337 | 1.05 | ND | 859 |
| X33031-33-4 | 10 | 7.24-7.38 | A-B | 0.397 | 0.68 | ND | 619 |
| X33031-33-5 | 13 | 7.27-7.39 | B | 0.474 | 0.53 | ND | 361 |
| X33031-33-6 | 23 | 7.11 | B-C | 0.697 | | ND | 0.12 |
| | | | | | Acid Test | <0.10 | 2.9 |

The final resin had a Brookfield viscosity of 40 cps.
Scale-up 10: 350 g 13.5% E7219 (not pasteurized), 4.38 g Alcalase, 87.5 g of −33, 3.06 g nutrient solution.

| Sample | Time (hours) | (pH 7.20) pH (30 C.) | Gardner Viscosity | $OD_{600}$ (abs.) | 30% NaOH (g) | DCP (ppm) | CPD (ppm) |
|---|---|---|---|---|---|---|---|
| — | 0 | 7.17 | — | — | 7.20 | — | — |
| X33031-35-1 | 1 | 7.15-7.34 | B-C | 0.188 | 0.48 | 582 | 462 |
| X33031-35-2 | 4 | 7.17-7.32 | B | 0.293 | 0.43 | 299 | 624 |
| X33031-35-3 | 7 | 7.17-7.31 | A-B | 0.380 | 0.45 | ND | 812 |
| X33031-35-4 | 10 | 7.16-7.28 | A-B | 0.487 | 0.29 | ND | 487 |
| X33031-35-5 | 13 | 7.12-7.30 | B | 0.647 | 0.32 | ND | 150 |
| X33031-35-6 | 23 | 7.12 | A-B | 0.820 | | ND | 0.22 |
| | | | | | Acid Test | <0.10 | 2.7 |

The final resin had a Brookfield viscosity of 34 cps.

EXAMPLES:

For the following examples TS means total solids
Demi Water means demineralized water
DO means dissolved oxygen Example 23

Demonstrate Feasibility of Applying Biodehalogenation Technology for Creping Aid Crepetrol® 80E with Increasing % TS to Reduce Both 1,3-DCP and/or 3-CPD Levels to Concentrations Below 1 ppm Crepetrol® 80E (=A3025) creping aid resin (26.6% TS as received), a tertiary amine-based resin available from Hercules Incorporated (Wilmington, Del.), was obtained from the Voreppe plant, France.

Three sterile 250 ml Erlenmeyer flasks were charged with 50 ml batches of resin with increasing %TS (table 7). Dilutions of the resin were made with sterilized demineralized water. Prior inoculation, each diluted 50 ml resin was supplemented with 0.5 ml nutrient solution and the pH of the solution was adjusted to pH 5.8 using a 33% NaOH solution. This nutrient solution contained the following components per L sterilized demineralized water: 33 g Urea, 5 g $KH_2PO_4$, 5 g $MgSO_4.0.7H_2O$ and 1 g $CaCl_2.0.2H_2O$. A 1 ml concentrated starter culture of both *Arthrobacter histidinolovorans* (HK1) and *Agrobacterium radiobacter* (HK7) was removed from the −80° C. freezer and thawed in a waterbath for 1-2 min. at 30° C. An 50 µl aliquot of the *A. histidinolovorans* (HK1) suspension and 200 µl aliquot of the *A. radiobacter* (HK7) suspension were both used to inoculate a 250 ml sterile Erlenmeyer shake flask containing the described dilutions of 50 ml supplemented Crepetrol® 80E. After inoculation, the cultures were incubated for 48 hours at 30° C. in a rotary-shaking incubator (250 rpm; G25 model; New Brunswick Scientific Co., Inc. New Jersey, USA). Bacterial growth was followed in time and determined by measuring the optical density at a wavelength of 600 nm using an Ultrospec1000 UV/Vis spectrophotometer (Pharmacia Biotech, Sweden) and a 3 ml disposable cuvet with 1-cm pathlength (table 8). Samples were pH adjusted to pH 3.5

TABLE 7

| | EPI residuals and total solids of Crepetrol ® 80E. | | | | | | |
|---|---|---|---|---|---|---|---|
| Sample | Crepetrol ® 80E (ml) | Demi water (ml) | EPI (ppm) | 1,3-DCP (ppm) | 2,3-DCP (ppm) | 3-CPD (ppm) | TS (%) |
| 26.6% (as received) | 50 | 0 | nd | 35 | nd | 100 | 26.58 |
| 20% | 37.6 | 12.4 | nd | 26 | nd | 75 | 20.0 |
| 15% | 28.2 | 21.8 | nd | 20 | nd | 56 | 15.0 | using concentrated sulfuric acid and 0.1% Proxel® BD(available form Zeneca Biocides) was added. Samples were tested for EPI residuals (1,3-DCP and 3-CPD) analysis by GC (table 8).

TABLE 8

Bacterial growth in Crepetrol ® 80 E with increasing % TS.

| | $OD_{600}$ value | | |
|---|---|---|---|
| Time (hrs) | C80E 15% TS | C80E 20% TS | C80E 26.6% TS |
| 0 | 0.296 | 0.256 | 0.246 |
| 16.5 | 0.558 | 0.525 | 0.440 |
| 19.5 | 0.570 | 0.530 | 0.460 |
| 25 | 0.575 | 0.545 | 0.475 |
| 41 | 0.643 | 0.590 | 0.490 |
| 48 | 0.735 | 0.600 | 0.505 |
| 1,3-DCP (ppm) after 42 hrs | <1 | <1 | <1 |
| 3-CPD (ppm) after 42 hrs | <1 | <1 | <1 |

Example 24

Sequential Enzyme- and Bio-Process with High %TS:

Demonstrate efficiency of process started with 3-CPD release via ALCALASE treatment of Crepetrol® 80E, followed by biodehalogenation. Test biodehalogenated product for residual polymer bound 3-CPD using the acid test.

A. Treatment of 2.5L Crepetrol® 80E.

A clean and sterile 2.5L bioreactor (BioFlo3O0O bioreactor, controlled via AFS-BioCommand software; New Brunswick Scientific Co., Inc. New Jersey, USA) was charged with 2.5 kg Crepetrol® 80E resin (26.6% TS) obtained from Hercules Voreppe plant, France. The pH of Crepetrol® 80E was adjusted to pH 7.5 using a 33% NaOH solution and the pH-PID controller (Proportional Intergral Display) of the installed bioreactor. Enzyme treatment was started via addition of 12.5 g Alcalase® 2.5L DX (Novozymes). The resin was enzyme treated for a 6 hrs time period using the following incubation conditions:

| pH | 7.5 |
|---|---|
| Temperature | controlled at 25° C. |
| Agitation | controlled at 600 rpm |

Samples (25 ml) were taken in time after 2, 4 and 6 hours to monitor epi residuals (table 9). Collected samples were pH adjusted to pH 3.5 with concentrated sulphuric acid and stored at 4° C. for further analysis. The EPI residuals (3-CPD and the 1,3-DCP) were analyzed by GC.

TABLE 9

3-CPD release in time of treated Crepetrol ® 80 E at 26.6% TS.

| Sample | Incubation Time | 3-CPD (ppm) | 1,3-DCP (ppm) |
|---|---|---|---|
| Crepetrol ® 80E 26.6% | 0 | 100 | 35 |
| C80E-Alc1 A | 2 | 129 | 37 |
| C80E-Alc1 B | 4 | 170 | 39 |
| C80E-Alc1 C | 6 | 168 | 39 |

B. Preparation of Pre-Cultures of HK1 and HK7 to Start Biodehalogenation Process.

A single colony of *A. histidinolovorans* (HK1) and a single colony of *A. radiobacter* (HK7) (both separately grown on minimal medium salts medium containing DCP/CPD) were used to inoculate each separately a sterile Erlenmeyer shake flask (250 ml) containing 50 ml of sterile Brain Heart Infusion medium (BHI; Oxoid Ltd, Basingstoke, Hampshire, England; ready made medium, cat.no. CM225). Both pre-cultures were separately incubated for 24 h at 30° C. in a temperature controlled rotary-shaking incubator (250 rpm; G25 model; New Brunswick Scientific Co., Inc. New Jersey, USA). The optical density of the batch grown HK1 and HK7 culture was determined using an Ultrospec1000 UV/Vis spectrophotometer (Pharmacia Biotech, Sweden) at a wavelength of 600 nm and using a 3-ml disposable cuvet with 1-cm pathlength. The growth was determined by measuring the optical density at a wavelength of 600 nm using a 20-times (water) diluted culture sample (table 10). These pre-cultures were used to start the biodehalogenation process of enzyme treated Crepetrol® 80E.

Table 10: Optical Density of 24 Hours BHI Grown HK1 and HK7 Batch Culture.

TABLE 10

Optical density of 24 hours BHI grown HK1 and HK7 batch culture.

| Culture | $OD_{600\ nm}$ (20* dilution) |
|---|---|
| *A. histidinolovorans* HK1 | 0.386 |
| *A. radiobacter* HK7 | 0.455 |

To make concentrated starter cultures the precultures were concentrated via centrifugation (10,000 rpm for 10 min. at 4° C.) and supplemented with 10% glycerol and then storaged at −80° C.

C. Biodehalogenation of Treated Crepetrol® 80E.

After 6 hrs enzyme treatment (section A), the pH of the resin in the bioreactor was adjusted to pH 5.8 with concentrated sulphuric acid. The reactor content was supplemented with 25 ml nutrient solution and 0.04% PPG2000 (antifoam) (polypropylene glycol P2000 (Fluka Chemie AG, Germany)). This nutrient solution contained the following components per L sterilized demi water: 33 g Urea, 5 g $KH_2PO_4$, 5 g $MgSO_4.0.7H_2O$ and 1 g $CaCl_2.0.2H_2O$. Pre-cultures of *A. histidinolovorans* (HK1) and *radiobacter* (HK7) (50 ml each; section B) were used to start the biodehalogenation process of the enzyme treated resin. Both culture were simultaneously used to inoculate a batch fermentation in the 2.5L bioreactor. Parameter settings of the bioreactor control unit, operated in batch mode, were as follows:

pH controlled at pH 5.8 (PID controlled addition of 25% NaOH solution)

Temperature controlled at 30° C.

Stirrer speed 600 rpm (maximum speed of 800 rpm; via DO value controlled)

Aeration set at 1.0 vvm (2.5L/min; compressed air), minimal DO value set at 5% air saturation Complete removal of epi residuals from the bioreactor content was closely monitored in time, via analysis by gas chromatography (GC-XSD; table 11). After a total incubation time of 51 hours, the batch culture was finished. The pH of the enzyme treated and biodehalogenated resin was adjusted to pH 3.5 using concentrated sulphuric acid and the product was supplemented with 0.2% potassium sorbate and 0.12% Proxel BD. A sample of finished product was used in an acid test to determine the polymer bound 3-CPD fraction. The pH of this sample (25 ml) was adjusted to pH 1.0 with concentrated sulphuric acid, subsequently the sample was incubated for 24 hours at 50° C. After incubation the pH was re-adjusted to pH 3.5 with a 33% NaOH solution. Epi residuals were determined via GC-XSD measurement (table 11).

TABLE 11

Epi residuals after sequential enzyme treatment, bio-treatment and acid test.

| Treatment | Process Time (hrs) | 1,3-DCP (ppm) | 3-CPD (ppm) |
|---|---|---|---|
| Crepetrol ® 80E 26.6% TS | 0 | 35 | 100 |
| 1st treatment phase | 2 | 37 | 129 |
|  | 4 | 39 | 170 |
|  | 6 | 39 | 168 |
| 2nd Biodehalogenation phase | 7 | 39 | 168 |
|  | 29.5 | nd | <1 |
|  | 50 | nd | <1 |
| Acid Test of C80E feed (Control) |  | 38 | 188 |
| Acid Test of Product |  | nd | 29 |

Example 25

Combined Enzyme-Bio-Process with High % TS:

Demonstrate efficiency of process with simultaneously started 3-CPD release via treatment of Crepetrol® 80E and at the same time biodehalogenation of free 3-CPD. Test biodehalogenated product for residual polymer bound 3-CPD using the acid test.

A clean and sterile 2.5L bioreactor (BioFlo3000 bioreactor, controlled via AFS-BioCommand software; New Brunswick Scientific Co., Inc. New Jersey, USA) was charged with 2.5 kg Crepetrol® 80E resin (26.6% TS) obtained from Hercules Voreppe plant, France. The resin was pH adjusted to pH 7.5 with a concentrated NaOH (33%/o) solution, supplemented with 25 ml nutrient solution and 0.04% PPG2000 (antifoam). The nutrient solution contained the following components per L sterilized demi water: 33 g Urea, 5 g KH2PO4, 5 g $MgSO_4.0.7H_2O$ and 1 g $CaCl_2.0.2H2O$. Aliquots of concentrated starter cultures of A. histidinolovorans (HK1) and A. radiobacter (HK7) were removed from the −80° C. freezer and thawed in a waterbath for 1-2 min. at 30° C. To start simultaneously the enzyme and biodehalogenation process, the following enzyme/bacteria amounts were added to the supplemented resin:

12.5 g Alcalase® 2.5L DX (Novozymes)
0.83 ml A. histidinolovorans (HK1) starter culture
4.17 ml A. radiobacter (HK7) starter culture Parameters settings for the bioreactor control unit, operated in batch mode, were initially set for the "enzyme treatment phase" as follows:

pH controlled at pH 7.5 (PID controlled addition of 25% NaOH solution)
Temperature controlled at 25° C.
Stirrer speed 600 rpm (maximum speed of 800 rpm; via DO value controlled)
Aeration set at 1.0 vvm (2.5L/min; compressed air), minimal DO value set at 5% air saturation Samples were taken in time after 2, 4 and 6 hours to monitor epi residuals (table 12). Epi residuals were measured by GC. These samples (25 ml) were pH adjusted to pH 3.5 with concentrated sulphuric acid and stored at 4° C. for further analysis.

After 6 hrs incubation the pH of the batch was lowered to pH 5.8 with concentrated sulphuric acid and the incubation temperature was raised to 30° C. Parameters settings for the bioreactor control unit, operated in batch mode during the "biodehalogenation treatment phase", were set as follows:

pH controlled at pH 5.8 (PID controlled addition of 25% NaOH solution)
Temperature controlled at 30° C.
Stirrer speed 600 rpm (maximum speed of 800 rpm; via DO value controlled)
Aeration set at 1.0 vvm (2.5L/min; compressed air), minimal DO value set at 5% air saturation Complete removal of epi residuals from the bioreactor content was closely monitored in time, via analysis by gas chromatography (GC-XSD; table 12). After a total incubation time of 52 hours the batch culture was finished. The pH of the simultaneously enzyme treated and biodehalogenated resin was adjusted to pH 3.5 using concentrated sulphuric acid and the product was supplemented with 0.2% potassiumsorbate and 0.12% Proxel BD. A sample of finished product was used in an acid test to determine the polymer bound 3-CPD fraction. The pH of this sample (25 ml) was adjusted to pH 1.0 with concentrated sulphuric acid, subsequently the sample was incubated for 24 hours at 50° C. After incubation the pH was re-adjusted to pH 3.5 with a 33% NaOH solution. Epi residuals were determined via GC-XSD measurement (table 12).

TABLE 12

Epi residuals during simultaneous enzyme- and bio-treatment and after acid test.

| Treatment | Process Time (hrs) | 1,3-DCP (ppm) | 3-CPD (ppm) |
|---|---|---|---|
| Crepetrol ® 80 E 26.6% TS | 0 | 35 | 100 |
| "Enzyme" process conditions | 2 | nd | 141 |
|  | 4 | nd | 135 |
|  | 6 | nd | 132 |
| "Biodehalogenation" process conditions | 24 | <1 | 2 |
|  | 31 | nd | <1 |
|  | 48 | nd | <1 |
| Acid Test of C80E feed (control) |  | 38 | 188 |
| Acid Test of Product |  | nd | 18 |

Example 26

Biodehalogenation of Crepetrol® 80E Creping Agent (Also Known as Crepetrol® A3025)

Manufacture and Preparation Issues.

(1) Prepare a total of 3225L Crepetrol A3025 without preservative (Available from Hercules Incorporated, Wilmington, Del.)
(2) Cleaning SU2 reactors:
  Complete fill with hot water (90° C.), aeration and agitation on. Add caustic up to pH 11.
  Keep at 90° C. for 30 min.
  Drain hot/caustic reactor content into SU1 vessel.
(3) Cleaning SU1 vessel:
  Fill completely with hot (90° C.)/caustic water from SU2 reactor.
  Turn aeration and agitation on in SU1 vessel during cleaning/heating.

Drain content after 60 min.
Complete fill with hot water (90° C.) and drain (=$2^{nd}$ rinse) content of vessel.
Heat treat (steam) vessel outlets, connectors and all tubing used for free draining.

(4) Pasteurization of Crepetrol A3025:
Fill reactor SU2 with 3225L Crepetrol A3025 (26% TS) and heat feedstock to 80° C.
Turn aeration and agitation on in SU2 reactor during pasteurization procedure.
Keep feedstock for 15 min. at 80° C.
Drain 175L (hot) A3025 in pasteurized SU1 vessel.
Drain 2000L (hot) A3025 in pasteurized storage vessel(s).
Keep remaining 1050L pasteurized A3025 in SU2 reactor until further usage in SU2.
Turn aeration and agitation off.

(5) Use only pasteurized water (15 min. 90° C.) for dilution step in SU1.
(6) Add appropriate amounts of K4 nutrients in dry form (see below for nutrient amounts).
(7) Prepare 0.5 L sterile glycerol solution (161 grams glycerol/500 ml; sterilized 15 min. at 121° C.).

Scale-up 1 (SU1): Preparation of Resin Inoculum
(1) Clean and pasteurize SU1 vessel (see above).
(2) Use a 50% pasteurized and diluted feedstock in SU1 vessel: Charge SU1 vessel with 175L pasteurized Crepetrol A3025 (26% TS) and 175L pasteurized (15 min. 90° C.) water.
(3) Start agitation
(4) Adjust pH in SU1 to pH 5.8±0.2 with 30% sodium hydroxide.
(5) Start aeration reactor (0.5 vvm)
(6) Adjust and maintain temperature in SU1 at 30±1° C.
(7) Add K4 nutrient in dry form (via a clean container):

| Component | Concentration (g/L) | 350 L volume |
|---|---|---|
| Urea | 0.33 | 115.5 grams |
| $KH_2PO_4$ | 0.10 | 35.0 grams |

(8) Add 0.5L (161 g/500 ml) sterile glycerol solution (=460 ppm final conc.).
(9) Inoculate SU1 with both HK1 and HK7 starter (Applied inoculation density for HK1 1:3500 and HK7 1:700, inoculum:resin ratio). [See Example 24 for concentrated starter culture preparation.]
(10) Samples for measurement:
$OD_{600}$ every 2 hrs
DCP/CPD values at end SU1
(11) Incubate for 16-24 hrs at 30±1° C. and pH 5.8±10.2 (When necessary correct for pH increases).
(12) Transfer to SU2 when:
$OD_{600}$>0.5 or $OD_{600}$ values started to plateau Scale-Up 2
(1) Clean and pasteurize SU2 reactor (see above).
(2) Use 1050L pasteurized Crepetrol A3025 feedstock.
(3) Start agitation.
(4) Adjust pH in SU2 to pH 5.8±0.2 with 30% sodium hydroxide.
(5) Start aeration reactor (0.5 vvm).
(6) Adjust and maintain temperature in SU2 at 30±1° C.
(7) Add K4 nutrient in dry form (via a clean container):

| Component | Concentration (g/L) | 1050 L volume |
|---|---|---|
| Urea | 0.33 | 346.5 grams |
| $KH_2PO_4$ | 0.10 | 105.0 grams |

(8) Inoculate SU2 with 350L SU1 culture (inoculation density 25%) by gravity using a cleaned & pasteurized connector/tubing (see above).
(9) Samples for measurement:
$OD_{600}$ every 2 hrs.
DCP/CPD values at end of SU2.
(10) Incubate for 16-24 hrs at 30±1° C. and pH 5.8±0.2 (When necessary correct for pH increases).
(11) Start SU3 when:
DCP/CPD values<5 ppm or when Dissolved Oxygen level increases.
Incubation time>24 hrs.

Scale-Up 3
(1) "Pasteurized feedstock" in storage vessel(s):
Heat-treat (with steam) all equipment used for mixing of feedstock.
Adjust pH to pH 5.8±0.2 with 30% sodium hydroxide.
(2) Drain storage vessel(s) by gravity into SU2 reactor (via cleaned/pasteurized connector/tubing (see above)
(3) Increase aeration volume in accordance with increased volume (0.5 vvm)
(4) Control agitation and temperature (30° C. ±1° C.) at set values.
(5) Add K4 nutrient in dry form (via clean container) for 2000L volume increase:

| Component | Concentration (g/L) | 2000 L volume |
|---|---|---|
| Urea | 0.33 | 660 grams |
| $KH_2PO_4$ | 0.10 | 200 grams |

(6) Samples for measurement:
$OD_{600}$ every 2 hrs.
DCP/CPD values every 4 hrs.
Sample for acid test at end of SU3.
(7) Incubate for 16-24 hrs at 30±1° C. and pH 5.8±0.2 (When necessary correct for pH increases)
(8) Biodehalogenation process in SU3 completed when:
Total level of [DCP]+[CPD]<5 ppm.
(9) Product Finishing:
Adjust pH with concentrated sulfuric acid to pH 3.0±0.2
Add 2000 ppm (0.2%) potassium sorbate Drain finished product through 50-100-μm filter into fresh tote bins.

Results: EPI—Residuals Analysis

Table 13; Results Epi-residual determination by GC-FID.

| Sample | EPI [ppm] | 1,3-DCP [ppm] | 2,3-DCP [ppm] | 3-CPD [ppm] |
|---|---|---|---|---|
| Crepetrol 80E feedstock | ND | 42 | ND | 131 |
| This example | ND | ND | ND | ND |
| Crepetrol 80E feedstock after acid test | ND | 38 | ND | 227 |

-continued

| Sample | EPI [ppm] | 1,3-DCP [ppm] | 2,3-DCP [ppm] | 3-CPD [ppm] |
|---|---|---|---|---|
| This example after acid test | ND | ND | ND | 56 |

ND = Not Detected
Detection Limits:
EPI [ppm]:     10,
1,3-DCP [ppm]: 10,
2,3-DCP [ppm]: 10,
3-CPD [ppm]:   10.

Example 27

Biodehalogenation of Kymene® SLX2 with Increasing % TS

A clean and sterile 500 ml flask was charged with 380 g Kymene® SLX2 (25.3% TS) obtained from Hercules Zwijndrecht plant, The Netherlands. The pH of the resin was adjusted to pH 5.8 by gradual addition (while vigorous mixing) of 8.3 g 33% NaOH solution. A series of sterilized 250 ml Erlenmeyer flasks was charged with 50 ml batches of resin with increasing %TS. Dilutions of the resin were made using sterilized deminerilized water (table 14).

TABLE 14

Kymene® SLX2 dilution range.

| Sample (% TS) | Kymene® SLX2 (ml) | Demi water (ml) |
|---|---|---|
| 8 | 15.8 | 34.2 |
| 10 | 19.8 | 30.2 |
| 12 | 23.7 | 26.3 |
| 14 | 27.7 | 22.3 |
| 16 | 31.6 | 18.4 |
| 18 | 35.6 | 14.4 |
| 20 | 39.5 | 10.5 |
| 25.3 | 50 | 0 |

Prior inoculation, each diluted resin sample was supplemented with 0.5 ml filter sterilized nutrient solution. The nutrient solution contained the following components per L sterilizaed demi water: 33 g Urea, 5 g $KH_2PO_4$, 5 g $MgSO_4.7H_2O$ and 1 g $CaCl_2.0.2$ 1 ml sample of concentrated starter cultures of both *A. histidinolovorans* (HK1) and *A. radiobacter* (HK7) was removed from the −80° C. freezer and thawed in a waterbath for 1-2 min. at 30° C. An 20 μl aliquot of the *A. histidinolovorans* (HK1) suspension and 100 μl aliquot of the *A. radiobacter* (HK7) suspension were both used to inoculate the described 50 ml dilutions of supplemented Kymene® SLX2. After inoculation, the cultures were incubated for 22 hours at 30° C. in a rotary-shaking incubator (250 rpm; G25 model; New Brunswick Scientific Co., Inc. New Jersey, USA). Bacterial growth was followed in time and determined by measuring the optical density at a wavelength of 600 mm using an Ultrospec 1000 UV/Vis spectrophotometer (Pharmacia Biotech, Sweden) and a 3 ml disposable cuvet with 1-cm pathlength (table 8). Samples were pH adjusted to pH 2.8 using concentrated sulfuric acid and 0.1% Proxel BD was added. Samples were measured for EPI residuals (3-CPD and 1,3-DCP) analysis by GC (table 15).

TABLE 15

Bacterial growth in Kymene® SLX2 with increasing % TS.

| Sample (% TS) | $OD_{600\ nm}$ | | | t = 22 hrs incubation | | "Viscosity" |
|---|---|---|---|---|---|---|
| | 0 hrs | 17 hrs | 22 hrs | 3-CPD (ppm) | 1,3-DCP (ppm) | appearance |
| 8 | 0.141 | 0.655 | 0.654 | <10 | <10 | − |
| 10 | 0.126 | 0.742 | 0.717 | <10 | <10 | − |
| 12 | 0.122 | 0.797 | 0.762 | <10 | <10 | − |
| 14 | 0.114 | 0.705 | 0.769 | <10 | 32 | − |
| 16 | 0.107 | 0.609 | 0.623 | <10 | 294 | + |
| 18 | 0.094 | 0.556 | 0.560 | <10 | 407 | + + |
| 20 | 0.096 | 0.486 | 0.541 | <10 | 492 | + + |
| 25.3 | 0.095 | 0.139 | 0.130 | gelled | gelled | + + + |

−: non-viscous, similiar to starting material.
+: viscous, increased viscosity compared to starting material.
++: very viscous, strongly increased viscosity compared to starting material.
+++: gelled resin.
Limit of detection:
10 ppm 1,3-DCP.
10 ppm 3-CPD.

Example 28

Biodehalogenation of Kymene® E7220 (Acid Treated Material) with Increasing % TS

A clean and sterile 500 ml flask was charged with 300 g Kymene® E7220 (22.5% TS) obtained from Hercules Voreppe plant, France. The pH of the resin was adjusted to pH 7.0 by gradual addition (while vigorous mixing) of 15.3 g 33% NaOH solution. A series of sterilized 250 ml Erlenmeyer flasks was charged with 50 ml batches of resin with increasing % TS. Dilutions of the resin were made using sterilized demineralized water (table 16).

TABLE 16

Kymene® E7220 dilution range.

| Sample (% TS) | Kymene® E7220 (ml) | Demi water (ml) |
|---|---|---|
| 8 | 17.8 | 32.2 |
| 10 | 22.2 | 27.8 |
| 12 | 26.7 | 23.3 |
| 14 | 31.1 | 18.9 |
| 16 | 35.6 | 14.4 |
| 18 | 40.0 | 10.0 |
| 20 | 44.4 | 5.6 |
| 22.5 | 50 | 0 |

Prior inoculation, each diluted resin sample was supplemented with 0.5 ml filter sterilized nutrient solution. The nutrient solution contained the following components per L sterililzed demi water: 33 g Urea, 5 g $KH_2PO_4$, 5 g $MgSO_4.7H_2O$ and 1 g $CaCl_2.0.2$ 1 ml sample of concentrated starter cultures of both *A. histidinolovorans* (HK1) and *A. radiobacter* (HK7) was removed from the −80° C. freezer and thawed in a waterbath for 1-2 min at 30° C. An 20 μl aliquot of the *A. histidinolovorans* (HK1) suspension and 100 μl aliquot of the *A. radiobacter* (HK7) suspension were both used to inoculate the described 50 ml dilutions of supplemented Kymene® E7220. After inoculation (start $OD_{600}$=0.208), the cultures were incubated for 91 hours at 30° C. in a rotary-shaking incubator (250 rpm; G25 model;

New Brunswick Scientific Co., Inc. New Jersey, USA). Bacterial growth was followed in time and determined by measuring the optical density at a wavelength of 600 nm using an Ultrospec1000 UV/Vis spectrophotometer (Pharmacia Biotech, Sweden) and a 3 ml disposable cuvet with 1-cm pathlength (table 17). Samples were pH adjusted to pH 2.8 using concentrated sulfuric acid and 0.1% Proxel BD was added. Samples were measured for EPI residuals (3-CPD and 1,3-DCP) by GC analysis (table 17).

TABLE 17

Bacterial growth in Kymene ® E7220 with increasing % TS

| Sample (% TS) | $OD_{600\ nm}$ | | | t = 91 hrs incubation | | |
|---|---|---|---|---|---|---|
| | 19 hrs | 27 hrs | 91 hrs | 3-CPD (ppm) | 1,3-DCP (ppm) | "Viscosity" appearance |
| 8 | 1.103 | 1.073 | nd | <10 | <10 | − |
| 10 | 1.190 | 1.168 | nd | <10 | <10 | − |
| 12 | 1.145 | 1.205 | nd | <10 | <10 | − |
| 14 | 0.870 | 1.237 | nd | <10 | <10 | − |
| 16 | 0.500 | 1.197 | 1.025 | <10 | <10 | − |
| 18 | 0.276 | 0.647 | 1.095 | <10 | <10 | − |
| 20 | 0.195 | 0.290 | 1.176 | <10 | <10 | − |
| 25.3 | 0.139 | 0.140 | 1.067 | <10 | 49 | − | nd: not determined
−: non-viscous, similiar to starting material.
+: viscous, increased viscosity compared to starting material.
++: very viscous, strongly increased viscosity compared to starting material.
+++: gelled resin.
Limit of detection:
10 ppm 1,3-DCP.
10 ppm 3-CPD.

Example 29

Biodehalogenation of Kymene® 736 (Polyamine/Azetidinium Based Resin) at 15-20% TS in 50 ml Batch Kymene® 736 (Crepetrol® 73) creping aid resin (39.6% TS as received), a polyamine/azetidinium-based resin available from Hercules Incorporated (Wilmington, Del.), was obtained from the Voreppe plant, France.

A clean and sterile 250 ml flask was charged with 100 g Kymene® 736 (39.6% TS) and the pH of the resin was adjusted to pH 7.0 by gradual addition (while vigorous mixing) of a 33% NaOH solution. Two sterile 250 ml Erlenmeyer flasks were charged with a 50 ml batch of resin diluted either to 15% or 20% TS. Dilutions of the resin were made using sterilized demineriliized water (table 18).

TABLE 18

Kymene ® 736 dilution range.

| Sample (% TS) | Kymene ® 736 (ml) | Demi water (ml) |
|---|---|---|
| 15 | 19.0 | 31.0 |
| 20 | 25.2 | 24.8 |

Prior inoculation, each diluted resin sample was supplemented with 0.5 ml filter sterilized nutrient solution. The nutrient solution contained the following components per L sterilized demi water: 33 g Urea, 5 g $KH_2PO_4$, 5 g $MgSO_4.0.7H_2O$ and 1 g $CaCl_2.0.2H2O$. A 1 ml sample of concentrated starter cultures of both *A. histidinolovorans* (HK1) and *A. radiobacter* (HK7) was removed from the −80° C. freezer and thawed in a waterbath for 1-2 min. at 30° C. An 50 µl aliquot of the *A. histidinolovorans* (HK1) suspension and 200 µl aliquot of the *A. radiobacter* (HK7) suspension were both used to inoculate the described 50 ml dilutions of supplemented Kymene® 736. After inoculation, the cultures were incubated for 43 hours at 30° C. in a rotary-shaking incubator (250 rpm; G25 model; New Brunswick Scientific Co., Inc. New Jersey, USA). Bacterial growth was followed in time and determined by measuring the optical density at a wavelength of 600 nm using an Ultrospec1000 UV/Vis spectrophotometer (Pharmacia Biotech, Sweden) and a 3 ml disposable cuvet with 1-cm pathlength (table 19). Samples were pH adjusted to pH 2.8 using concentrated sulfuric acid and 0.1% Proxel BD was added.

TABLE 19

Bacterial growth in Kymene ® 736 with increasing % TS.

| Time | $OD_{600\ nm}$ | |
|---|---|---|
| (hrs) | 15% TS | 20% TS |
| 0 | 0.441 | 0.378 |
| 20 | 0.935 | 0.419 |
| 23 | 1.081 | 0.430 |
| 41 | 0.997 | 0.910 |
| 43 | nd | 0.899 | nd: not determined

Example 30

Biodehalogenation of Kymene® 736 at 20% TS in 2L Batch

Kymene® 736 (Crepetrol® 73) creping aid resin (39.6% TS as received), a polyamine/azetidinium-based resin available from Hercules Incorporated (Wilmington, Del.), was obtained from the Voreppe plant, France.

A clean and sterile 2.5L bioreactor (BioFlo3000 bioreactor, controlled via AFS-BioCommand software; New Brunswick Scientific Co., Inc. New Jersey, USA) was charged with 1010 ml Kymene® 736 resin (39.6% TS) and 990 ml sterile demineralized water. The diluted (20% TS) resin was pH adjusted to pH 7.0 with a concentrated NaOH (33%) solution, supplemented with 20 ml nutrient solution and 0.0025% PPG2000 (antifoam). The nutrient solution contained the following components per L sterilized demi water: 33 g Urea, 5 g $KH_2PO_4$, 5 g $MgSO_4.0.7H_2O$ and 1 g $CaCl_2.0.2H2O$. Aliquots of concentrated starter cultures of *A. histidinolovorans* (HK1) and *A. radiobacter* (HK7) were removed from the −80° C. freezer and thawed in a waterbath for 1-2 min. at 30° C. A 2 ml sample of the *A. histidinolovorans* (HK1) suspension and 8 ml sample of the *A. radiobacter* (HK7) suspension was used to inoculate simultaneously the content of the 2.5 L bioreactor. Parameter settings of the bioreactor control unit, operated in batch mode, were as follows:

pH controlled at pH 7.0 (PID controlled addition of 25% NaOH solution)
Temperature controlled at 30° C.
Stirrer speed 600 rpm (maximum speed of 800 rpm; via DO value controlled)
Aeration set at 1.0 vvm (2.0L/min; compressed air), minimal DO value set at 5% air saturation
Complete removal of epi residuals from the bioreactor content was monitored in time, via analysis by gas chromatography (GC-XSD; table 20). After a total incubation time of 48 hours, the batch culture was finished. The pH of the biodehalogenated resin was adjusted to pH 2.8 using concentrated sulphuric acid and the resin was supplemented with 0.02% potassiumsorbate and 0.12% Proxel BD.

TABLE 20

Epi residuals and bacterial growth in Kymene ® 736 at 20% TS.

| Time (hrs) | $OD_{600\ nm}$ | 1,3-DCP (ppm) | 3-CPD (ppm) |
|---|---|---|---|
| 0 | 0.412 | — | — |
| 5 | 0.422 | — | — |
| 22 | 0.572 | — | — |
| 27 | 0.697 | — | — |
| 30 | 0.818 | <1 | 18 |
| 46 | 0.840 | <1 | <1 |

—: not determined

Example 31

Alcalase® Treatment of Tertiary Amine Based Resin

The following procedure has been used to promote 3-MCPD formation via hydrolysis of the polymer-bound chlorohydrin species in Crepetrol® A3025 (Hercules Incorporated, Wilmington, Del.).

A sample of 191.88 g of Crepetrol® A3025, containing no added preservatives was placed in a 250 glass flask, provided with a plastic, sealed screw cap. The weight of the sample was measured with a Mettler Laboratory digital scale with a precision of ±0.005 g. The total solid concentration of the Crepetrol® A3025 was determined in a separate experiment measuring the weight loss after 15 min at 150° C. The sample total solid concentration was found to be 26.9%.

The pH was carefully adjusted to 7.00 with a 10% w/w NaOH solution (total 12.52 g), while stirring with a magnetic stirrer, monitoring the pH with a Mettler pH-meter (MP 220), equipped with an InLab electrode (combination electrode, internal ref. ARGENTHAL with Ag ion trap). The pH meter was calibrated for the 7.00-10.00 pH range prior to the pH adjustment.

The sample was placed in an ice-melting bath (0° C.).

0.9 g of Alcalase® 2.5 L DX (obtained from Novozymes) were added to the Crepetrol®A3025 sample.

The flask was then placed in a horizontally shaking (200 strokes/min) thermostatic bath at 25° C., and left in agitation for 14 hours.

After 14 hours the sample was removed and the pH was adjusted with conc. $H_2SO_4$ to 3.5.

A sample of the original material (Crepetrol® A3025) and a sample of the material after the above treatment were analysed using a gas-chromatograpic technique to measure their content of 3-monochloropropandiol.

The amount of 3-monochloropropandiol produced during the treatment was calculated as the difference of 3-monochloropropandiol concentration of the sample after treatment and the original sample of Crepetrol® A3025.

The Reduced Viscosity of the final sample was also measured using an Ubbelohde capillary at 25° C. A 2% solution in 1N Ammonium Chloride was prepared and the time to flow through the capillary was measured. The time of flow of the Ammonium chloride solution was measured as well. Reduced viscosity was calculated according to the equation:

$$RSV\ [dl/g] = \{(time_{sample}[sec]/time_{solvent}[sec])-1\}/Conc_{sample}[g/100\ ml]$$

The results for CPD release were the following:

$$Released\ 3\text{-}MCPD\ [ppm] = Conc._{after\ treatment}[ppm] - Conc._{initial}[ppm] = 182 - 101.9 = 80.1\ ppm$$

In the following page is reported a table showing the results of a series of experiments performed with this procedure, changing the conditions of enzyme dosage, pH, total solid, temperature and duration of treatment.

The example given above corresponds to number 31-4 of table21.

TABLE 21

| #std (sample marking) | enzyme g | Alcalase Enzyme % weight | TS % | TS actual calc | temp deg C. | pH | time hs | RELEASED RATIO 3-MCPD | delta visc % | delta visc. in cP | RSV | delta RSV abs |
|---|---|---|---|---|---|---|---|---|---|---|---|---|
| 31-2  | 0.9   | 0.45   | 15   | 15.0 | 25   | 7   | 6  | 0.548 | −5.8  | −1.6 | 0.265 | −0.001 |
| 31-3  | 0.45  | 0.225  | 26   | 26.0 | 25   | 7   | 6  | 0.360 | −1.6  | −1.2 | 0.265 | −0.001 |
| 31-9  | 0.47  | 0.235  | 15   | 15.0 | 25   | 8   | 6  | 0.486 | −11.1 | −3.1 | 0.266 | 0 |
| 31-12 | 0.9   | 0.45   | 26   | 26.0 | 25   | 8   | 6  | 0.964 | 9.2   | 6.6  | 0.274 | 0.008 |
| 31-21 | 0.675 | 0.3375 | 20.5 | 20.5 | 25   | 7.5 | 10 | 0.729 | −16.8 | −7.6 | 0.261 | −0.005 |
| 31-1  | 0.45  | 0.225  | 15   | 15.0 | 25   | 7   | 14 | 0.568 | 3.9   | 1.1  | 0.265 | −0.001 |
| 31-11 | 0.45  | 0.2116 | 26   | 24.4 | 25   | 8   | 14 | 0.852 | 49.4  | 31.4 | 0.354 | 0.088 |
| 31-4  | 0.9   | 0.4384 | 26   | 25.3 | 25   | 7   | 14 | 0.974 | −0.5  | −0.4 | 0.266 | 0 |
| 31-10 | 0.9   | 0.45   | 15   | 15.0 | 25   | 8   | 14 | 0.938 | −4.7  | −1.3 | 0.27  | 0.004 |
| 31-25 | 0.675 | 0.3372 | 20.5 | 20.5 | 32.5 | 7.5 | 2  | 0.325 | −5.4  | −2.4 | 0.264 | −0.002 |
| 31-27 | 0.73  | 0.365  | 20.5 | 20.5 | 32.5 | 7.5 | 10 | 0.639 | −7.5  | −3.4 | 0.265 | −0.001 |
| 31-29 | 0.675 | 0.3375 | 20.5 | 20.5 | 32.5 | 7.5 | 10 | 0.519 | −16.8 | −7.6 | 0.267 | 0.001 |
| 31-23 | 0.675 | 0.3375 | 20.5 | 20.5 | 32.5 | 6.5 | 10 | 0.218 | −14.8 | −6.7 | 0.267 | 0.001 |
| 31-20 | 0.675 | 0.329  | 26   | 25.3 | 32.5 | 7.5 | 10 | 0.645 | −1.6  | −1.1 | 0.28  | 0.014 |
| 31-24 | 0.675 | 0.3375 | 20.5 | 20.5 | 32.5 | 8.5 | 10 | 0.579 | 81.0  | 36.5 | 0.453 | 0.187 |
| 31-30 | 0.675 | 0.3374 | 20.5 | 20.5 | 32.5 | 7.5 | 10 | 0.639 | −8.8  | −4.0 | 0.266 | 0 |
| 31-28 | 0.675 | 0.3375 | 20.5 | 20.5 | 32.5 | 7.5 | 10 | 0.444 | −9.5  | −4.3 | 0.27  | 0.004 |
| 31-19 | 0.675 | 0.3375 | 9.5  | 9.5  | 32.5 | 7.5 | 10 | 0.544 | −58.6 | −10.2 | 0.27 | 0.004 |
| 31-18 | 1.13  | 0.5649 | 20.5 | 20.5 | 32.5 | 7.5 | 10 | 0.910 | −6.2  | −2.8 | 0.262 | −0.004 |
| 31-17 | 0.21  | 0.105  | 20.5 | 20.5 | 32.5 | 7.5 | 10 | 0.203 | 13.8  | 6.2  | 0.272 | 0.006 |
| 31-26 | 0.675 | 0.3375 | 20.5 | 20.5 | 32.5 | 7.5 | 18 | 0.789 | −5.5  | −2.5 | 0.27  | 0.004 |
| 31-15 | 0.45  | 0.225  | 26   | 26.0 | 40   | 8   | 6  | 0.017 | 440.8 | 319.8 | 0.685 | 0.419 |
| 31-5  | 0.45  | 0.225  | 15   | 15.0 | 40   | 7   | 6  | 0.383 | −14.3 | −4.0 | 0.255 | −0.011 |

TABLE 21-continued

| #std (sample marking) | enzyme g | Alcalase Enzyme % weight | TS % calc | TS actual | temp deg C. | pH | time hs | RE- LEASED RATIO 3-MCPD | delta visc % | delta visc. in cP | RSV | delta RSV abs |
|---|---|---|---|---|---|---|---|---|---|---|---|---|
| 31-8 | 0.9 | 0.45 | 26 | 26.0 | 40 | 7 | 6 | 0.609 | 4.2 | 3.0 | 0.277 | 0.011 |
| 31-14 | 0.9 | 0.45 | 15 | 15.0 | 40 | 8 | 6 | 0.814 | 14.2 | 4.0 | 0.319 | 0.053 |
| 31-6 | 0.9 | 0.45 | 15 | 15.0 | 40 | 7 | 14 | 0.938 | — 12.2 | −3.4 | 0.268 | 0.002 |
| 31-7 | 0.45 | 0.225 | 26 | 26.0 | 40 | 7 | 14 | 0.680 | 24.0 | 17.4 | 0.31 | 0.044 |
| 31-13 | 0.45 | 0.225 | 15 | 15.0 | 40 | 8 | 14 | 0.650 | 93.8 | 26.3 | 0.53 | 0.264 |
| 31-16 | 0.9 | 0.45 | 26 | 26.0 | 40 | 8 | 14 | na | gelled | gelled | 1 | 0.734 |
| 31-22 | 0.675 | 0.337 | 20.5 | 20.5 | 47.5 | 7.5 | 10 | 0.189 | 12.5 | 5.6 | 0.306 | 0.04 |

According to the result reported is statistically calculated that the best conditions for the enzyme treatment of this resin are:

| | |
|---|---|
| Enzyme conc, [% W]: | 0.45 |
| TS polymer [%]: | 22.17 |
| Temp [°] | 25 |
| pH | 7.94 |
| Duration [hs] | 10.43 |

This treatment will result in a high release of 3-MCPD (ca. 95%) and in no increase in final viscosity. (Higher final viscosity is a problem for product stability, especially if additional treatment of the resin is required).

According to the statistical model elaborated, alternative conditions can be chosen when required resulting in similar final efficiency. The following conditions for example where an even lower amount of enzyme is used, and a final release of ca.90% of 3-MCPD is expected with no significant viscosity increase.

| | |
|---|---|
| Enzyme conc, [% W]: | 0.25 |
| TS polymer [%]: | 22.4 |
| Temp [°] | 25 |
| pH | 8.00 |
| Duration [hs] | 14.00 |

Example 32

Adhesion Measurements Results

In the following chart are reported the results of the adhesion measurement of a selected number of enzyme treated samples (extracted from the series reported in the table above). Significant hydrolysis (and consequent drop in average MW) of the polymer can result in significant peel strength loss, so we wanted to check if any important drop in adhesion was detectable.

Peel test was measured by soaking a strip of fabric in a 2% solids solution of the creping aid and then curing the strip for 7,5 minutes at 92° C. in contact with a standard metal plate (mild steel). The average force to peel away the strip from the plate was measured using a Zwick005 universal testing machine.

Results are plotted against the observed viscosity variation after enzyme treatment. Is clearly visible that the adhesion of the sample is distributed randomly (with an oscillation due to experimental variation), independently from the observed change in viscosity.

Furthermore the values are all distributed around the typical value for the untreated material (0.75-0.8 N/cm)

These results indicate that the enzyme treatments didn't cause any measurable decrease in the adhesion strength of the polymer.

TABLE 22

| std# | peel strength N/cm | Delta RSV |
|---|---|---|
| 31-4 | 0.7 | 0 |
| 31-10 | 0.65 | 0.004 |
| 31-11 | 0.71 | 0.088 |
| 31-12 | 0.75 | 0.008 |
| 31-21 | 0.72 | −0.005 |
| 31-18 | 0.81 | −0.004 |
| 31-24 | 0.82 | 0.187 |
| 29 | 0.74 | 0.001 |
| 5 | 0.76 | −0.011 |
| 6 | 0.93 | 0.002 |
| 13 | 0.69 | 0.264 |
| 14 | 0.77 | 0.053 |
| 15 | 0.74 | 0.419 |

Example 33

Biodehalogenation of Crepetrol® 870 (see Table 23 for Data and Details)

A portion of Crepetol® 870 without biocide (Available from Hercules Incorporated, Wilmington, Del.; Voreppe, France plant) was diluted to 18.9% total solids with deionized water. This diluted resin had a Brookfield viscosity of 53 cps.

Pasteurization:

A 2-L round-bottom flask was fitted with a condenser, a temperature controlled circulating bath and a mechanical stirrer. To the flask was added 1780 g of the 18.9% resin. The resin had a pH of 4.6 and was heated over one hour from 25° C. to 85° C. The resin was held at 85° C. for 20 minutes and then cooled to 25° C. in 45 minutes. The pasteurized resin was stored in a sterile container.

Biodehalogenation:

Preparation of resin inoculum [Scale-up 1 (SU1)]: A 250-mL round-bottom flask was fitted with a condenser, a pH meter, a temperature controlled circulating bath, an air sparge tube and a mechanical stirrer. A portion of the pasteurized resin was diluted to 10% with sterile, deionized water. To the flask was added 198 g of this 10% resin and 2.0 g of 5 mM sterile glycerol in water solution. The pH was raised to 5.8 with 3.18 g of 30% aqueous sodium hydroxide and then 68 microliters of HK1 concentrated starter culture was added (1:3000, HK1 to resin) [See Example 24 for concentrated starter culture preparation] and 1.75 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 17 hours, the resulting resin was used as inoculum for SU2.

Scale-Up 2 (SU2):

A 250-mL round-bottom flask was fitted with a condenser, a pH meter, a temperature controlled circulating bath, an air sparge tube and a mechanical stirrer. To the flask was added 150 g of the pasteurized 18.9% resin. The pH was raised to 5.8 with 4.52 g of 30% aqueous sodium hydroxide and then 50.0 g of the SU1 resin inoculum was added (25% inoculation rate) and 1.31 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was used as inoculum for SU3.

Scale-Up 3 (SU3):

A 250-mL round-bottom flask was fitted with a condenser, a pH meter, a temperature controlled circulating bath, an air sparge tube and a mechanical stirrer. To the flask was added 150 g of the pasteurized 18.9% resin. The pH was raised to 5.8 with 4.45 g of 30% aqueous sodium hydroxide and then 50.0 g of the SU2 resin inoculum was added (25% inoculation rate) and 1.31 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 m using a Spectronic® Genesys™ UV/Vis spectrophotometer (Spectronic Instruments, Incorporated, Rochester, N.Y., USA) and a disposable cuvet with 1-cm pathlength.

After 14.5 hours, the resulting resin was used as inoculum for SU4. The remaining resin not used for inoculum was discarded, but could have been used to give the finished product.

Scale-Up 4 (SU4):

A 500-mL round-bottom flask was fitted with a condenser, a pH meter, a temperature controlled circulating bath, an air sparge tube and a mechanical stirrer. To the flask was added 300 g of the pasteurized 18.9% resin. The pH was raised to 5.8 with 8.94 g of 30% aqueous sodium hydroxide and then 100.0 g of the SU3 resin inoculum was added (25% inoculation rate) and 2.62 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was used as inoculum for SU5. The remaining resin not used for inoculum was discarded, but could have been used to give the finished product.

Scale-Up 5 (SU5):

A 500-mL round-bottom flask was fitted with a condenser, a pH meter, a temperature controlled circulating bath, an air sparge tube and a mechanical stirrer. To the flask was added 300 g of the pasteurized 18.9% resin. The pH was raised to 5.8 with 8.96 g of 30% aqueous sodium hydroxide and then 100.0 g of the SU4 resin inoculum was added (25% inoculation rate) and 2.62 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength.

After 15.5 hours, the resulting resin was used as inoculum for SU6. The remaining resin not used for inoculum was converted to finished product by lowering the pH to 4.7 with 85% phosphoric acid and adding 2000 ppm of potassium sorbate as biocide.

Scale-Up 6 (SU6):

A 500-mL round-bottom flask was fitted with a condenser, a pH meter, a temperature controlled circulating bath, an air sparge tube and a mechanical stirrer. To the flask was added 300 g of the pasteurized 18.9% resin. The pH was raised to 5.8 with 8.84 g of 30% aqueous sodium hydroxide and then 100.0 g of the SU5 resin inoculum was added (25% inoculation rate) and 2.62 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was converted to finished product by lowering the pH to 4.7 with 7.20 g of 85% phosphoric acid and adding 2000 ppm of potassium sorbate (7.11 mL of 10 wt % aqueous potassium sorbate) as biocide.

See Table 23 for the results from monitoring the treatment.

TABLE 23

| Acid tests on Crepetrol 870 Sample | | DCP (ppm) | CPD (ppm) |
|---|---|---|---|
| X33047-19A | Voreppe before Pasteurization | ND | 47 |
| X33047-19A | After Acid Test | ND | 71 |
| X33047-39 | Voreppe after Pasteurization | ND | 43 |
| X33047-39 | After Acid Test | ND | 69 |

| Sample | Time (hours) | pH (30 C.) | OD$_{600}$ (abs.) | 30% NaOH (g) | DCP (ppm) | CPD (ppm) |
|---|---|---|---|---|---|---|
| Scale-up 1: 198 g 10% Crepetrol 870, 2 g 0.5 M glycerol, 68 microliters HK1, 1.75 g nutrient solution. | | | | | | |
| — | 0 | 5.81 | — | 3.18 | ND | 23 |
| X33047-41-1 | 1 | 5.81 | 0.020 | — | ND | 24 |
| X33047-41-2 | 17 | 5.82 | 0.473 | — | 0.26 | 0.08 |
| Scale-up 2: 150 g 18.87% Crepetrol 870, 50.0 g –41, 1.31 g nutrient solution. | | | | | | |
| — | 0 | 5.82 | — | 4.52 | ND | 32 |
| X33047-43-1 | 1 | 5.82 | 0.126 | — | ND | 28 |
| X33047-43-2 | 4 | 5.83 | 0.159 | — | 1.0 | 1.12 |
| X33047-43-3 | 8 | 5.82 | 0.168 | — | 0.57 | 0.50 |
| Scale-up 3: 150 g 18.87% Crepetrol 870, 50.0 g –43, 1.31 g nutrient solution. | | | | | | |
| — | 0 | 5.81 | — | 4.45 | ND | 32 |
| X33047-45-1 | 0.117 | 5.81 | 0.048 | — | ND | 29 |
| X33047-45-2 | 14.5 | 5.81 | 0.093 | — | 0.56 | 0.49 |
| Scale-up 4: 300 g 18.87% Crepetrol 870, 100.0 g –45, 2.62 g nutrient solution. | | | | | | |
| — | 0 | 5.82 | — | 8.94 | ND | 32 |
| X33047-47-1 | 0.25 | 5.82 | 0.029 | — | ND | 30 |
| X33047-47-2 | 4.25 | 5.82 | 0.067 | — | 0.58 | 0.30 |
| X33047-47-3 | 8 | 5.81 | 0.065 | — | 0.59 | 0.72 |

| Sample | Time (hours) | PH (30C) | OD$_{600}$ (abs.) | 30% NaOH (g) | DCP (ppm) | CPD (ppm) |
|---|---|---|---|---|---|---|
| Scale-up 5: 300 g 18.87% Crepetrol 870, 100.0 g –47, 2.62 g nutrient solution. | | | | | | |
| — | 0 | 5.81 | — | 8.96 | ND | 32 |
| X33047-49-1 | 0.083 | 5.81 | 0.053 | — | ND | 33 |
| X33047-49-2 | 15.5 | 5.80 | 0.049 | — | 0.6 | 0.12 |
| X33047-49 | Acid test | | | | ND | 29 |
| Scale-up 6: 300 g 18.87% Crepetrol 870, 100.0 g –49, 2.62 g nutrient solution. | | | | | | |
| — | 0 | 5.80 | — | 8.84 | ND | 32 |
| X33047-51-1 | 0.083 | 5.80 | 0.023 | — | ND | 32 |
| X33047-51-2 | 4 | 5.80 | 0.039 | — | ND | 8.7 |
| X33047-51-3 | 8 | 5.80 | 0.050 | — | 0.59 | 1.0 |
| X33047-51 | Acid test | | | | ND | 30 |

Example 34

Adhesion Testing for Creping Agents

A device for evaluating the adhesive properties of potential creping adhesives has been constructed. This apparatus consists of a heated cast iron block that is mounted on the actuator of a MTS test instrument. This platen is heated to 120° C. A paper sample is attached to the upper platen of the load cell of the test instrument with double sided tape. To perform the test, a known quantity of an aqueous solution of creping adhesive with a known concentration is sprayed onto the heated block. This is accomplished by using an airbrush that has been fitted with a volumetric spray bottle. The volumetric spray bottle allows one to accurately measure the volume of solution that is to be applied to the test platen. Our standard test conditions use a volume of 1.2 mL of a 4.0% solids aqueous solution. The pH of the solution can be ambient or can be adjusted to 7.0 prior to testing. After the resin solution is sprayed onto the heated block, the actuator is raised to contact the heated block to the paper sample with a force of 10 kg. The actuator is then lowered and the force to pull the platen away from the paper that it has contacted. This measured force is the adhesion value of the particular resin being tested. Since the applied force is not always exactly 10 kg the adhesion value is normalized to account for slight variations in the applied force. This is accomplished by multiplying the measured adhesion value by [10/(Applied force in kg)]. The paper used for testing is a 40 lb. basis weight sheet prepared from a 50/50 hardwood/softwood bleached Kraft furnish.

The following table contains Adhesion test and Brookfield viscosity data:

TABLE 24

| Designation | | Viscosity (cps) | Test (Kgs) (ambient pH) | Test (Kgs) (pH 7.0) |
|---|---|---|---|---|
| X33047-19A | Comp. Ex. | 53 | 23.4 | 21.7 |
| X33047-39 | Comp. Ex. | 54 | 23.4 | 23.2 |
| X33047-47 | Example | 45 | — | — |
| X33047-49 | Example | 46 | 21.6 | 22.1 |
| X33047-51 | Example | 49 | 23.7 | 22.2 |

The data in this table indicate that the present invention has viscosity and Adhesion Tests comparable to the untreated resins, indicating the performance of the biodehalogenated resins is comparable to the resins that were not biodehalogenated.

Example 35

Alcalase-Biodehalogenation of Crepetrol® 870 (see Table 25 for Data and Details)

A portion of Crepetrol® 870 without biocide (Available from Hercules Incorporated, Wilmington, Del.; Voreppe, France plant) was diluted to 18.7% total solids with deionized water. This diluted resin had a Brookfield viscosity of 53 cps.

Pasteurization:

A 2-L round-bottom flask was fitted with a condenser, a temperature controlled circulating bath and a mechanical stirrer. To the flask was added 2942 g of the 18.7% resin. The resin had a pH of 4.6 and was heated over 1.5 hour from 25° C. to 85° C. The resin was held at 85° C. for 20 minutes and then cooled to 25° C. in 30 minutes. The pasteurized resin was stored in a sterile container.

Biodehalogenation:

Preparation of resin inoculum [Scale-up 1 (SU1)]: A 250-mL round-bottom flask was fitted with a condenser, a pH meter, a temperature controlled circulating bath, an air sparge tube and a mechanical stirrer. A portion of the pasteurized resin was diluted to 10% with sterile, deionized water. To the flask was added 198 g of this 10% resin and 2.0 g of 5 mM sterile glycerol in water solution. The pH was raised to 7.2 with 8.31 g of 30% aqueous sodium hydroxide and then 68 microliters of HK1 concentrated starter culture was added (1:3000, HK1 to resin) [See Example 24 for concentrated starter culture preparation] and 1.75 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 16 hours, the resulting resin was used as inoculum for SU2.

Scale-Up 2 (SU2):

A 250-mL round-bottom flask was fitted with a condenser, a pH meter, a temperature controlled circulating bath, an air sparge tube and a mechanical stirrer. To the flask was added 150 g of the pasteurized 18.7% resin. The pH was raised to 7.2 with 10.97 g of 30% aqueous sodium hydroxide and then 1.02 g of Alcalase 2.5L type DX (available from Novozymes), 50.0 g of the SU1 resin inoculum (25% inoculation rate) and 1.31 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was used as inoculum for SU3.

Scale-Up 3 (SU3):

A 250-mL round-bottom flask was fitted with a condenser, a pH meter, a temperature controlled circulating bath, an air sparge tube and a mechanical stirrer. To the flask was added 150 g of the pasteurized 18.7% resin. The pH was raised to 7.2 with 11.42 g of 30% aqueous sodium hydroxide and then 0.87 g of Alcalase 2.5L type DX (available from Novozymes), 50.0 g of the SU2 resin inoculum (25% inoculation rate) and 1.31 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 μm using a Spectronic® Genesys™ UV/Vis spectrophotometer (Spectronic Instruments, Incorporated, Rochester, N.Y., USA) and a disposable cuvet with 1-cm pathlength. After 14 hours, the resulting resin was used as inoculum for SU4. The remaining resin not used for inoculum was discarded, but could have been used to give the finished product.

Scale-Up 4 (SU4):

A 500-mL round-bottom flask was fitted with a condenser, a pH meter, a temperature controlled circulating bath, an air sparge tube and a mechanical stirrer. To the flask was added 300 g of the pasteurized 18.7% resin. The pH was raised to 7.2 with 22.17 g of 30% aqueous sodium hydroxide and then 1.73 g of Alcalase 2.5L type DX (available from Novozymes), 100.0 g of the SU3 resin inoculum (25% inoculation rate) and 2.62 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 μm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was used as inoculum for SU5. The remaining resin not used for inoculum was converted to finished product by lowering the pH to 4.7 with 85% phosphoric acid and adding 2000 ppm of potassium sorbate as biocide.

Scale-Up 5 (SU5):

A 500-mL round-bottom flask was fitted with a condenser, a pH meter, a temperature controlled circulating bath, an air sparge tube and a mechanical stirrer. To the flask was added 300 g of the pasteurized 18.7% resin. The pH was raised to 7.2 with 22.77 g of 30% aqueous sodium hydroxide and then 1.73 g of Alcalase 2.5L type DX (available from Novozymes), 100.0 g of the SU4 resin inoculum (25% inoculation rate) and 2.62 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 14.5 hours, the resulting resin was used as inoculum for SU6. The remaining resin not used for inoculum was converted to finished product by lowering the pH to 4.7 with 85% phosphoric acid and adding 2000 ppm of potassium sorbate as biocide.

Scale-Up 6 (SU6):

A 500-mL round-bottom flask was fitted with a condenser, a pH meter, a temperature controlled circulating bath, an air sparge tube and a mechanical stirrer. To the flask was added 300 g of the pasteurized 18.7% resin. The pH was raised to 7.2 with 23.02 g of 30% aqueous sodium hydroxide and then 1.73 g of Alcalase 2.5L type DX (available from Novozymes), 100.0 g of the SU5 resin inoculum (25% inoculation rate) and 2.62 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was converted to finished product by lowering the pH to 4.7 with 22.5 g of 85% phosphoric acid and adding 2000 ppm of potassium sorbate (7.69 mL of 10 wt % aqueous potassium sorbate) as biocide.

See Table 25 for the results from monitoring the treatment. Note that using this inoculation rate, the SU6 batch was not completely biodehalogenated within an 8 hour reaction time. A side-by-side experiment, with the same reaction times, using a 33% inoculation rate in the SU4 batch and a 50% inoculation rate in the SU5 and SU6 batches provide a complete biodehalogenation in the SU6 batch (see Table 26)

TABLE 25

| Sample | Time (hours) | pH (30 C.) | $OD_{600}$ (abs.) | 30% NaOH (g) | DCP (ppm) | CPD (ppm) |
|---|---|---|---|---|---|---|
| Scale-up 1: 198 g 10% Crepetrol 870, 2 g 0.5 M glycerol, 68 microliters HK1, 1.75 g nutrient solution. | | | | | | |
| — | 0 | 7.20 | — | 8.31 | ND | 23 |
| X33047-62-1 | 0.5 | 7.20 | 0.066 | — | ND | 23 |
| X33047-62-2 | 15.67 | 7.21 | 0.180 | — | ND | 3.3 |
| Scale-up 2: 150 g 18.73% Crepetrol 870, 50.0 g −62, 1.02 g of Alcalase, 1.31 g nutrient solution. | | | | | | |
| — | 0 | 7.18 | — | 10.97 | ND | 32 |
| X33047-64-1 | 1 | 7.16 | 0.180 | — | ND | 34 |
| X33047-64-2 | 4 | 7.19 | 0.199 | — | ND | 11 |
| X33047-64-3 | 8 | 7.18 | 0.253 | — | 0.41 | 0.48 |
| Scale-up 3: 150 g 18.73% Crepetrol 870, 50.0 g −64, 0.87 g of Alcalase, 1.31 g nutrient solution. | | | | | | |
| — | 0 | 7.21 | — | 11.24 | ND | 32 |
| X33047-66-1 | 0.083 | 7.21 | 0.207 | — | ND | 33 |
| X33047-66-2 | 13.75 | 7.17 | 0.299 | — | 0.42 | 0.25 |
| Scale-up 4: 300 g 18.73% Crepetrol 870, 100.0 g −66, 1.73 g of Alcalase, 2.62 g nutrient solution. | | | | | | |
| — | 0 | 7.23 | — | 22.17 | ND | 32 |
| X33047-68-1 | 1 | 7.21 | 0.196 | — | ND | 32 |
| X33047-68-2 | 4 | 7.20 | 0.228 | — | ND | 19 |
| X33047-68-3 | 8 | 7.20 | 0.260 | — | 0.47 | 0.46 |
| X33047-68 | After Acid Test | | | | 0.37 | 5.9 |
| Scale-up 5: 300 g 18.73% Crepetrol 870, 100.0 g −68, 1.73 g of Alcalase, 2.62 g nutrient solution. | | | | | | |
| — | 0 | 7.23 | — | 22.77 | ND | 32 |
| X33047-70-1 | 0.083 | 7.23 | 0.165 | — | ND | 34 |

TABLE 25-continued

| Sample | Time (hours) | pH (30 C.) | OD$_{600}$ (abs.) | 30% NaOH (g) | DCP (ppm) | CPD (ppm) |
|---|---|---|---|---|---|---|
| X33047-70-2 | 14.5 | 7.19 | 0.247 | — | 0.43 | 0.2 |
| X33047-70 | After Acid Test | | | | 0.35 | 2.9 |
| Scale-up 6: 300 g 18.73% Crepetrol 870, 100.0 g −70, 1.73 g of Alcalase, 2.62 g nutrient solution. | | | | | | |
| — | 0 | 7.24 | — | 23.02 | ND | 32 |
| X33047-72-1 | 1 | 7.23 | 0.195 | — | ND | 33 |
| X33047-72-2 | 4 | 7.22 | 0.208 | — | ND | 35 |
| X33047-72-3 | 8 | 7.22 | 0.233 | — | ND | 25 |

TABLE 26

| Sample | Time (hours) | pH (30C) | OD$_{600}$ (abs.) | 30% NaOH (g) | DCP (ppm) | CPD (ppm) |
|---|---|---|---|---|---|---|
| Scale-up 1: 198 g 10% Crepetrol 870, 2 g 0.5M glycerol, 68 microliters HK1, 1.75 g nutrient solution. | | | | | | |
| — | 0 | 7.20 | — | 8.20 | ND | 23 |
| X33047-63-1 | 0.5 | 7.19 | 0.073 | — | ND | 23 |
| X33047-63-2 | 15.67 | 7.17 | 0.185 | — | ND | 2.5 |
| Scale-up 2: 150 g 18.73% Crepetrol 870, 50.0 g −63, 1.02 g of Alcalase, 1.31 g nutrient solution. | | | | | | |
| — | 0 | 7.18 | — | 11.13 | ND | 32 |
| X33047-65-1 | 1 | 7.17 | 0.181 | — | ND | 32 |
| X33047-65-2 | 4 | 7.17-7.19 | 0.207 | 0.13 | ND | 10 |
| X33047-65-3 | 8 | 7.18 | 0.261 | — | 0.45 | 0.42 |
| Scale-up 3: 150 g 18.73% Crepetrol 870, 50.0 g −65, 0.87 g of Alcalase, 1.31 g nutrient solution. | | | | | | |
| — | 0 | 7.21 | — | 11.26 | ND | 32 |
| X33047-67-1 | 0.083 | 7.21 | 0.193 | — | ND | 31 |
| X33047-67-2 | 13.75 | 7.17 | 0.288 | — | 0.39 | 0.22 |
| Scale-up 4: 266.7 g 18.73% Crepetrol 870, 133.3 g −67, 1.54 g of Alcalase, 2.33 g nutrient solution. | | | | | | |
| — | 0 | 7.22 | — | 20.28 | ND | 29 |
| X33047-69-1 | 1 | 7.20 | 0.194 | — | ND | 24 |
| X33047-69-2 | 4 | 7.20 | 0.234 | — | 0.45 | 2.7 |
| X33047-69-3 | 8 | 7.19 | 0.258 | — | 0.41 | 0.35 |
| Scale-up 5: 200 g 18.73% Crepetrol 870, 200.0 g −69, 1.16 g of Alcalase, 1.75 g nutrient solution. | | | | | | |
| — | 0 | 7.22 | — | 15.08 | ND | 22 |
| X33047-71-1 | 0.083 | 7.22 | 0.199 | — | ND | 20 |
| X33047-71-2 | 14.5 | 7.20 | 0.278 | — | 0.38 | 0.13 |
| X33047-71 | After Acid Test | | | | 0.30 | 1.5 |
| Scale-up 6: 200 g 18.73% Crepetrol 870, 200.0 g −71, 1.16 g of Alcalase, 1.75 g nutrient solution. | | | | | | |
| — | 0 | 7.24 | — | 15.37 | ND | 22 |
| X33047-73-1 | 1 | 7.22 | 0.224 | — | ND | 16 |
| X33047-73-2 | 4 | 7.21 | 0.261 | — | 0.42 | 0.43 |
| X33047-73-3 | 8 | 7.21 | 0.271 | — | 0.41 | 0.21 |
| X33047-73 | After Acid Test | | | | 0.32 | 3.3 |

Example 36

Biodehalogenation of Crepetrol® A6115 (see Table BP4 for Data and Details)

A portion of Crepetrol® A6115 creping agent without biocide (Available from Hercules Incorporated, Wilmington, Del.; Milwaukee, Wis. plant) was filtered through a 100 mesh screen. The resin had 15.73% total solids, a pH of 5.1 and a Brookfield viscosity of 86 cps.

Pasteurization:

A 3-L round-bottom flask was fitted with a condenser, a temperature controlled circulating bath and a mechanical stirrer. To the flask was added 2770 g of the resin. The resin was heated over 1.5 hours from 25° C. to 85° C. The resin was held at 85° C. for 20 minutes and then cooled to 25° C. in 30 minutes. The pasteurized resin was stored in a sterile container.

Biodehalogenation:

Preparation of resin inoculum [Scale-up 1 (SU1)]: A 250-mL round-bottom flask was fitted with a condenser, a pH meter, a temperature controlled circulating bath, an air sparge tube and a mechanical stirrer. A portion of the pasteurized resin was diluted to 10% with sterile, deionized water. To the flask was added 198 g of this 10% resin and 2.0 g of 5 mM sterile glycerol in water solution. The pH was raised to 6.0 with 1.04 g of 30% aqueous sodium hydroxide and then 133 microliters of HK1 concentrated starter culture was added (1:1500, HK1 to resin) [See Example 24 for concentrated starter culture preparation] and 1.75 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density (OD$_{600}$) and the biodehalogenation was monitored by GC. OD$_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 16 hours, the resulting resin was used as inoculum for SU2.

Scale-Up 2 (SU2):

A 250-mL round-bottom flask was fitted with a condenser, a pH meter, a temperature controlled circulating bath, an air sparge tube and a mechanical stirrer. To the flask was added 150 g of the pasteurized resin. The pH was raised to 5.8 with 0.96 g of 30% aqueous sodium hydroxide and then 50.0 g of the SU1 resin inoculum was added (25% inoculation rate) and 1.31 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was used as inoculum for SU3.

Scale-Up 3 (SU3):

A 250-mL round-bottom flask was fitted with a condenser, a pH meter, a temperature controlled circulating bath, an air sparge tube and a mechanical stirrer. To the flask was added 150 g of the pasteurized resin. The pH was raised to 5.8 with 0.96 g of 30% aqueous sodium hydroxide and then 50.0 g of the SU2 resin inoculum was added (25% inoculation rate) and 1.31 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 14.5 hours, the resulting resin was used as inoculum for SU4. The remaining resin not used for inoculum was discarded, but could have been used to give the finished product.

Scale-Up 4 (SU4):

A 500-mL round-bottom flask was fitted with a condenser, a pH meter, a temperature controlled circulating bath, an air sparge tube and a mechanical stirrer. To the flask was added 300 g of the pasteurized resin. The pH was raised to 5.8 with 1.40 g of 30% aqueous sodium hydroxide and then 100.0 g of the SU3 resin inoculum was added (25% inoculation rate) and 2.62 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was used as inoculum for SU5. The remaining resin not used for inoculum was discarded, but could have been used to give the finished product.

Scale-Up 5 (SU5):

A 500-mL round-bottom flask was fitted with a condenser, a pH meter, a temperature controlled circulating bath, an air sparge tube and a mechanical stirrer. To the flask was added 300 g of the pasteurized resin. The pH was raised to 5.8 with 1.69 g of 30% aqueous sodium hydroxide and then 100.0 g of the SU4 resin inoculum was added (25% inoculation rate) and 2.62 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 15 hours, the resulting resin was used as inoculum for SU6. The remaining resin not used for inoculum was converted to finished product by lowering the pH to 5.3 with concentrate (96%) suliric acid and adding 2000 ppm of potassium sorbate as biocide.

Scale-Up 6 (SU6):

A 500-mL round-bottom flask was fitted with a condenser, a pH meter, a temperature controlled circulating bath, an air sparge tube and a mechanical stirrer. To the flask was added 300 g of the pasteurized resin. The pH was raised to 5.8 with 1.82 g of 30% aqueous sodium hydroxide and then 100.0 g of the SU5 resin inoculum was added (25% inoculation rate) and 2.62 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was converted to finished product by lowering the pH to 5.3 with 0.73 g of concentrated (96%) sulfuric acid and adding 2000 ppm of potassium sorbate (7.6 mL of 10 wt % aqueous potassium sorbate) as biocide.

See Table 27 for the results from monitoring the treatment.

Table 27:

TABLE 27

| Sample | Time (hours) | pH (30C) | Gardner Viscosity | $OD_{600}$ (abs.) | 30% NaOH (g) | DCP (ppm) | CPD (ppm) |
|---|---|---|---|---|---|---|---|
| Scale-up 1: 198 g 10% Crepetrol A6115 (pasteurized), 2 g 0.5M glycerol, 133 microliters HK1 (1:1500, resin: inoculum), 1.75 g nutrient solution. | | | | | | | |
| — | 0 | 5.96 | — | — | 1.04 | 1.7 | 30 |
| X32989-58-1 | 0.25 | 5.95 | — | 0.059 | — | ND | 30 |
| X32989-58-2 | 16 | 5.95 | — | 0.355 | — | 1.2 | 0.28 |

TABLE 27-continued

| Sample | Time (hours) | pH (30C) | Gardner Viscosity | OD$_{600}$ (abs.) | 30% NaOH (g) | DCP (ppm) | CPD (ppm) |
|---|---|---|---|---|---|---|---|
| Scale-up 2: 150 g 15.7% Crepetrol A6115 (pasteurized), 50.0 g −58, 1.31 g nutrient solution. | | | | | | | |
| — | 0 | 5.81 | — | — | 0.96 | 2.0 | 35 |
| X32989-60-1 | 1 | 5.81 | — | 0.134 | — | 2.0 | 0.50 |
| X32989-60-2 | 4 | 5.82 | — | 0.130 | — | 1.9 | 0.42 |
| X32989-60-3 | 8 | 5.83 | — | 1.24 | — | 1.9 | 0.58 |
| Scale-up 3: 150 g 15.7% Crepetrol A6115 (pasteurized), 50.0 g −60, 1.31 g nutrient solution. | | | | | | | |
| — | 0 | 5.81 | — | — | 0.96 | 2.0 | 35 |
| X32989-62-1 | 0.083 | 5.81 | — | 0.080 | — | ND | 28 |
| X32989-62-2 | 14.5 | 5.81 | — | 0.078 | — | 2.8 | 0.59 |
| Scale-up 4: 300 g 15.7% Crepetrol A6115 (pasteurized), 100.0 g −62, 2.62 g nutrient solution. | | | | | | | |
| — | 0 | 5.78 | — | — | 1.40 | 2.0 | 35 |
| X32989-64-1 | 1 | 5.77 | — | 0.064 | — | ND | 24 |
| X32989-64-2 | 4 | 5.76 | — | 0.050 | — | 2.3 | 0.39 |
| X32989-64-3 | 8 | 5.77 | — | 0.055 | — | 2.3 | 0.49 |
| Scale-up 5: 300 g 15.7% Crepetrol A6115 (pasteurized), 100.0 g −64, 2.62 g nutrient solution. | | | | | | | |
| — | 0 | 5.80 | — | — | 1.69 | 2.0 | 35 |
| X32989-66-1 | 0.083 | 5.76 | E | 0.054 | — | ND | 33 |
| X32989-66-2 | 15 | 5.76 | E | 0.042 | — | 2.3 | 0.55 |
| Scale-up 6: 300 g 15.7% Crepetrol A6115 (pasteurized), 100.0 g −66, 2.62 g nutrient solution. | | | | | | | |
| — | 0 | 5.77 | — | — | 1.82 | 2.0 | 35 |
| X32989-68-1 | 1 | 5.76 | E | 0.036 | — | ND | 24 |
| X32989-68-2 | 4 | 5.75 | — | 0.054 | — | 2.1 | 1.7 |
| X32989-68-3 | 8 | 5.75 | E | 0.039 | — | 2.2 | 0.41 |

Example 37

Alcalase-Biodehalogenation of Crepetrol® A6115 Creping Agent (see Table BP5 for Data and Details)

A portion of Crepetrol® A6 115 creping agent without biocide (Available from Hercules Incorporated, Wilmington, Del.; Milwaukee, Wis. plant) was filtered through a 100 mesh screen. The resin had 15.73% total solids, a pH of 5.1 and a Brookfield viscosity of 86 cps.

Pasteurization:

A 3-L round-bottom flask was fitted with a condenser, a temperature controlled circulating bath and a mechanical stirrer. To the flask was added 2770 g of the resin. The resin was heated over 1.5 hours from 25° C. to 85° C. The resin was held at 85° C. for 20 minutes and then cooled to 25° C. in 30 minutes. The pasteurized resin was stored in a sterile container.

Biodehalogenation:

Preparation of resin inoculum [Scale-up 1 (SU1)]: A 250-mL round-bottom flask was fitted with a condenser, a pH meter, a temperature controlled circulating bath, an air sparge tube and a mechanical stirrer. A portion of the pasteurized resin was diluted to 10% with sterile, deionized water. To the flask was added 198 g of this 10% resin and 2.0 g of 5 mM sterile glycerol in water solution. The pH was raised to 7.2 with 2.65 g of 30% aqueous sodium hydroxide and then 0.62 g of Alcalase 2.5L type DX (available from Novozymes) and 133 microliters of HK1 concentrated starter culture was added (1:1500, HK1 to resin) [See Example 24 for concentrated starter culture preparation] and 1.75 g of a nutrient solution was added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density (OD$_{600}$) and the biodehalogenation was monitored by GC. OD$_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 16 hours, the resulting resin was used as inoculum for SU2.

Scale-Up 2 (SU2):

A 250-mL round-bottom flask was fitted with a condenser, a pH meter, a temperature controlled circulating bath, an air sparge tube and a mechanical stirrer. To the flask was added 150 g of the pasteurized resin. The pH was raised to 7.2 with 3.37 g of 30% aqueous sodium hydroxide and then 0.73 g of Alcalase 2.5L type DX (available from Novozymes), 50.0 g of the SU1 resin inoculum (25% inoculation rate) and 1.31 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was used as inoculum for SU3.

Scale-Up 3 (SU3):

A 250-niL round-bottom flask was fitted with a condenser, a pH meter, a temperature controlled circulating bath, an air sparge tube and a mechanical stirrer. To the flask was added 150 g of the pasteurized resin. The pH was raised to 7.2 with 3.02 g of 30% aqueous sodium hydroxide and then 0.73 g of Alcalase 2.5L type DX (available from Novozymes), 50.0 g of the SU2 resin inoculum (25% inoculation rate) and 1.31 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 14.5 hours, the resulting resin was used as inoculum for SU4. The remaining resin not used for inoculum was discarded, but could have been used to give the finished product.

Scale-Up 4 (SU4):

A 500-mL round-bottom flask was fitted with a condenser, a pH meter, a temperature controlled circulating bath, an air sparge tube and a mechanical stirrer. To the flask was added 300 g of the pasteurized % resin. The pH was raised to 7.2 with 6.03 g of 30% aqueous sodium hydroxide and then 1.46 g of Alcalase 2.5L type DX (available from Novozymes), 100.0 g of the SU3 resin inoculum (25% inoculation rate) and 2.62 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nrm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was used as inoculum for SU5. The remaining resin not used for inoculum was discarded, but could have been used to give the finished product.

Scale-Up 5 (SU5):

A 500-mL round-bottom flask was fitted with a condenser, a pH meter, a temperature controlled circulating bath, an air sparge tube and a mechanical stirrer. To the flask was added 300 g of the pasteurized resin. The pH was raised to 7.2 with 6.26 g of 30% aqueous sodium hydroxide and then 1.46 g of Alcalase 2.5L type DX (available from Novozymes), 100.0 g of the SU4 resin inoculum (25% inoculation rate) and 2.62 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 15 hours, the resulting resin was used as inoculum for SU6. The remaining resin not used for inoculum was converted to finished product by lowering the pH to 5.3 with concentrated (96%) sulfuric acid and adding 2000 ppm of potassium sorbate as biocide.

Scale-Up 6 (SU6):

A 500-mL round-bottom flask was fitted with a condenser, a pH meter, a temperature controlled circulating bath, an air sparge tube and a mechanical stirrer. To the flask was added 300 g of the pasteurized resin. The pH was raised to 7.2 with 6.02 g of 30% aqueous sodium hydroxide and then 1.46 g of Alcalase 2.5L type DX (available from Novozymes), 100.0 g of the SU5 resin inoculum (25% inoculation rate) and 2.62 g of a nutrient solution were added. (The nutrient solution consisted of 8026 ppm of potassium dihydrogen phosphate, 27480 ppm of urea, 4160 ppm of magnesium sulfate and 840 ppm of calcium chloride in tap water.) The air sparge was started, the temperature was maintained at 30° C. The bacterial growth was monitored by optical density ($OD_{600}$) and the biodehalogenation was monitored by GC. $OD_{600}$ was determined by measuring the optical density at a wavelength of 600 nm using a Spectronic® Genesys™ UV/Vis spectrophotometer (Spectronic Instruments, Incorporated, Rochester, N.Y., USA) and a disposable cuvet with 1-cm pathlength. After 8 hours, the resulting resin was converted to finished product by lowering the pH to 5.3 with 2.92 g of concentrated (96%) sulfuric acid and adding 2000 ppm of potassium sorbate (7.6 mL of 10 wt % aqueous potassium sorbate) as biocide.

See Table 28 for the results from monitoring the treatment.

TABLE 28

| Sample | Time (hours) | PH (30C) | Gardner Viscosity | $OD_{600}$ (abs.) | 30% NaOH (g) | DCP (ppm) | CPD (ppm) |
|---|---|---|---|---|---|---|---|
| Scale-up 1: 198 g 10% Crepetrol A6115 (pasteurized), 2 g 0.5M glycerol, 0.62 g of Alcalase, 133 microliters HK1 (1:1500, resin: inoculum), 1.75 g nutrient solution. ||||||||
| — | 0 | 7.17 | — | — | 2.65 | 1.7 | 30 |
| X32989-59-1 | 0.25 | 7.16 | — | 0.058 | — | ND | 32 |
| X32989-59-2 | 16 | 7.17 | — | 0.450 | — | 0.57 | 0.12 |

TABLE 28-continued

| Sample | Time (hours) | PH (30C) | Gardner Viscosity | OD$_{600}$ (abs.) | 30% NaOH (g) | DCP (ppm) | CPD (ppm) |
|---|---|---|---|---|---|---|---|
| Scale-up 2: 150 g 15.7% Crepetrol A6115, 0.73 g Alcalase, 50.0 g −59, 1.31 g nutrient solution. | | | | | | | |
| — | 0 | 7.19 | — | — | 3.37 | 2.0 | 35 |
| X32989-61-1 | 1 | 7.18 | — | 0.167 | — | 1.7 | 3.6 |
| X32989-61-2 | 4 | 7.19 | — | 0.180 | — | 1.5 | 0.27 |
| X32989-61-3 | 8 | 7.18 | — | 0.183 | — | 1.4 | 0.24 |
| Scale-up 3: 150 g 15.7% Crepetrol A6115, 0.73 g Alcalase, 50.0 g −61, 1.31 g nutrient solution. | | | | | | | |
| — | 0 | 7.17 | — | — | 3.02 | 2.0 | 35 |
| X32989-63-1 | 0.083 | 7.16 | — | 0.087 | — | ND | 33 |
| X32989-63-2 | 14.5 | 7.16 | — | 0.130 | — | 1.5 | 0.22 |
| Scale-up 4: 300 g 15.7% Crepetrol A6115, 1.46 g Alcalase, 100.0 g −63, 2.62 g nutrient solution. | | | | | | | |
| — | 0 | 7.15 | — | — | 6.03 | 2.0 | 35 |
| X32989-65-1 | 1 | 7.13 | — | 0.079 | — | ND | 31 |
| X32989-65-2 | 4 | 7.12 | — | 0.095 | — | 1.9 | 0.59 |
| X32989-65-3 | 8 | 7.11 | — | 0.110 | — | 1.9 | 0.37 |
| Scale-up 5: 300 g 15.7% Crepetrol A6115, 1.46 g Alcalase, 100.0 g −65, 2.62 g nutrient solution. | | | | | | | |
| — | 0 | 7.20 | — | — | 6.26 | 2.0 | 35 |
| X32989-67-1 | 0.083 | 7.17 | C | 0.050 | — | ND | 35 |
| X32989-67-2 | 15 | 7.17 | C | 0.107 | — | 1.7 | 0.19 |
| Scale-up 6: 300 g 15.7% Crepetrol A6115, 1.46 g Alcalase, 100.0 g −67, 2.62 g nutrient solution. | | | | | | | |
| — | 0 | 7.16 | — | — | 6.02 | 2.0 | 35 |
| X32989-69-1 | 1 | 7.14 | C | 0.061 | — | 2.5 | 32 |
| X32989-69-2 | 4 | 7.13 | — | 0.099 | — | 1.9 | 1.1 |
| X32989-69-3 | 8 | 7.13 | C | 0.107 | — | 1.8 | 0.23 |

Example 38

High Solids, Simultaneous Enzyme-Biodehalogenation Treatment General Procedure:

Low molecular weight terpolymers of adipic acid, diethylenetriamine and acetic acid were prepared by condensing these reactants at 170° C. for three hours in a molar ratio of 1:0.9:0.2. The reaction products were diluted to 50% solids.

These polymers were reacted with epichlorohydrin at an epichlorohydrin:diethylenetriame ratio of 0.82 for 3.5 hours at 40° C., and water was added in such a way that the total solids content of the reactor was 40%.

In a next step, the reaction mixtures were diluted to a total solids content of 31% and heated to 68° C. for functionalization and crosslinking. Reactions were stopped at Gardner-Holt viscosity "I/J" after about two hours and 10 minutes at this temperature by the addition of 30% sulfuric acid in such a way that the pH after sulfuric addition was 4.5. The reaction products were cooled to room temperature, 1.75% of phosphoric acid (weight to reactor volume) was added and the pH adjusted after phosphoric acid addition using sulfuric acid to pH 2.7. The purpose of adding phosphoric and sulfuric acid to this pH is to obtain viscometrically stable resins.

The resins were analyzed for their residual organochlorine level and 1,3-DCP levels were found to be 816 ppm for the acetic acid containing material. These resins were tested in a paper trial and were found to be as effective as Kymene® SLX2 in imparting wet strength to paper. The resins were stored for 6 weeks at 32° C. and during this period gelation of the resins did not occur.

Biodehalogenation (see Table 29 for data and details): An inoculum was prepared with a non-end-capped resin (Kymene E7219) (see Scale-up 1 and Scale-up 2 in Table 29). The end-capped resin prepared above was diluted to 13.5% solids, the pH was raised to pH 7.2 with 30% aqueous sodium hydroxide, the catalyst (Alcalase, Novozymes) for hydrolyzing the CPD-forming species, the inoculum from Scale-up 2, and the nutrient solution were added. Not wishing to be bound by theory, it is believed that this low solids intermediate step is useful to improve the adaptation of the microbial population to the new resin. After biodehalogenation was complete, the next batch (Scale-up 4) was started. The end-capped resin prepared above was diluted to 20% solids, the pH was raised to pH 7.2 with 30% aqueous sodium hydroxide, the catalyst (Alcalase, Novozymes) for hydrolyzing the CPD-forming species, the inoculum from Scale-up 3 (20% inoculation rate), and the nutrient solution were added. The microbial growth was rapid, as indicated by optical density (OD$_{600}$) (see Scale-up 4 in Table 29). The biodehalogenation was also rapid, as indicated by the rapid loss of DCP and CPD.

TABLE 29

Alcalase-Biodehalogenation of a High Solids Wet-Strength Resin.

| Sample | Time | Time (hours) | pH @ 30C | Gardner Viscosity | $OD_{600}$ (abs.) | 30% NaOH (g) | DCP (ppm) | CPD (ppm) |
|---|---|---|---|---|---|---|---|---|
| Scale-up 1: 200 g 8% E7219 (pasteurized), No Alcalase, 400 microliters of HK7, 1.75 g nutrient solution. ||||||||| 
| — | 6:56 | 0 | 7.15 | — | — | 2.54 | — | — |
| X32966-3-1 | 7:58 | 1 | 7.14 | — | 0.171 | — | 213 | 143 |
| X32966-3-2 | 10:57 | 4 | 7.13 | — | 0.162 | — | 144 | 181 |
| X32966-3-3 | 13:58 | 7 | 7.08–7.25 | — | 0.162 | 0.11 | 62 | 235 |
| X32966-3-4 | 17:00 | 10 | 7.21 | — | 0.184 | — | ND | 274 |
| X32966-3-5 | 20:10 | 13 | 7.17 | — | 0.204 | — | ND | 228 |
| X32966-3-6 | 5:55 | 23 | 7.03 | — | 0.509 | — | ND | 2.6 |
| Scale-up 2: 350 g 13.5% E7219 (pasteurized), 5.03 g Alcalase, 87.5 g of –3, 3.06 g nutrient solution. |||||||||
| — | 6:40 | 0 | 7.23 | — | — | 7.31 | — | — |
| X32966-5-1 | 7:40 | 1 | 7.20 | — | 0.113 | — | 80 | 391 |
| X32966-5-2 | 10:41 | 4 | 7.04–7.21 | — | 0.149 | 0.33 | ND | 415 |
| X32966-5-3 | 13:30 | 7 | 7.19 | — | 0.248 | — | ND | 313 |
| X32966-5-4 | 16:50 | 10 | 7.11–7.27 | — | 0.383 | 0.31 | ND | 98 |
| X32966-5-5 | 20:40 | 14 | 7.28 | — | 0.475 | — | ND | 38 |
| X32966-5-6 | 5:59 | 23 | 7.17 | — | 0.573 | — | ND | 0.43 |

The final resin had a Brookfield Viscosity of 38 cps.

| Sample | Time | Time (hours) | pH @ 30C | Gardner Viscosity | $OD_{600}$ (abs.) | 30% NaOH (g) | DCP (ppm) | CPD (ppm) |
|---|---|---|---|---|---|---|---|---|
| Scale-up 3: 200 g 13.5% endcapped resin, 2.50 g Alcalase, 22.22 g of –5, 1.75 g nutrient solution. |||||||||
| — | 7:00 | 0 | 7.22 | — | — | 5.71 | — | — |
| X32966-11-1 | 8:01 | 1 | 7.18 | — | 0.059 | — | 270 | 343 |
| X32966-11-2 | 11:02 | 4 | 7.05–7.23 | — | 0.092 | 0.28 | 40 | 621 |
| X32966-11-3 | 14:01 | 7 | 7.17 | — | 0.165 | — | ND | 660 |
| X32966-11-4 | 17:00 | 10 | 7.15–7.31 | — | 0.277 | 0.15 | ND | 627 |
| X32966-11-5 | 5:50 | 23 | 7.11 | — | 0.772 | — | ND | 0.4 |
| Scale-up 4: 160 g 20% endcapped resin, 3.00 g Alcalase, 40.0 g of –11, 1.40 g nutrient solution. |||||||||
| — | 6:56 | 0 | 7.25 | — | — | 6.09 | — | — |
| X32966-15-1 | 8:00 | 1 | 7.21 | A-B | 0.148 | — | 406 | 393 |
| X32966-15-2 | 12:15 | 5.3 | 7.06–7.23 | A-A-1 | 0.346 | 0.27 | 283 | 586 |
| X32966-15-3 | 17:45 | 10.6 | 7.03–7.16 | A-A-1 | 0.728 | 0.23 | 86 | 14 |
| X32966-15-4 | 9:30 | 26.5 | 7.06 | A-A-1 | 0.962 | — | ND | 0.68 |
| X32966-15-5 | 8:30 | 49.5 | 6.91 | A-A-1 | 1.004 | — | ND | 0.22 |

We claim:

1. A process for rendering a polyamine-epihalohydrin resin storage stable, comprising:

treating a composition containing a polyamine-epihalohydrin resin, the composition comprising a solids content of at least 15 wt % and including CPD-forming species, and wherein the resin is formed in a reaction having a molar ratio of epihalohydrin to secondary amine group of less than 0.50, with at least one enzymatic agent under conditions to at least one of inhibit, reduce and remove the CPD-forming species to obtain a gelatin storage stable reduced CPD-forming resin so that the composition containing the reduced CPD-forming polyamine-epihalohydrin resin when stored for 24 hours at 50° C., and a pH of about 1.0 releases less than about 100 ppm dry basis of CPD, wherein the solids content of the composition containing a polyamine-epihalohydrin resin is at least 15 wt % when treated with the at least one enzymatic agent and wherein the at least one enzymatic agent is selected from the group consisting of an esterase, a lipase, a protease or a combination thereof.

2. The process according to claim 1, wherein the composition containing the reduced the CPD-forming polyamine-epihalohydrin resin when stored for 24 hours at 50° C., and a pH of about 1.0 releases less than about 50 ppm dry basis of CPD.

3. The process according to claim 1, wherein the treatment conditions comprise a temperature of from about 20° C. to 60° C.

4. The process according to claim 3, wherein the treatment conditions comprise a temperature of from about 20° C. to 40° C.

5. The process according to claim 1, wherein the treatment conditions comprise a reaction time of from about 30 minutes to about 96 hours.

6. The process according to claim 5, wherein the treatment conditions comprise a reaction time of from about 2 hours to about 12 hours.

7. The process according to claim 1, wherein the treatment conditions comprise a pH of from about 2.5 to about 9.

8. The process according to claim 7, wherein the treatment conditions comprise a pH of from about 6 to about 9.

9. The process according to claim 8, wherein the treatment conditions comprise a pH from about 6 to about 8.5.

10. The process according to claim 1, wherein the ratio of at least one enzymatic agent to polyamine-epihalohydrin resin (dry basis) is from about 1:1600 to about 1:1.5.

11. The process according to claim 10, wherein the ratio of at least one enzymatic agent to polyamine-epihalohydrin resin (dry basis) is from about 1:160 to about 1:4.

12. The process according to claim 1, wherein the ratio of at least one enzymatic agent (active enzyme, dry basis) to polyamine-epihalohydrin resin (dry basis) is from about 0.04:1600 to about 0.04:1.5.

13. The process according to claim 1, wherein the solids content is 15 to 50 wt % active solids, the treatment conditions comprise a temperature of from about 0° C. to about 35° C., a reaction time of from about 4 to about 24 hours, a pH of from about 6.9 to about 7.9, the ratio of at least one enzymatic agent to polyamine-epihalohydrin resin (dry basis) is from about 1:20 to about 1:8.

14. The process according to claim 1, wherein the at least one enzymatic agent is a protease in the subtilisin group.

15. The process according to claim 1, wherein the at least one enzymatic agent has esterase activity.

16. The process according to claim 1, wherein the at least one enzymatic agent is produced from a microorganism selected from the group consisting of *Bacillus licheniformis* (Swiss-Prot Accession Number: P00780), or *Bacillus amyloliquifaciens* (P00782), and *Bacillus lentus* (P29600).

17. The process according to claim 1, wherein the at least one enzymatic agent is in the subtilisin group.

18. The process according to claim 1, wherein the resin is characterized by the presence of the functionality represented by the formula:

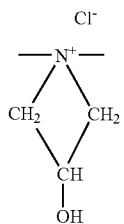

19. The process according to claim 1, wherein the resin is characterized by the presence of the functionality represented by the formula:

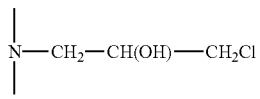

20. The process according to claim 1, wherein the resin is characterized by the presence of the functionality represented by the formula:

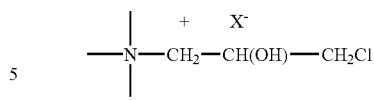

wherein X is an anion.

21. The process according to claim 1, wherein, simultaneously, prior to or subsequent to the treating a composition containing polyamineepihalohydrin resin to obtain a reduced CPD-forming resin, the resin is treated to reduce at least one of epihalohydrins, epihalohydrin hydrolysis by-products and organic halogen bound to the polymer backbone.

22. The process according to claim 1, wherein at least one of simultaneously with, prior to or subsequent to the treating a composition containing polyamine-epihalohydrin resin to obtain a reduced CPD-forming resin, the resin is contacted with at least one microorganism or at least one enzyme isolated from said at least one microorganism in an amount and at a pH and temperature effective to dehalogenate residual quantities of organically bound halogen.

23. The process according to claim 22, wherein said at least one microorganism or at least one enzyme isolated from said at least one microorganism is a hydrogen halide lysase type dehalogenase.

24. The process according to claim 22, wherein said at least one microorganism or at least one enzyme isolated from said at least one microorganism comprises at least one of Arthrobacter histidinolovorans (HK1) and Agrobacteriwn radiobacter (HK7).

25. The process according to claim 22, wherein said at least one microorganism comprises a mixture comprising at least one of Agrobacteriutn radiobacter (HK7) and Arthrobacter histidinolovorans (HK1).

26. The process according to claim 1, wherein, simultaneously with the treating a composition containing polyamine-epihalohydrin resin to obtain a reduced CPD-forming resin, the CPD-forming resin is contacted with at least one microorganism or at least one enzyme isolated from said at least one microorganism in an amount and at a pH and temperature effective to dehalogenate residual quantities of organically bound halogen.

27. The process according to claim 26, wherein the treatment conditions comprise a reaction time of 48 hours or less.

28. The process according to claim 26, wherein the temperature is from about 20 C. to 35 C.

29. The process according to claim 26, wherein the treatment conditions comprise a pH of from about 6.5 to 8.0.

30. The process according to claim 26, wherein said at least one microorganism or at least one enzyme isolated from said at least one microorganism is a hydrogen halide lysase type dehalogenase.

31. The process according to claim 26 wherein said at least one microorganism or at least one enzyme isolated from said at least one microorganism comprises at least one of Arthrobacter histidinolovorans (HK1) and Agrobacterium radiobacter (HK7).

32. The process according to claim 26, wherein said at least one microorganism comprises a mixture comprising at least one of Agrobacterium radiobacter (HK7) and Arthrobacter histidinolovorans (HK1).

33. The process according to claim 26, wherein the treatment conditions comprise a reaction time of 48 hours or less, a temperature of from about 20 C. to 35 0C, a pH of from about 6.5 to about 8.0, and the ratio of at least one enzymatic agent to polyamine-epihalohydrin resin (dry basis) is from about 1:1600 to about 1:1.5 and said at least one microorganism comprises a mixture comprising at least one of Agrobacterium radiobacter (HK7) and Arthrobacter histidinolovorans (HK1).

34. The process according to claim 26, wherein the ratio of said at least one enzymatic agent to polyamine-epihalohydrin resin (dry basis) is from about 1:1600 to about 1:1.5.

35. A process for preparing a paper product, comprising:
treating a composition containing a polyamine-epihalohydrin resin, the composition comprising a solids content of at least 15 wt % and including CPD-forming species, and wherein the resin is formed in a reaction having a molar ratio of epihalohydrin to secondary amine group of less than 0.50, with at least one enzymatic agent under conditions to at least one of inhibit, reduce and remove the CPD-forming species to obtain a gelatin storage stable reduced CPD-forming resin, and forming a paper product with the reduced CPD-forming polyamine-epihalohydrin resin, so that a paper product, when corrected for adding at about a 1 wt % addition level of the reduced CPD-forming resin, contains less than about 250 ppb of CPD, wherein the solids content of the composition containing a polyamine-epihalohydrin resin is at least 15 wt % when treated with the at least one enzymatic agent and wherein the at least one enzymatic agent is selected from the group consisting of an esterase, a lipase, a protease or a combination thereof.

36. The process according to claim 35, wherein the paper product, when corrected for adding at about a 1 wt % addition level of the reduced CPD-forming resin, contains less than about 50 ppb of CPD.

37. The process according to claim 35, wherein the solids content is 15 to 50 wt % active solids, the temperature of the reaction is from about 0° C. to about 35° C., the reaction time is from about 4 to 24 hours and the pH of the reaction is from about 6.9 to about 7.9, the ratio of at least one enzymatic agent to polyamine-epihalohydrin resin (dry basis) is from about 1:20 to about 1:8.

* * * * *